(12) United States Patent
Dai et al.

(10) Patent No.: US 10,000,486 B2
(45) Date of Patent: Jun. 19, 2018

(54) ANTIVIRAL DRUGS FOR TREATMENT OF ARENAVIRUS INFECTION

(71) Applicant: Kineta Four, LLC, Seattle, WA (US)

(72) Inventors: Dongcheng Dai, Corvallis, OR (US);
James R. Burgeson, Albany, OR (US);
Sean M. Amberg, Corvallis, OR (US);
Dennis E. Hruby, Albany, OR (US)

(73) Assignee: Kineta Viral Hemorrhagic Fever, LLC, Seattle, WA (US)

(*) Notice: Subject to any disclaimer, the term of this patent is extended or adjusted under 35 U.S.C. 154(b) by 0 days. days.

(21) Appl. No.: 15/353,351

(22) Filed: Nov. 16, 2016

(65) Prior Publication Data
US 2017/0137422 A1 May 18, 2017

Related U.S. Application Data

(63) Continuation of application No. 14/379,028, filed as application No. PCT/US2013/026173 on Feb. 14, 2013, now Pat. No. 9,498,470.

(60) Provisional application No. 61/600,036, filed on Feb. 17, 2012.

(51) Int. Cl.
| | | |
|---|---|---|
| C07D 235/08 | (2006.01) | |
| C07D 471/04 | (2006.01) | |
| C07D 235/06 | (2006.01) | |
| C07D 401/04 | (2006.01) | |
| C07D 405/10 | (2006.01) | |
| C07D 401/10 | (2006.01) | |
| C07D 209/08 | (2006.01) | |

(52) U.S. Cl.
CPC ......... *C07D 471/04* (2013.01); *C07D 209/08* (2013.01); *C07D 235/06* (2013.01); *C07D 235/08* (2013.01); *C07D 401/04* (2013.01); *C07D 401/10* (2013.01); *C07D 405/10* (2013.01)

(58) Field of Classification Search
CPC .......................... C07D 235/08; C07D 471/04
See application file for complete search history.

(56) References Cited

U.S. PATENT DOCUMENTS

| | | | |
|---|---|---|---|
| 5,554,630 | A | 9/1996 | Teuber et al. |
| 5,864,043 | A | 1/1999 | Narr et al. |
| 7,074,801 | B1 | 7/2006 | Yoshida et al. |
| 2007/0254934 | A1 | 11/2007 | Hruby et al. |
| 2008/0090870 | A1 | 4/2008 | Defossa et al. |
| 2008/0300265 | A1 | 12/2008 | Hruby et al. |
| 2009/0012107 | A1 | 1/2009 | Aman et al. |
| 2010/0160308 | A1 | 6/2010 | Cai et al. |
| 2011/0064693 | A1 | 3/2011 | Dai et al. |
| 2011/0172281 | A1 | 7/2011 | Hruby et al. |

FOREIGN PATENT DOCUMENTS

| | | |
|---|---|---|
| JP | 63-157157 A | 6/1988 |
| JP | 04-46352 A | 2/1992 |
| WO | 95/04723 A1 | 2/1995 |

OTHER PUBLICATIONS

Dai et al., Bioorganic & Medicinal Chemistry Letters, 23, published online Dec. 1, 2012, pp. 744-749.*
Chemical Abstracts Registry No. 1226902-71-1, indexed in the Registry file on STN CAS Online Jun. 3, 2010, 1 page.
Chemical Abstracts Registry No. 313483-27-1, indexed in the Registry file on STN CAS Online Jan. 11, 2001, 1 page.
Chemical Abstracts Registry No. 326026-82-8, indexed in the Registry file on STN CAS Online Mar. 7, 2001, 1 page.
Chemical Abstracts Registry No. 328558-99-2, indexed in the Registry file on STN CAS Online Mar. 25, 2001, 1 page.
Chemical Abstracts Registry No. 857258-12-9, indexed in the Registry file on STN CAS Online Jul. 27, 2005, 1 page.
Chemical Abstracts Registry No. 929095-71-6, indexed in the Registry file on STN CAS Online Apr. 4, 2007, 1 page.
Extended European Search Report dated Jun. 6, 2016, issued in corresponding European Application No. 13749809.3, filed Feb. 14, 2013, 10 pages.
International Search Report and Written Opinion dated Apr. 26, 2014, issued in International Application No. PCT/US2013/026173, filed Feb. 14, 2013, 7 pages.
Mader, M., et al., "Imidazolyl Benzimidazoles and Imidazo[4,5-b]pyridines as Potent p38α MAP Kinase Inhibitors With Excellent In Vivo Antiinflammatory Properties," Bioorganic & Medicinal Chemistry Letters 18(1)179-183, Jan. 2008.
Notice of Defects in Patent Application, dated Aug. 21, 2016, issued in Israeli Application No. 234091, filed Feb. 14, 2013, 8 pages.
Okada, M., et al., Chemical Abstracts Registry No. 168630-06-06; Document No. CA 123:228181, 1995, 4 pages.
Patent Examination Report No. 2, dated Jun. 23, 2016, issued in Australian Patent Application No. 2013221475, filed Feb. 14, 2013, 4 pages.
Shiino, Y., and M. Matsumoto, Chemical Abstracts Document No. 110:85382, 1989, 2 pages.
Solanki, S., et al., "Benzimidazole Inhibitors Induce a DFG-Out Conformation of Never in Mitosis Gene A-Related Kinase 2 (Nek2) Without Binding to the Back Pocket and Reveal a Nonlinear Structure-Activity Relationship," Journal of Medicinal Chemistry 54(6):1626-1639, Mar. 2011.
Ueda, H., Chemical Abstracts Document No. CA 117:17297, Feb. 17, 1992, 2 pages.
International Preliminary Report on Patentability dated Jan. 27, 2015, issued in International Application No. PCT/US2013/026173, filed Feb. 14, 2013, 6 pages.

\* cited by examiner

*Primary Examiner* — Laura L. Stockton

(57) ABSTRACT

Compounds, methods and pharmaceutical compositions for treating viral infections, by administering certain compounds in therapeutically effective amounts are disclosed. Methods for preparing the compounds and methods of using the compounds and pharmaceutical compositions thereof are also disclosed. In particular, the treatment and prophylaxis of viral infections such as caused by the Arenavirus family such as Lassa fever, Argentine hemorrhagic fever, Bolivian hemorrhagic fever, and Venezuelan hemorrhagic fever.

2 Claims, No Drawings

ANTIVIRAL DRUGS FOR TREATMENT OF ARENAVIRUS INFECTION

CROSS-REFERENCES TO RELATED APPLICATIONS

This application is a continuation of U.S. application Ser. No. 14/379,028, filed Aug. 15, 2014 (now U.S. Pat. No. 9,498,470), which is a 371 National Phase Application of International Application No. PCT/US2013/026173, filed Feb. 14, 2013, which claims the benefit of U.S. Provisional Application No. 61/600,036, filed Feb. 17, 2012. Each application is incorporated herein by reference in its entirety.

STATEMENT REGARDING FEDERALLY SPONSORED RESEARCH OR DEVELOPMENT

The research described herein was supported in part by funds from the U.S. Government (NIH SBIR grant R44AI056525 and Grant no. R01AI093387) and the U.S. Government has certain rights in the invention.

FIELD OF THE INVENTION

This invention relates to the use of benzimidaziole derivatives and analogs, as well as compositions containing the same, for the treatment or prophylaxis of viral diseases associated with the *arenavirus* family such as Lassa fever, Argentine hemorrhagic fever, Bolivian hemorrhagic fever, and Venezuelan hemorrhagic fever.

BACKGROUND OF THE INVENTION

Viral hemorrhagic fever is a serious illness characterized by extensive vascular damage and bleeding diathesis, fever, and multiple organ involvement. Many different viruses can cause this syndrome, each with its own animal reservoir, mode of transmission, fatality rate, and clinical outcome in humans. These viruses are distributed throughout four virus families, the Arenaviridae, Bunyaviridae, Filoviridae, and Flaviviridae. Several of these viruses generate significant morbidity and mortality and can be highly infectious by aerosol dissemination, promoting concern about weaponization (for an overview, see 3). In 1999, the Centers for Disease Control and Prevention (CDC) identified and categorized potential biological terrorism agents as part of a Congressional initiative to upgrade bioterrorism response capabilities (30). Filoviruses and arenaviruses were designated as Category A, defined as those pathogens with the highest potential impact on public health and safety, potential for large-scale dissemination, capability for civil disruption, and greatest unmet need for public health preparedness. The National Institute of Allergy and Infectious Diseases (NIAID) has since expanded the Category A list by adding several hemorrhagic bunyaviruses and flaviviruses (27). In addition, the Working Group on Civilian Biodefense described several hemorrhagic fever viruses, including Lassa, as those with the greatest risk for use as biological weapons and recommended the pursuit of new antiviral therapies (3).

Prevention and treatment options for hemorrhagic fever viruses are limited. With the exception of an effective vaccine for yellow fever, no licensed vaccines or FDA-approved antiviral drugs are available. Intravenous ribavirin has been used with some success to treat arenaviruses and bunyaviruses, although its use has significant limitations (see below). In addition, there have been recent reports of promising vaccines for Ebola (19) and Lassa (16). Although a successful vaccine could be a critical component of an effective biodefense, the typical delay to onset of immunity, potential side-effects, cost, and logistics associated with large-scale civilian vaccinations against a low-risk threat agent suggest that a comprehensive biodefense include a separate rapid-response element. Thus there remains an urgent need to develop safe and effective products to protect against potential biological attack.

Lassa fever virus is a member of the Arenaviridae family, a family of enveloped RNA viruses (4). *Arenavirus* infection in rodents, the natural host animal, is usually chronic and asymptomatic. Several arenaviruses can cause severe hemorrhagic fever in humans, including Lassa, Machupo, Guanarito, and Junin viruses. Transmission to humans can result from direct contact with infected rodents or their habitat, through aerosolized rodent secretions, or through contact with the body fluids of an infected person. Although arenaviruses are found world-wide, most of the viral species are geographically localized to a particular region, reflecting the range of the specific rodent host involved. The Arenaviridae family contains a single genus (*Arenavirus*) that is divided into two major lineages based on phylogenetic and serological examination. Lassa fever is a member of the Old World arenaviruses; the New World arenaviruses can be further divided into three clades (A-C), one of which (clade B) contains several of the pathogenic, Category A hemorrhagic fever viruses.

Lassa fever is endemic in West Africa, particularly the countries of Guinea, Liberia, Sierra Leone, and Nigeria. Human infections are estimated at 100,000 to 500,000 per year (25). Initial symptoms of Lassa fever appear about 10 days after exposure, and include fever, sore throat, chest and back pain, cough, vomiting, diarrhea, conjunctivitis, facial swelling, proteinuria, and mucosal bleeding. Clinical diagnosis is often difficult due to the nonspecific nature of the symptoms. In fatal cases, continuing progression of symptoms leads to the onset of shock. Among hospitalized patients, the mortality rate is 15-20% (23), although the fatality rate for some outbreaks has been reported higher than 50% (14). Infectious virus can remain in the bodily fluids of convalescent patients for several weeks (34). Transient or permanent deafness is common in survivors (10) and appears to be just as frequent in mild or asymptomatic cases as it is in severe cases (22). Lassa fever is occasionally imported into Europe (17) and the U.S., most recently in 2004 (7). The risk of the virus becoming endemic outside of West Africa appears low due to the nature of the rodent host. However, the combination of increased world travel and viral adaptation presents a finite possibility of a virus "jumping" into a new ecosystem. For example, West Nile virus was introduced into the New York City area in 1999 and is now endemic in the U.S.

A small trial conducted in Sierra Leone in the 1980s demonstrated that mortality from Lassa fever can be reduced in high-risk patients by treatment with intravenous ribavirin, a nucleoside analog that exhibits nonspecific antiviral activity (24). Ribavirin has been shown to inhibit Lassa fever viral RNA synthesis in vitro (18). Although of limited availability, intravenous ribavirin is available for compassionate use under an investigational new drug protocol. It is also available in oral form for treating hepatitis C (in combination with interferon), although less is known about the efficacy of orally-administered ribavirin for treating Lassa fever. As a nucleoside analog, ribavirin can interfere with DNA and RNA replication, and in fact teratogenicity and embryo lethality have been seen in several animal species. It is therefore contraindicated for pregnant patients (a pregnancy category X drug). In addition, it is associated with a dose-related hemolytic anemia; although the anemia is reversible, anemia-associated cardiac and pulmonary events occur in approximately 10% of hepatitis C patients receiving ribavirin-interferon therapy. Intravenous ribavirin is expensive, and daily I.V. administration to a large civilian population in an emergency would be a cumbersome approach. It is possible that further study may eventually support the use of oral interferon, either alone or in combination with other antivirals, for treatment of Lassa fever. Successful antiviral therapy often involves administering a combination of pharmaceuticals, such as the treatment of chronic hepatitis C with interferon and ribavirin, and treatment of AIDS with highly active antiretroviral therapy (HAART), a cocktail of three different drugs. Because of the high mutation rate and the quasispecies nature associated with viruses, treatment with compounds that act on multiple, distinct targets can be more successful than treatment with a single drug.

The *arenavirus* genome consists of two segments of single-stranded RNA, each of which codes for two genes in opposite orientations (referred to as ambisense). The larger of the two segments, the L RNA (7.2 kb), encodes the L and Z proteins. The L protein is the RNA dependent RNA polymerase, and the Z protein is a small zinc-binding RING finger protein which is involved in virus budding (29). The S RNA (3.4 kb) encodes the nucleoprotein (NP) and the envelope glycoprotein precursor (GPC).

The envelope glycoprotein is embedded in the lipid bilayer that surrounds the viral nucleocapsid. The characteristics of the *arenavirus* glycoprotein suggest that it can be classified as a Type I envelope (15), which is typified by influenza hemagglutinin and found also in retroviruses, paramyxoviruses, coronaviruses, and filoviruses (8). Type I envelopes function both to attach the virus to specific host cell receptors and also to mediate fusion of the viral membrane with the host membrane, thereby depositing the viral genome inside the target cell. Cotranslational translocation of the envelope protein across the membrane of the endoplasmic reticulum is facilitated by an N-terminal signal peptide that is subsequently removed by a signal peptidase. Post-translational proteolysis further processes the envelope into an N-terminal subunit (denoted GP1 for arenaviruses), which contains the receptor binding determinants, and a C-terminal transmembrane subunit (GP2), which is capable of undergoing the dramatic conformational rearrangements that are associated with membrane fusion. The two subunits remain associated with one another and assemble into trimeric complexes of this heterodimer, although *arenavirus* envelope glycoproteins have been reported to have a tetrameric structure (5). Mature envelope glycoproteins accumulate at the site of viral budding, such as the plasma membrane, and thus are embedded within the envelope that the virus acquires as viral budding occurs.

The signal peptide of the *arenavirus* glycoprotein is quite unusual (12); at 58 amino acids in length, it is larger than most signal peptides (13). In addition, it remains associated with the envelope and with mature virions, and appears to be important for the subsequent GP1-GP2 processing (11). This processing is essential for envelope function and is mediated by the cellular subtilase SKI-1/S1P (1, 20, 21). The envelope glycoprotein interacts directly with the host cellular receptor to facilitate viral entry into the target cell. The receptor for Old World arenaviruses is α-dystroglycan (6), a major component of the dystrophin glycoprotein complex. The New World arenaviruses appear to have diverged from this receptor, as only the clade C viruses use α-dystroglycan as a major receptor (32). The receptor for the New World clades A and B arenaviruses has not yet been identified.

SUMMARY OF THE INVENTION

The present invention provides a compound having the following general Formula I or a pharmaceutically acceptable salt thereof:

Formula I wherein, X is C-D-A-$Ar^2$ and L is independently N or C—R; or X is independently N or C—R and L is C-D-A-$Ar^2$; wherein D-A is independently selected from the group consisting of: $CR^1R^2$—NR', S—$CR^1R^2$, O—$CR^1R^2$, $R^3R^4C$—$CR^5R^6$, $R^7C$=$CR^8$, and C≡C; and E, G, M, and Q are independently N or C—R; J and K are independently N or C;

R is selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;

R' is as follows:
  (a) R' is selected from the group consisting of: hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl;
  (b) R' together with the nitrogen atom it is attached to, some carbons of $Ar^2$, form a substituted or unsubstituted ring, which optionally includes one or more heteroatoms in the ring;
  (c) R' together with the nitrogen atom it is attached to, the carbon atom $R^1$ and $R^2$ are attached to, $R^1$ or $R^2$, form a substituted or unsubstituted ring, which optionally includes one or more heteroatoms in the ring; or d) R' together with the nitrogen atom it is attached to, the carbon atom $R^1$ and $R^2$ are attached to, some carbons of the aromatic ring next to this carbon, form a substituted or unsubstituted ring, which optionally includes one or more heteroatoms in the ring;

$R^1$ and $R^2$ are as follows:
(a) independently selected from the group consisting of hydrogen, halogen, haloalkyl, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) $R^1$ and $R^2$ together with the carbon atom they are attached to form a substituted or unsubstituted ring, which optionally includes one or more heteroatoms in the ring;
(c) $R^1$ or $R^2$ together with the carbon atom it is attached to, the sulfur or oxygen atom next to this carbon, some carbons of the aromatic ring next to this atom, form a substituted or unsubstituted ring, which optionally includes one or more heteroatoms in the ring;
(d) when D-A is $CR^1R^2$—NR, $R^1$ or $R^2$ together with the carbon atom it is attached to, some carbons of the aromatic ring next to this carbon, form a substituted or unsubstituted ring, which optionally includes one or more heteroatoms in the ring; or
(e) $R^1$ or $R^2$ together with the carbon atom it is attached to, the nitrogen atom when D-A is $CR^1R^2$—NR, some carbons of $Ar^2$, form a substituted or unsubstituted ring, which optionally includes one or more heteroatoms in the ring;

$R^3$, $R^4$, $R^5$, $R^6$ are as follows:
(a) $R^3$, $R^4$, $R^5$, $R^6$ are independently selected from the group consisting of: hydrogen, halogen, haloalkyl, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) $R^3$ and $R^4$ together with the carbon atom they are attached to form a substituted or unsubstituted ring, which optionally includes one or more heteroatoms in the ring;
(c) $R^3$ or $R^4$ together with the carbon atom it is attached to, $R^5$ or $R^6$ together with the carbon atom it is attached to, form a substituted or unsubstituted ring, which optionally includes one or more heteroatoms in the ring;
(d) $R^3$ or $R^4$ together with the carbon atom it is attached to, the carbon atom $R^5$ or $R^6$ is attached to, some carbons of $Ar^2$, form a substituted or unsubstituted ring, which optionally includes one or more heteroatoms in the ring;
(e) $R^3$ or $R^4$ together with the carbon atom it is attached to, some carbons of the aromatic ring next to this carbon, form a substituted or unsubstituted ring, which optionally includes one or more heteroatoms in the ring;
(f) $R^5$ and $R^6$ together with the carbon atom they are attached to form a substituted or unsubstituted ring, which optionally includes one or more heteroatoms in the ring;
(g) $R^5$ or $R^6$ together with the carbon atom it is attached to, some carbons of $Ar^2$, form a substituted or unsubstituted ring, which optionally includes one or more heteroatoms in the ring; or
(h) $R^5$ or $R^6$ together with the carbon atom it is attached to, the carbon atom $R^3$ or $R^4$ is attached to, some carbons of the aromatic ring next to this carbon, form a substituted or unsubstituted ring, which optionally includes one or more heteroatoms in the ring;

$R^7$ and $R^8$ are as follows:
(a) $R^7$ and $R^8$ are independently selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;
(b) $R^7$ and $R^8$ together with the carbon atoms they are attached to form a substituted or unsubstituted ring, which optionally includes one or more heteroatoms in the ring;
(c) $R^7$ together with the carbon atom it is attached to, some carbons of the aromatic ring next to this carbon, form a substituted or unsubstituted ring, which optionally includes one or more heteroatoms in the ring;
(d) $R^7$ together with the carbon atom it is attached to, the carbon atom $R^8$ is attached to, some carbons of $Ar^2$, form a substituted or unsubstituted ring, which optionally includes one or more heteroatoms in the ring;
(e) $R^8$ together with the carbon atom it is attached to, some carbons of $Ar^2$, form a substituted or unsubstituted ring, which optionally includes one or more heteroatoms in the ring; or
(f) $R^8$ together with the carbon atom it is attached to, the carbon atom $R^7$ is attached to, some carbons of the aromatic ring next to this carbon, form a substituted or unsubstituted ring, which optionally includes one or more heteroatoms in the ring; and $Ar^1$ and $Ar^2$ are independently (un)substituted aryl or heteroaryl.

The present invention also provides a pharmaceutical formulation comprising the compound of Formula I and one or more pharmaceutically acceptable ingredient or excipient.

The present invention further provides a method for the treatment or prophylaxis of a viral infection or disease associated therewith, comprising administering in a therapeutically effective amount to a mammal in need thereof, a compound of Formula I or a pharmaceutically acceptable salt thereof.

The present invention also provides a compound having the following general Formula II or a pharmaceutically acceptable salt thereof:

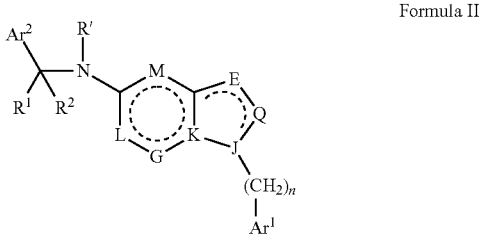

Formula II wherein, E is independently N, N⁺—O⁻, or C—R; G, L, M, and Q are independently N or C—R; and J and K are independently N or C with the proviso that when n=0, E and J cannot both be N;

R is selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;

R' is as follows:
(a) R' is independently selected from the group consisting of: hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) R' together with the nitrogen atom it is attached to, the carbon atom R¹ and R² are attached to, R¹ or R², form a substituted or unsubstituted ring, which optionally includes one or more heteroatoms in the ring;
(c) R' together with the nitrogen atom it is attached to, the carbon atom R¹ and R² are attached to, some carbons of Ar², form a substituted or unsubstituted ring, which optionally includes one or more heteroatoms in the ring; or
(d) R' together with the nitrogen atom it is attached to, some carbons of the aromatic ring next to this nitrogen, form a substituted or unsubstituted ring, which optionally includes one or more heteroatoms in the ring;

R¹ and R² are as follows:
(a) R¹ and R² are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) R¹ and R² together with the carbon atom they are attached to form a substituted or unsubstituted ring, which optionally include one or more heteroatoms in the ring;
(c) R¹ or R² together with the carbon atom it is attached to, the nitrogen next to this carbon, and some carbons of the aromatic ring next to this nitrogen, form a substituted or unsubstituted ring, which optionally include one or more heteroatoms in the ring; or
(d) R¹ or R² together with the carbon atom it is attached to, some carbons of Ar², form a substituted or unsubstituted ring, which optionally includes one or more heteroatoms in the ring;

n is an integer from 0-4; and
Ar¹ and Ar² are independently (un)substituted aryl or heteroaryl.

The present invention further provides a pharmaceutical formulation comprising the compound of Formula II and one or more pharmaceutically acceptable ingredient or excipient.

The present invention also provides a method for the treatment or prophylaxis of a viral infection or disease associated therewith, comprising administering in a therapeutically effective amount to a mammal in need thereof, a compound of Formula II or a pharmaceutically acceptable salt thereof.

Other objects and advantages of the present invention will become apparent from the following description and appended claims.

DETAILED DESCRIPTION OF THE INVENTION

The compounds of the invention include compounds which are of the following general Formula I or a pharmaceutically acceptable salt thereof:

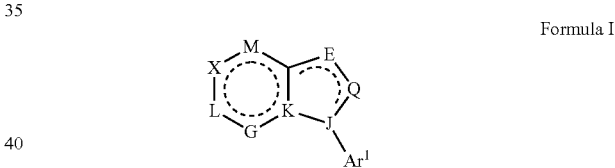

Formula I wherein, X is C-D-A-Ar² and L is independently N or C—R; or X is independently N or C—R and L is C-D-A-Ar²; wherein D-A is independently selected from the group consisting of: CR¹R²—NR', S—CR¹R², O—CR¹R², R³R⁴C—CR⁵R⁶, R⁷C=CR⁸, and C≡C; and E, G, M, and Q are independently N or C—R; J and K are independently N or C;

R is selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;

R' is as follows:
(a) R' is selected from the group consisting of: hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl;
(b) R' together with the nitrogen atom it is attached to, some carbons of $Ar^2$, form a substituted or unsubstituted ring, which optionally includes one or more heteroatoms in the ring;
(c) R' together with the nitrogen atom it is attached to, the carbon atom $R^1$ and $R^2$ are attached to, $R^1$ or $R^2$, form a substituted or unsubstituted ring, which optionally includes one or more heteroatoms in the ring; or
d) R' together with the nitrogen atom it is attached to, the carbon atom $R^1$ and $R^2$ are attached to, some carbons of the aromatic ring next to this carbon, form a substituted or unsubstituted ring, which optionally includes one or more heteroatoms in the ring;

$R^1$ and $R^2$ are as follows:
(a) independently selected from the group consisting of hydrogen, halogen, haloalkyl, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) $R^1$ and $R^2$ together with the carbon atom they are attached to form a substituted or unsubstituted ring, which optionally includes one or more heteroatoms in the ring;
(c) $R^1$ or $R^2$ together with the carbon atom it is attached to, the sulfur or oxygen atom next to this carbon, some carbons of the aromatic ring next to this atom, form a substituted or unsubstituted ring, which optionally includes one or more heteroatoms in the ring;
(d) when D-A is $CR^1R^2$—NR, $R^1$ or $R^2$ together with the carbon atom it is attached to, some carbons of the aromatic ring next to this carbon, form a substituted or unsubstituted ring, which optionally includes one or more heteroatoms in the ring; or
(e) $R^1$ or $R^2$ together with the carbon atom it is attached to, the nitrogen atom when D-A is $CR^1R^2$—NR, some carbons of $Ar^2$, form a substituted or unsubstituted ring, which optionally includes one or more heteroatoms in the ring;

$R^3$, $R^4$, $R^5$, $R^6$ are as follows:
(a) $R^3$, $R^4$, $R^5$, $R^6$ are independently selected from the group consisting of: hydrogen, halogen, haloalkyl, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) $R^3$ and $R^4$ together with the carbon atom they are attached to form a substituted or unsubstituted ring, which optionally includes one or more heteroatoms in the ring;
(c) $R^3$ or $R^4$ together with the carbon atom it is attached to, $R^5$ or $R^6$ together with the carbon atom it is attached to, form a substituted or unsubstituted ring, which optionally includes one or more heteroatoms in the ring;
(d) $R^3$ or $R^4$ together with the carbon atom it is attached to, the carbon atom $R^5$ or $R^6$ is attached to, some carbons of $Ar^2$, form a substituted or unsubstituted ring, which optionally includes one or more heteroatoms in the ring;
(e) $R^3$ or $R^4$ together with the carbon atom it is attached to, some carbons of the aromatic ring next to this carbon, form a substituted or unsubstituted ring, which optionally includes one or more heteroatoms in the ring;
(f) $R^5$ and $R^6$ together with the carbon atom they are attached to form a substituted or unsubstituted ring, which optionally includes one or more heteroatoms in the ring;
(g) $R^5$ or $R^6$ together with the carbon atom it is attached to, some carbons of $Ar^2$, form a substituted or unsubstituted ring, which optionally includes one or more heteroatoms in the ring; or
(h) $R^5$ or $R^6$ together with the carbon atom it is attached to, the carbon atom $R^3$ or $R^4$ is attached to, some carbons of the aromatic ring next to this carbon, form a substituted or unsubstituted ring, which optionally includes one or more heteroatoms in the ring;

$R^7$ and $R^8$ are as follows:
(a) $R^7$ and $R^8$ are independently selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;
(b) $R^7$ and $R^8$ together with the carbon atoms they are attached to form a substituted or unsubstituted ring, which optionally includes one or more heteroatoms in the ring;
(c) $R^7$ together with the carbon atom it is attached to, some carbons of the aromatic ring next to this carbon, form a substituted or unsubstituted ring, which optionally includes one or more heteroatoms in the ring;
(d) $R^7$ together with the carbon atom it is attached to, the carbon atom $R^8$ is attached to, some carbons of $Ar^2$, form a substituted or unsubstituted ring, which optionally includes one or more heteroatoms in the ring;
(e) $R^8$ together with the carbon atom it is attached to, some carbons of $Ar^2$, form a substituted or unsubstituted ring, which optionally includes one or more heteroatoms in the ring; or (f) R⁸ together with the carbon atom it is attached to, the carbon atom R⁷ is attached to, some carbons of the aromatic ring next to this carbon, form a substituted or unsubstituted ring, which optionally includes one or more heteroatoms in the ring; and Ar¹ and Ar² are independently (un)substituted aryl or heteroaryl.

Preferably for compounds of Formula I, each of E and J is N; each of G, M, Q and L is C—R; K is C; and D-A is R⁷C=CR⁸, wherein each of R⁷ and R⁸ are H and the double bond in R⁷C=CR⁸ has a cis configuration. Also preferably, D-A is O—CR¹R² and each of R¹ and R² are H.

Preferred compounds of Formula I also include the compounds of Formula Ia:

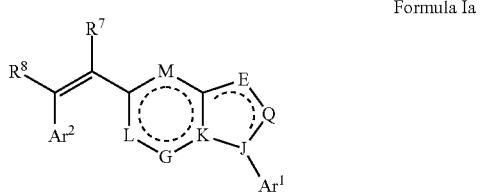

Formula Ia wherein E, G, J, L, M, Q, K, R⁷, R⁸, Ar¹ and Ar² are as defined above in Formula I.

Preferably, the compound of Formula I of the present invention is selected from the group consisting of 1-(4-ethoxyphenyl)-5-[(E)-2-(4-ethylphenyl)vinyl]-benzimidazole; 1-(4-ethoxyphenyl)-5-[(Z)-2-(4-ethylphenyl)vinyl]-benzimidazole; 5-[(E)-2-(4-isopropylphenyl)vinyl]-1-(4-methoxyphenyl)benzimidazole; 5-[(E)-2-(4-tert-butylphenyl)vinyl]-1-(4-ethoxyphenyl)benzimidazole; 5-[(Z)-2-(4-tert-butylphenyl)vinyl]-1-(4-ethoxyphenyl)-benzimidazole; 5-[(E)-2-(4-tert-butylphenyl)vinyl]-1-(4-isopropoxyphenyl)-benzimidazole; 5-[(Z)-2-(4-tert-butylphenyl)vinyl]-1-(4-isopropoxyphenyl)-benzimidazole; 5-[(E)-2-(4-ethylphenyl)vinyl]-1-(4-isopropoxyphenyl)-benzimidazole; 5-[(Z)-2-(4-ethylphenyl)vinyl]-1-(4-isopropoxyphenyl)-benzimidazole; 1-(4-ethoxyphenyl)-5-[(E)-2-[4-(trifluoromethoxy)phenyl]vinyl]benzimidazole; 1-(4-ethoxyphenyl)-5-[(Z)-2-[4-(trifluoromethoxy)-phenyl]vinyl]benzimidazole; 1-(4-ethoxyphenyl)-5-[(E)-2-[4-(trifluoromethyl)phenyl]vinyl]benzimidazole; 1-(4-ethoxyphenyl)-5-[(Z)-2-[4-(trifluoromethyl)phenyl]-vinyl]benzimidazole; 1-(4-tert-butoxyphenyl)-5-[(E)-2-(4-ethylphenyl)-vinyl]benzimidazole; 1-(4-tert-butoxyphenyl)-5-[(Z)-2-(4-ethylphenyl)-vinyl]benzimidazole; 1-(4-tert-butoxyphenyl)-5-[(E)-2-(4-tert-butylphenyl)vinyl]-benzimidazole; 1-(4-tert-butoxyphenyl)-5-[(Z)-2-(4-tert-butylphenyl)vinyl]benzimidazole; 1-(5-ethoxy-2-pyridyl)-5-[(E)-2-(4-ethylphenyl)vinyl]benzimidazole hydrochloride; 1-(5-ethoxy-2-pyridyl)-5-[(Z)-2-(4-ethylphenyl)vinyl]-benzimidazole hydrochloride; 5-[(E)-2-(4-tert-butylphenyl)vinyl]-1-(5-ethoxy-2-pyridyl)benzimidazole hydrochloride; 5-[(Z)-2-(4-tert-butylphenyl)vinyl]-1-(5-ethoxy-2-pyridyl)benzimidazole hydrochloride; 3-(4-ethoxyphenyl)-6-[(E)-2-(4-ethylphenyl)vinyl]imidazo[4,5-b]pyridine; 3-(4-ethoxyphenyl)-6-[(Z)-2-(4-ethylphenyl)vinyl]imidazo[4,5-b]pyridine; 6-[(E)-2-(4-isopropylphenyl)vinyl]-3-(4-methoxyphenyl)imidazo[4,5-b]pyridine; 6-[(Z)-2-(4-isopropylphenyl)vinyl]-3-(4-methoxyphenyl)imidazo[4,5-b]pyridine; 3-(4-ethoxyphenyl)-6-[2-(4-ethylphenyl)-ethynyl]imidazo[4,5-b]pyridine; 1-(4-ethoxyphenyl)-5-[2-(4-ethylphenyl)-ethyl]benzimidazole; 3-(4-ethoxyphenyl)-6-[2-(4-ethylphenyl)-ethyl]imidazo[4,5-b]pyridine; 1-(4-ethoxyphenyl)-5-[(4-ethylphenyl)-methoxy]benzimidazole; 5-[(4-isopropylphenyl)methoxy]-1-(4-methoxyphenyl)benzimidazole; 3-(4-ethoxyphenyl)-6-[(4-ethylphenyl)-methoxy]imidazo[4, 5-b]pyridine; 6-[(4-isopropyl-phenyl)methoxy]-3-(4-methoxyphenyl)imidazo[4,5-b]pyridine; 1-(4-ethoxyphenyl)-5-[(4-ethylphenyl)-methylsulfanyl]benzimidazole; N-[[1-(4-ethoxyphenyl)-benzimidazol-5-yl]methyl]-4-ethyl-aniline; 1-(4-ethoxyphenyl)-6-[2-(4-ethylphenyl)-ethyl]benzimidazole; 5-[2-(4-tert-butylphenyl)cyclopropyl]-1-(4-isopropoxyphenyl)-benzimidazole; methyl 4-[(Z)-2-[1-(4-isopropoxyphenyl)-benzimidazol-5-yl]vinyl]benzoate; 2-[4-[(Z)-2-[1-(4-isopropoxyphenyl)benzimidazol-5-yl]vinyl]phenyl]-propan-2-ol; 5-[(Z)-2-[4-(1-fluoro-1-methyl-ethyl)phenyl]vinyl]-1-(4-isopropoxyphenyl)benzimidazole; 5-[(Z)-2-(4-isopropenylphenyl)-vinyl]-1-(4-isopropoxyphenyl)-benzimidazole; 5-[4-[(Z)-2-[1-(4-isopropoxyphenyl)benzimidazol-5-yl]vinyl]phenyl]nonan-5-ol; 2-[4-[(Z)-2-[1-(5-isopropoxy-2-pyridyl)benzimidazol-5-yl]vinyl]phenyl]propan-2-ol; 1-(4-isopropoxyphenyl)-5-[(Z)-2-[4-(2,2,2-trifluoro-1,1-dimethyl-ethyl)phenyl]vinyl]benzimidazole; 3-[4-[(Z)-2-[1-(4-isopropoxyphenyl)benzimidazol-5-yl]vinyl]phenyl]propanal; 4-[(Z)-2-[1-(4-isopropoxyphenyl)benzimidazol-5-yl]vinyl]benzoic acid; 1,1,1-trifluoro-2-[4-[(Z)-2-[1-(4-isopropoxyphenyl)benzimidazol-5-yl]vinyl]phenyl]propan-2-ol; 1,1,1,3,3,3-hexafluoro-2-[4-[(Z)-2-[1-(4-isopropoxyphenyl)benzimidazol-5-yl]vinyl]phenyl]propan-2-ol; 1-[4-[(Z)-2-[1-(4-isopropoxyphenyl)benzimidazol-5-yl]vinyl]phenyl]cyclopropanol; 4-[(Z)-2-[1-(4-isopropoxyphenyl)benzimidazol-5-yl]vinyl]benzonitrile; 2-[4-[(Z)-2-[1-(4-isopropoxyphenyl)benzimidazol-5-yl]vinyl]phenyl]butan-2-ol; 1-[4-[(Z)-2-[1-(4-isopropoxyphenyl)benzimidazol-5-yl]vinyl]phenyl]ethanol; 1-[4-[(Z)-2-[1-(4-isopropoxyphenyl)benzimidazol-5-yl]vinyl]phenyl]cyclobutanol; 3-[4-[(Z)-2-[1-(4-isopropoxyphenyl)benzimidazol-5-yl]vinyl]phenyl]oxetan-3-ol; 1-[4-[(Z)-2-[1-(4-isopropoxyphenyl)benzimidazol-5-yl]vinyl]phenyl]cyclopropanamine; 2-hydroxy-2-[4-[(Z)-2-[1-(4-isopropoxyphenyl)benzimidazol-5-yl]vinyl]phenyl]propanoic acid; 1-[4-[(Z)-2-[1-(4-isopropoxyphenyl)benzimidazol-5-yl]vinyl]phenyl]cyclopentanol; 1-[4-[(Z)-2-[1-(4-isopropoxyphenyl)benzimidazol-5-yl]vinyl]phenyl]cyclohexanol; 3-[4-[(Z)-2-[1-(4-isopropoxyphenyl)benzimidazol-5-yl]vinyl]phenyl]azetidin-3-ol; 4-[4-[(Z)-2-[1-(4-isopropoxyphenyl)benzimidazol-5-yl]vinyl]phenyl]tetrahydropyran-4-ol; 2-[4-[(Z)-2-[1-(4-isopropoxyphenyl)benzimidazol-5-yl]vinyl]phenyl]propan-2-amine; and 2-[4-[(Z)-2-[1-(4-ethoxyphenyl)benzimidazol-5-yl]vinyl]phenyl]propan-2-ol shown below in Table 1.

More preferably, compounds of Formula I are selected from the group consisting of: 5-[(Z)-2-(4-tert-butylphenyl)vinyl]-1-(4-isopropoxyphenyl)-benzimidazole; 1-(4-ethoxyphenyl)-5-[(4-ethylphenyl)-methoxy]benzimidazole; and 2-[4-[(Z)-2-[1-(4-isopropoxyphenyl)benzimidazol-5-yl]vinyl]phenyl]-propan-2-ol.

TABLE 1

Compounds of the invention of Formula I

| Cmpd | Chemical Structure | Molecular Formula | Analytical Data | Chemical Name |
|---|---|---|---|---|
| 1 | 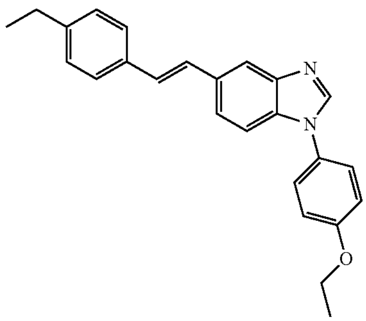 [SMILES: CCOc1ccc(-n2cnc3cc(/C=C/c4ccc(CC)cc4)ccc32)cc1] | $C_{25}H_{24}N_2O$ | 1H NMR in CDCl3: δ 8.04 (s, 1H), 7.96 (d, 1H), 7.53 (dd, 1H), 7.48 (d, 2H), 7.38-7.43 (m, 3H), 7.05-7.22 (m, 6H), 4.12 (q, 2H), 2.67 (q, 2H), 1.48 (t, 3H), 1.26 (t, 3H); 13C NMR in CDCl3: δ 158.7, 144.4, 143.7, 143.1, 135.0, 133.8, 132.7, 128.9, 128.2, 128.2, 127.6, 126.4, 125.6, 122.2, 118.4, 115.6, 110.4, 63.9, 28.6, 15.5, 14.8; Mass Spec: 369.3 (M + H)+ | 1-(4-ethoxyphenyl)-5-[(E)-2-(4-ethylphenyl)vinyl]benzimidazole |
| 2 | 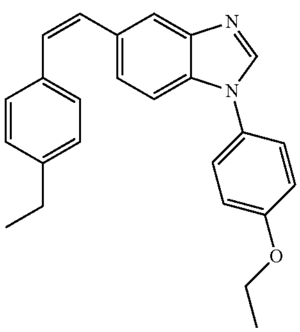 [SMILES: CCOc1ccc(-n2cnc3cc(/C=C\c4ccc(CC)cc4)ccc32)cc1] | $C_{25}H_{24}N_2O$ | 1H NMR in CDCl3: δ 8.01 (s, 1H), 7.78 (bs, 1H), 7.36-7.41 (m, 2H), 7.25-7.31 (m, 2H), 7.21 (d, 2H), 7.01-7.07 (m, 4H), 6.70 (d, 1H), 6.58 (d, 1H), 4.10 (q, 2H), 2.60 (q, 2H), 1.47 (t, 3H), 1.21 (t, 3H); 13C NMR in CDCl3: δ 158.7, 144.0, 143.1, 142.8, 134.7, 133.3, 132.2, 129.8, 129.5, 129.0, 128.8, 127.7, 125.5, 124.9, 120.6, 115.6, 109.9, 63.9, 28.6, 15.4, 14.8; Mass Spec: 369.0 (M + H)+ | 1-(4-ethoxyphenyl)-5-[(Z)-2-(4-ethylphenyl)vinyl]benzimidazole |
| 3 | 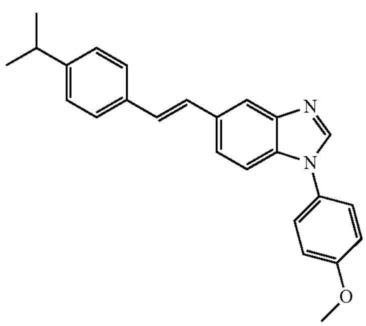 [SMILES: COc1ccc(-n2cnc3cc(/C=C/c4ccc(C(C)C)cc4)ccc32)cc1] | $C_{25}H_{24}N_2O$ | 1H NMR in CDCl3: δ 8.04 (s, 1H), 7.96 (s, 1H), 7.40-7.55 (m, 6H), 7.06-7.26 (m, 6H), 3.90 (s, 3H), 2.88-2.97 (m, 1H), 1.27 (d, 6H); 13C NMR in CDCl3: δ 159.4, 148.3, 144.4, 143.1, 135.2, 133.8, 132.7, 129.1, 128.2, 127.6, 126.7, 126.4, 125.6, 122.3, 118.4, 115.2, 110.4, 55.7, 33.9, 23.9; Mass Spec: 369.3 (M + H)+ | 5-[(E)-2-(4-isopropylphenyl)vinyl]-1-(4-methoxyphenyl)benzimidazole |
| 4 | 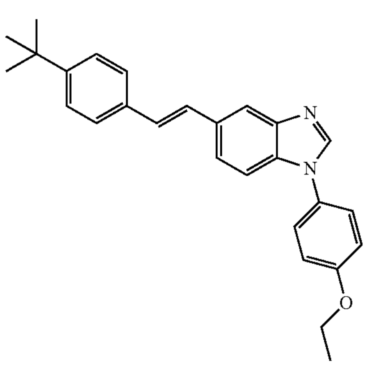 [SMILES: CCOc1ccc(-n2cnc3cc(/C=C/c4ccc(C(C)(C)C)cc4)ccc32)cc1] | $C_{27}H_{28}N_2O$ | 1H NMR in CDCl3: δ 8.04 (s, 1H), 7.96 (d, 1H), 7.48-7.54 (m, 3H), 7.38-7.43 (m, 5H), 7.15-7.27 (m, 2H), 7.04-7.10 (m, 2H), 4.12 (q, 2H), 1.48 (t, 3H), 1.34 (s, 9H); 13C NMR in CDCl3: δ 158.7, 150.5, 144.4, 143.1, 134.8, 133.9, 132.7, 128.9, 128.4, 127.5, 126.1, 125.6, 125.6, 122.3, 118.4, 115.6, 110.4, 63.9, 34.6, 31.3, 14.8; Mass Spec: 397.2 (M + H)+ | 5-[(E)-2-(4-tert-butylphenyl)vinyl]-1-(4-ethoxyphenyl)-benzimidazole |

TABLE 1-continued

Compounds of the invention of Formula I

| Cmpd | Chemical Structure | Molecular Formula | Analytical Data | Chemical Name |
|------|-------------------|-------------------|-----------------|---------------|
| 5 | 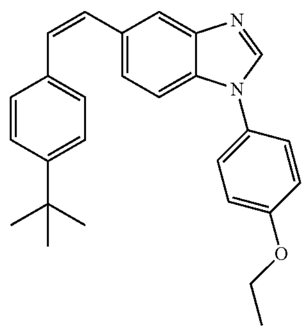 [SMILES: CCOc1ccc(-n2cnc3cc(/C=C\c4ccc(C(C)(C)C)cc4)ccc32)cc1] | $C_{27}H_{28}N_2O$ | 1H NMR in CDCl3: δ 8.01 (s, 1H), 7.81 (s, 1H), 7.37-7.41 (m, 2H), 7.24-7.32 (m, 2H), 7.23 (m, 4H), 7.02-7.07 (m, 2H), 6.71 (d, 1H), 6.56 (d, 1H), 4.10 (q, 2H), 1.47 (t, 3H), 1.28 (s, 9H); 13C NMR in CDCl3: δ 158.7, 150.0, 144.0, 142.8, 134.3, 133.3, 132.3, 129.8, 129.4, 129.0, 128.6, 125.5, 125.1, 124.9, 120.6, 115.6, 110.0, 63.9, 34.5, 31.3, 14.8; Mass Spec: 397.2 (M + H)+ | 5-[(Z)-2-(4-tert-butylphenyl)vinyl]-1-(4-ethoxyphenyl) benzimidazole |
| 6 | 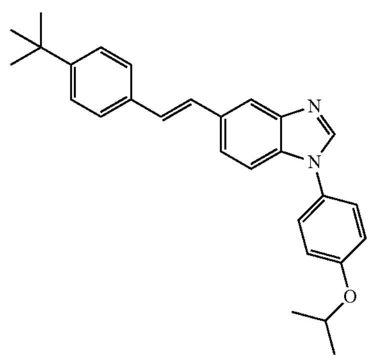 [SMILES: CC(C)Oc1ccc(-n2cnc3cc(/C=C/c4ccc(C(C)(C)C)cc4)ccc32)cc1] | $C_{28}H_{30}N_2O$ | 1H NMR in CDCl3: δ 8.04 (s, 1H), 7.96 (s, 1H), 7.38-7.55 (m, 8H), 7.15-7.7.27 (m, 2H), 7.04-7.08 (m, 2H), 4.61-4.65 (m, 1H), 1.41 (d, 6H), 1.34 (s, 9H); Mass Spec: 411.0 (M + H)+ | 5-[(E)-2-(4-tert-butylphenyl)vinyl]-1-(4-isopropoxyphenyl)-benzimidazole |
| 7 | 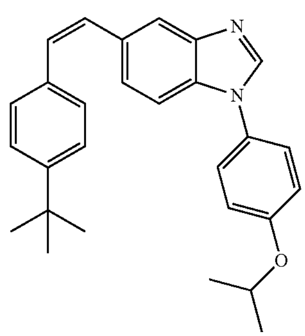 [SMILES: CC(C)Oc1ccc(-n2cnc3cc(/C=C\c4ccc(C(C)(C)C)cc4)ccc32)cc1] | $C_{28}H_{30}N_2O$ | 1H NMR in CDCl3: δ 8.01 (s, 1H), 7.81 (d, 1H), 7.36-7.40 (m, 2H), 7.18-7.33 (m, 6H), 7.01-7.05 (m, 2H), 6.71 (d, 1H), 6.56 (d, 1H), 4.59-4.63 (m, 1H), 1.39 (d, 6H), 1.29 (s, 9H); 13C NMR in CDCl3: δ 157.7, 150.0, 144.0, 142.9, 134.3, 133.3, 132.3, 129.8, 129.4, 128.8, 128.6, 125.6, 125.1, 124.9, 120.6, 116.8, 110.0, 70.4, 34.5, 31.3, 22.0; Mass Spec: 411.0 (M + H)+ | 5-[(Z)-2-(4-tert-butylphenyl)vinyl]-1-(4-isopropoxyphenyl)-benzimidazole |
| 8 | 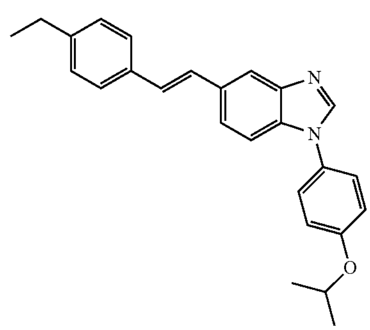 [SMILES: CCc1ccc(/C=C/c2ccc3c(c2)ncn3-c2ccc(OC(C)C)cc2)cc1] | $C_{26}H_{26}N_2O$ | 1H NMR in CDCl3: δ 8.04 (s, 1H), 7.96 (d, 1H), 7.37-7.54 (m, 6H), 7.04-7.22 (m, 6H), 4.59-4.65 (m, 1H), 2.67 (q, 2H), 1.41 (d, 6H), 1.26 (t, 3H); Mass Spec: 383.1 (M + H)+ | 5-[(E)-2-(4-ethylphenyl)vinyl]-1-(4-isopropoxyphenyl)-benzimidazole |

TABLE 1-continued

Compounds of the invention of Formula I

| Cmpd | Chemical Structure | Molecular Formula | Analytical Data | Chemical Name |
|---|---|---|---|---|
| 9 | 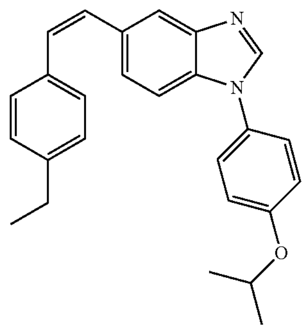 [SMILES: CCc1ccc(/C=C\c2ccc3c(c2)ncn3-c2ccc(OC(C)C)cc2)cc1] | $C_{26}H_{26}N_2O$ | 1H NMR in CDCl3: δ 8.01 (s, 1H), 7.78 (d, 1H), 7.35-7.40 (m, 2H), 7.19-7.31 (m, 4H), 7.02-7.05 (m, 4H), 6.71 (d, 1H), 6.58 (d, 1H), 4.57-4.63 (m, 1H), 2.60 (q, 2H), 1.39 (d, 6H), 1.21 (t, 3H); 13C NMR in CDCl3: δ 157.7, 144.0, 143.1, 142.9, 134.7, 133.3, 132.2, 129.8, 129.5, 128.8, 127.7, 125.5, 124.9, 120.6, 116.8, 109.9, 70.4, 28.6, 22.0, 15.4; Mass Spec: 383.1 (M + H)+ | 5-[(Z)-2-(4-ethylphenyl)vinyl]-1-(4-isopropoxyphenyl)-benzimidazole |
| 10 | 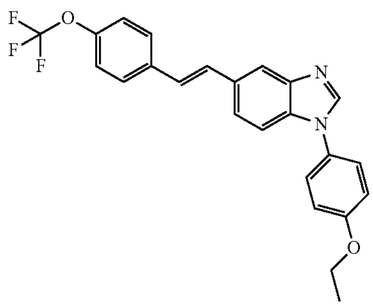 [SMILES: CCOc1ccc(-n2cnc3cc(/C=C/c4ccc(OC(F)(F)F)cc4)ccc32)cc1] | $C_{24}H_{19}F_3N_2O_2$ | 1H NMR in CDCl3: δ 8.06 (s, 1H), 7.98 (s, 1H), 7.51-7.58 (m, 3H), 7.39-7.45 (m, 3H), 7.21-7.28 (m, 3H), 7.05-7.14 (m, 3H), 4.13 (q, 2H), 1.49 (t, 3H); Mass Spec: 425.1 (M + H)+ | 1-(4-ethoxyphenyl)-5-[(E)-2-[4-(trifluoromethoxy)phenyl]vinyl]benzimidazole |
| 11 | 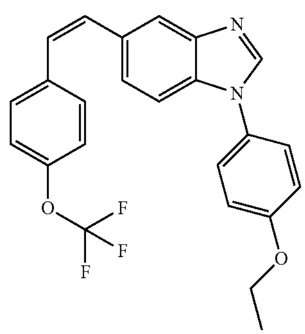 [SMILES: CCOc1ccc(-n2cnc3cc(/C=C\c4ccc(OC(F)(F)F)cc4)ccc32)cc1] | $C_{24}H_{19}F_3N_2O_2$ | 1H NMR in CDCl3: δ 8.02 (s, 1H), 7.75 (d, 1H), 7.36-7.41 (m, 2H), 7.27-7.32 (m, 4H), 7.18 (dd, 1H), 7.03-7.08 (m, 3H), 6.80 (d, 1H), 6.56 (d, 1H), 4.10 (q, 2H), 1.47 (t, 3H); 13C NMR in CDCl3: δ 158.8, 148.0, 144.0, 143.1, 136.0, 133.5, 131.5, 131.4, 130.3, 128.8, 127.9, 125.6, 124.7, 120.7, 120.6, 115.6, 110.2, 63.9, 14.8; Mass Spec: 425.1 (M + H)+ | 1-(4-ethoxyphenyl)-5-[(Z)-2-[4-(trifluoromethoxy)phenyl]vinyl]benzimidazole |
| 12 | 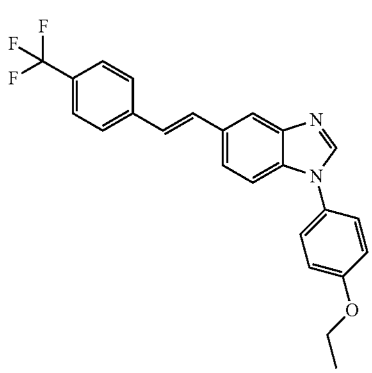 [SMILES: CCOc1ccc(-n2cnc3cc(/C=C/c4ccc(C(F)(F)F)cc4)ccc32)cc1] | $C_{24}H_{19}F_3N_2O$ | 1H NMR in CDCl3: δ 8.07 (s, 1H), 8.00 (s, 1H), 7.59-7.66 (m, 4H), 7.55 (d, 1H), 7.33-7.46 (m, 4H), 7.06-7.18 (m, 3H), 4.13 (q, 2H), 1.49 (t, 3H); Mass Spec: 409.2 (M + H)+ | 1-(4-ethoxyphenyl)-5-[(E)-2-[4-(trifluoromethyl)phenyl]vinyl]benzimidazole |

TABLE 1-continued

Compounds of the invention of Formula I

| Cmpd | Chemical Structure | Molecular Formula | Analytical Data | Chemical Name |
|---|---|---|---|---|
| 13 | 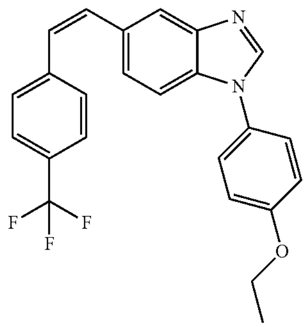 [SMILES: CCOc1ccc(-n2cnc3cc(/C=C\c4ccc(C(F)(F)F)cc4)ccc32)cc1] | $C_{24}H_{19}F_3N_2O$ | 1H NMR in CDCl3: δ 8.03 (s, 1H), 7.74 (s, 1H), 7.26-7.47 (m, 7H), 7.16 (d, 1H), 7.03-7.08 (m, 2H), 6.87 (d, 1H), 6.61 (d, 1H), 4.11 (q, 2H), 1.47 (t, 3H); 13C NMR in CDCl3: δ 158.8, 144.0, 143.1, 133.7, 132.6, 131.3, 129.2, 128.8, 128.0, 125.6, 125.2, 125.2, 125.1, 125.1, 124.7, 120.8, 115.6, 110.2, 63.9, 14.8; Mass Spec: 409.2 (M + H)+ | 1-(4-ethoxyphenyl)-5-[(Z)-2-[4-trifluoromethyl)phenyl]vinyl]benzimidazole |
| 14 | 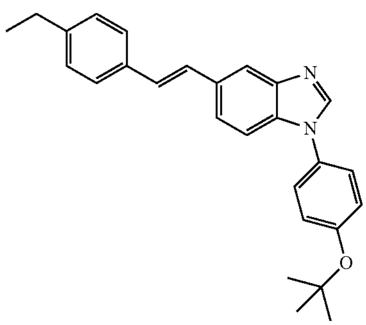 [SMILES: CCc1ccc(/C=C/c2ccc3c(c2)ncn3-c2ccc(OC(C)(C)C)cc2)cc1] | $C_{27}H_{28}N_2O$ | 1H NMR in CDCl3: δ 8.07 (s, 1H), 7.97 (d, 1H), 7.46-7.55 (m, 4H), 7.38-7.42 (m, 2H), 7.10-7.22 (m, 6H), 2.67 (q, 2H), 1.43 (s, 9H), 1.26 (t, 3H); 13C NMR in CDCl3: δ 155.4, 144.5, 143.7, 143.0, 135.0, 133.6, 132.8, 131.4, 128.2, 128.2, 127.7, 126.4, 125.2, 124.7, 122.3, 118.4, 110.5, 79.4, 28.9, 28.6, 15.5; Mass Spec: 397.2 (M + H)+ | 1-(4-tert-butoxyphenyl)-5-[(E)-2-(4-ethylphenyl)-vinyl]benzimidazole |
| 15 | 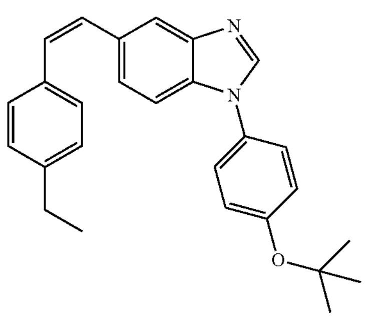 [SMILES: CCc1ccc(/C=C\c2ccc3c(c2)ncn3-c2ccc(OC(C)(C)C)cc2)cc1] | $C_{27}H_{28}N_2O$ | 1H NMR in CDCl3: δ 8.04 (s, 1H), 7.79 (d, 1H), 7.33-7.40 (m, 3H), 7.14-7.27 (m, 5H), 7.04 (d, 2H), 6.71 (d, 1H), 6.58 (d, 1H), 2.60 (q, 2H), 1.41 (s, 9H), 1.21 (t, 3H); 13C NMR in CDCl3: δ 155.3, 144.1, 143.1, 142.7, 134.6, 133.0, 132.4, 131.4, 129.7, 129.6, 128.8, 127.7, 125.2, 125.0, 124.6, 120.7, 110.0, 79.4, 28.8, 28.6, 15.3; Mass Spec: 397.2 (M + H)+ | 1-(4-tert-butoxyphenyl)-5-[(Z)-2-(4-ethylphenyl)-vinyl]benzimidazole |
| 16 | 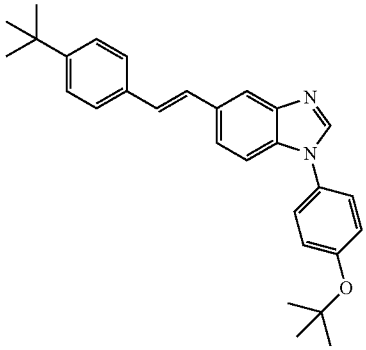 [SMILES: CC(C)(C)Oc1ccc(-n2cnc3cc(/C=C/c4ccc(C(C)(C)C)cc4)ccc32)cc1] | $C_{29}H_{32}N_2O$ | 1H NMR in CDCl3: δ 8.07 (s, 1H), 7.97 (s, 1H), 7.46-7.55 (m, 4H), 7.38-7.42 (m, 4H), 7.10-7.27 (m, 4H), 1.43 (s, 9H), 1.34 (s, 9H); 13C NMR in CDCl3: δ 155.4, 150.5, 144.5, 143.0, 134.8, 133.6, 132.8, 131.4, 128.3, 127.6, 126.1, 125.6, 125.2, 124.7, 122.3, 118.4, 110.5, 79.4, 34.6, 31.3, 28.9; Mass Spec: 425.1 (M + H)+ | 1-(4-tert-butoxyphenyl)-5-[(E)-2-(4-tert-butylphenyl)vinyl]benzimidazole |

TABLE 1-continued

Compounds of the invention of Formula I

| Cmpd | Chemical Structure | Molecular Formula | Analytical Data | Chemical Name |
|---|---|---|---|---|
| 17 | 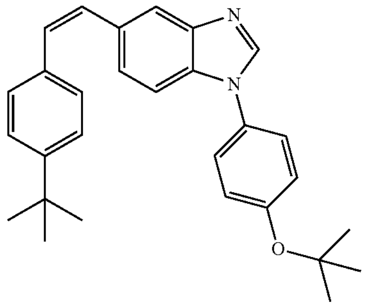 [SMILES: CC(C)(C)Oc1ccc(-n2cnc3cc(/C=C\c4ccc(C(C)(C)C)cc4)ccc32)cc1] | $C_{29}H_{32}N_2O$ | 1H NMR in CDCl3: δ 8.05 (s, 1H), 7.81 (d, 1H), 7.35-7.41 (m, 3H), 7.28 (dd, 1H), 7.23 (s, 4H), 7.14-7.19 (m, 2H), 6.71 (d, 1H), 6.56 (d, 1H), 1.42 (s, 9H), 1.29 (s, 9H); 13C NMR in CDCl3: δ 155.3, 150.0, 144.1, 142.7, 134.3, 133.0, 132.4, 131.4, 129.7, 129.4, 128.6, 125.2, 125.1, 125.0, 124.6, 120.6, 110.0, 79.4, 34.5, 31.3, 28.8; Mass Spec: 425.1 (M + H)+ | 1-(4-tert-butoxyphenyl)-5-[(Z)-2-(4-tert-butylphenyl)vinyl]benzimidazole |
| 18 | 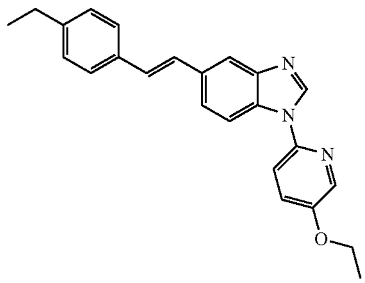 [SMILES: CCOc1ccc(-n2cnc3cc(/C=C/c4ccc(CC)cc4)ccc32)nc1] | $C_{24}H_{23}N_3O \cdot HCl$ | 1H NMR in DMSO-d6: δ 9.61 (s, 1H), 8.40 (d, 1H), 8.21 (d, 1H), 8.02 (d, 1H), 7.96 (d, 1H), 7.83 (dd, 1H), 7.78 (dd, 1H), 7.57 (d, 2H), 7.38 (d, 2H), 7.25 (d, 2H), 4.23 (q, 2H), 2.63 (q, 2H), 1.41 (t, 3H), 1.20 (t, 3H); 13C NMR in DMSO-d6: δ 155.0, 144.0, 142.4, 141.9, 136.7, 135.1, 134.9, 130.6, 129.4, 128.6, 127.5, 127.0, 125.3, 124.3, 117.5, 115.2, 115.0, 64.8, 28.4, 16.0, 15.0; Mass Spec: 370.2 (M + H − HCl)+ | 1-(5-ethoxy-2-pyridyl)-5-[(E)-2-(4-ethylphenyl)vinyl]benzimidazole hydrochloride |
| 19 | 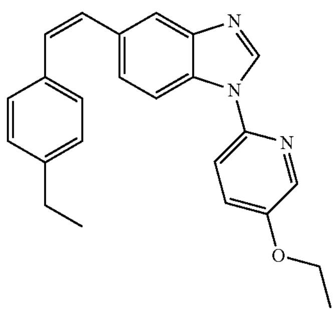 [SMILES: CCOc1ccc(-n2cnc3cc(/C=C\c4ccc(CC)cc4)ccc32)nc1] | $C_{24}H_{23}N_3O \cdot HCl$ | 1H NMR in DMSO-d6: δ 9.68 (s, 1H), 8.37 (d, 1H), 8.11 (d, 1H), 7.95 (d, 1H), 7.77 (dd, 1H), 7.71 (s, 1H), 7.41 (dd, 1H), 7.13 (q, 4H), 6.74 (ABq, 2H), 4.22 (q, 2H), 2.57 (q, 2H), 1.40 (t, 3H), 1.16 (t, 3H); 13C NMR in DMSO-d6: δ 155.1, 143.5, 142.2, 141.7, 136.9, 136.7, 134.8, 134.3, 131.1, 130.2, 129.1, 129.0, 128.3, 126.9, 125.2, 117.7, 116.8, 114.8, 64.9, 28.3, 15.8, 14.9; Mass Spec: 370.2 (M + H − HCl)+ | 1-(5-ethoxy-2-pyridyl)-5-[(Z)-2-(4-ethylphenyl)vinyl]benzimidazol hydrochloride |
| 20 | 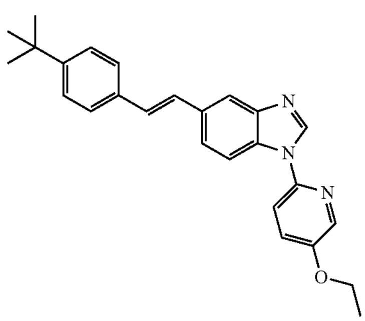 [SMILES: CCOc1ccc(-n2cnc3cc(/C=C/c4ccc(C(C)(C)C)cc4)ccc32)nc1] | $C_{26}H_{27}N_3O \cdot HCl$ | 1H NMR in DMSO-d6: δ 9.48 (s, 1H), 8.39 (d, 1H), 8.20 (d, 1H), 8.01 (d, 1H), 7.95 (d, 1H), 7.74-7.82 (m, 2H), 7.58 (d, 2H), 7.36-7.43 (m, 4H), 4.23 (q, 2H), 1.40 (t, 3H), 1.30 (s, 9H); 13C NMR in DMSO-d6: δ 154.8, 150.8, 142.6, 142.1, 136.7, 134.7, 130.9, 129.0, 127.7, 126.7, 126.0, 125.3, 117.3, 115.7, 114.8, 64.8, 34.8, 31.5, 15.0; Mass Spec: 398.1 (M + H − HCl)+ | 5-[(E)-2-(4-tert-butylphenyl)vinyl]-1-(5-ethoxy-2-pyridyl)benzimidazole hydrochloride |
| 21 | 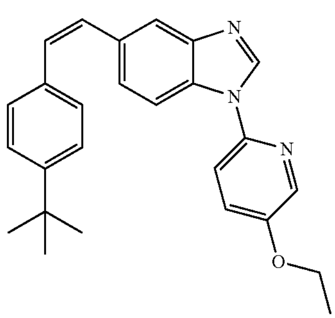 [SMILES: CCOc1ccc(-n2cnc3cc(/C=C\c4ccc(C(C)(C)C)cc4)ccc32)nc1] | $C_{26}H_{27}N_3O \cdot HCl$ | 1H NMR in DMSO-d6: δ 9.59 (s, 1H), 8.36 (d, 1H), 8.11 (d, 1H), 7.94 (d, 1H), 7.76 (dd, 1H), 7.72 (s, 1H), 7.42 (d, 1H), 7.28 (d, 2H), 7.18 (d, 2H), 6.73 (ABq, 2H), 4.22 (q, 2H), 1.39 (t, 3H), 1.25 (s, 9H); 13C NMR in DMSO-d6: δ 155.0, 150.4, 142.3, 141.9, 136.7, 134.6, 134.0, 130.8, 130.3, 129.3, 128.8, 126.7, 125.6, 125.3, 117.6, 117.1, 114.7, 64.8, 34.8, 31.5, 14.9; Mass Spec: 398.1 (M + H − HCl)+ | 5-[(Z)-2-(4-tert-butylphenyl)vinyl]-1-(5-ethoxy-2-pyridyl)benzimidazole hydrochloride |

TABLE 1-continued

Compounds of the invention of Formula I

| Cmpd | Chemical Structure | Molecular Formula | Analytical Data | Chemical Name |
|---|---|---|---|---|
| 22 | 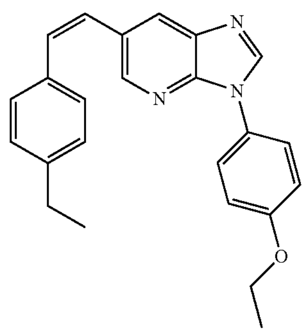 [SMILES: CCOc1ccc(-n2cnc3cc(/C=C\c4ccc(CC)cc4)cnc32)cc1] | $C_{24}H_{23}N_3O$ | 1H NMR in CDCl3: δ 8.35 (d, 1H), 8.21 (s, 1H), 8.03 (d, 1H), 7.56-7.61 (m, 2H), 7.16-7.18 (m, 2H), 7.03-7.09 (m, 4H), 6.72 (d, 1H), 6.65 (d, 1H), 4.10 (q, 2H), 2.60 (q, 2H), 1.46 (t, 3H), 1.22 (t, 3H); 13C NMR in CDCl3: δ 158.6, 146.1, 143.7, 143.6, 135.5, 134.0, 131.6, 128.9, 128.7, 128.0, 127.9, 127.8, 126.2, 125.2, 115.5, 63.9, 28.6, 15.3, 14.8; Mass Spec: 370.2 (M + H)+ | 3-(4-ethoxyphenyl)-6-[(Z)-2-(4-ethylphenyl)vinyl]imidazo[4,5-b]pyridine |
| 23 | 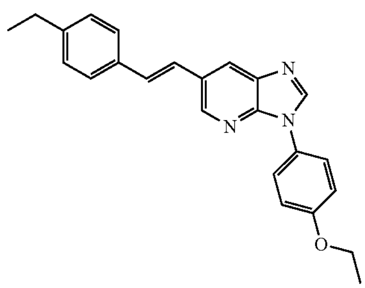 [SMILES: CCOc1ccc(-n2cnc3cc(/C=C/c4ccc(CC)cc4)cnc32)cc1] | $C_{24}H_{23}N_3O$ | 1H NMR in CDCl3: δ 8.56 (d, 1H), 8.27 (d, 1H), 8.25 (s, 1H), 7.60-7.63 (m, 2H), 7.49 (d, 2H), 7.18-7.25 (m, 4H), 7.06-7.09 (m, 2H), 4.11 (q, 2H), 2.67 (q, 2H), 1.47 (t, 3H), 1.26 (t, 3H); 13C NMR in CDCl3: δ 158.7, 144.6, 144.2, 144.0, 136.0, 134.5, 129.4, 129.4, 128.3, 127.8, 126.5, 125.2, 124.6, 124.4, 115.6, 63.9, 28.7, 15.5, 14.8; Mass Spec: 370.2 (M + H)+ | 3-(4-ethoxyphenyl)-6-[(E)-2-(4-ethylphenyl)vinyl]imidazo[4,5-b]pyridine |
| 24 | 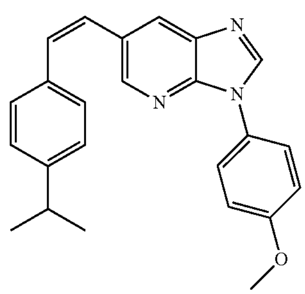 [SMILES: COc1ccc(-n2cnc3cc(/C=C\c4ccc(C(C)C)cc4)cnc32)cc1] | $C_{24}H_{23}N_3O$ | 1H NMR in CDCl3: δ 8.37 (d, 1H), 8.22 (s, 1H), 8.05 (d, 1H), 7.58-7.63 (m, 2H), 7.17-7.20 (m, 2H), 7.05-7.10 (m, 4H), 6.71 (d, 1H), 6.65 (d, 1H), 3.87 (s, 3H), 2.82-2.86 (m, 1H), 1.22 (d, 6H); 13C NMR in CDCl3: δ 159.3, 148.2, 146.1, 145.9, 143.6, 135.4, 134.1, 131.6, 128.9, 128.7, 127.9, 126.6, 126.1, 125.3, 115.0, 55.6, 33.8, 23.9; Mass Spec: 370.2 (M + H)+ | 6-[(Z)-2-(4-isopropylphenyl)vinyl]-3-(4-methoxyphenyl)imidazo[4,5-b]pyridine |
| 25 | 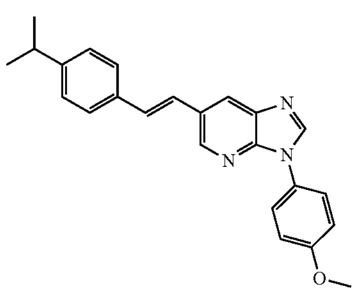 [SMILES: COc1ccc(-n2cnc3cc(/C=C/c4ccc(C(C)C)cc4)cnc32)cc1] | $C_{24}H_{23}N_3O$ | 1H NMR in CDCl3: δ 8.56 (d, 1H), 8.27 (d, 1H), 8.26 (s, 1H), 7.60-7.65 (m, 2H), 7.47-7.51 (m, 2H), 7.24-7.27 (m, 2H), 7.19 (d, 2H), 7.07-7.13 (m, 2H), 3.89 (s, 3H), 2.88-2.97 (m, 1H), 1.28 (d, 6H); 13C NMR in CDCl3: δ 159.3, 148.9, 146.6, 144.6, 144.0, 136.0, 134.6, 129.4, 128.0, 126.8, 126.5, 125.2, 124.6, 124.4, 115.0, 55.6, 33.9, 23.9; Mass Spec: 370.2 (M + H)+ | 6-[(E)-2-(4-isopropylphenyl)vinyl]-3-(4-methoxyphenyl)imidazo[4,5-b]pyridine |
| 26 | 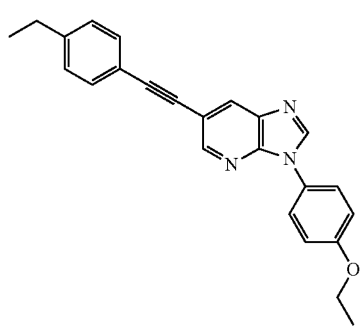 [SMILES: CCOc1ccc(-n2cnc3cc(C#Cc4ccc(CC)cc4)cnc32)cc1] | $C_{24}H_{21}N_3O$ | Mass Spec: 368.1 (M + H)+ | 3-(4-ethoxyphenyl)-6-[2-(4-ethylphenyl)ethynyl]imidazo[4,5-b]pyridine |

TABLE 1-continued

Compounds of the invention of Formula I

| Cmpd | Chemical Structure | Molecular Formula | Analytical Data | Chemical Name |
|---|---|---|---|---|
| 27 | 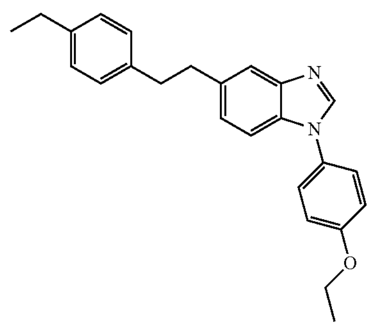 [SMILES: CCOc1ccc(-n2cnc3cc(CCc4ccc(CC)cc4)ccc32)cc1] | $C_{25}H_{26}N_2O$ | 1H NMR in CDCl3: δ 8.04 (s, 1H), 7.66 (bs, 1H), 7.35-7.42 (m, 3H), 7.10-7.17 (m, 5H), 7.02-7.08 (m, 2H), 4.11 (q, 2H), 2.92-3.09 (m, 4H), 2.63 (q, 2H), 1.47 (t, 3H), 1.23 (t, 3H); 13C NMR in CDCl3: δ 158.7, 144.0, 142.6, 141.8, 139.0, 136.7, 132.6, 129.1, 129.0, 128.4, 128.1, 127.8, 125.6, 124.5, 119.6, 115.6, 110.0, 63.9, 38.2, 38.1, 28.5, 15.7, 14.8; Mass Spec: 371.1 (M + H)+ | 1-(4-ethoxyphenyl)-5-[2-(4-ethylphenyl)-ethyl]benzimidazole |
| 28 | 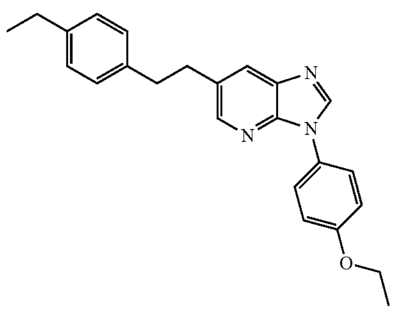 [SMILES: CCOc1ccc(-n2cnc3cc(CCc4ccc(CC)cc4)cnc32)cc1] | $C_{24}H_{25}N_3O$ | 1H NMR in CDCl3: δ 8.25 (d, 1H), 8.23 (s, 1H), 7.92 (d, 1H), 7.57-7.62 (m, 2H), 7.11 (s, 4H), 7.04-7.09 (m, 2H), 4.10 (q, 2H), 3.05-3.11 (m, 2H), 2.93-2.99 (m, 2H), 2.62 (q, 2H), 1.46 (t, 3H), 1.23 (t, 3H); 13C NMR in CDCl3: δ 158.6, 145.7, 145.6, 143.4, 142.0, 138.1, 135.6, 132.5, 128.4, 127.9, 127.8, 125.2, 115.5, 63.9, 37.8, 35.1, 28.4, 15.6, 14.8; Mass Spec: 372.3 (M + H)+ | 3-(4-ethoxyphenyl)-6-[2-(4-ethylphenyl)-ethyl]imidazo[4,5-b]pyridine |
| 29 | 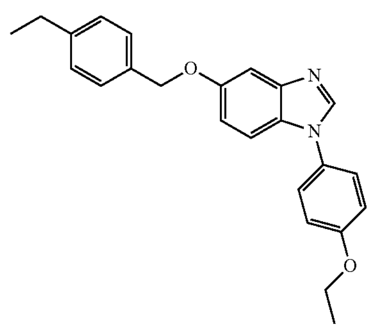 [SMILES: CCOc1ccc(-n2cnc3cc(OCc4ccc(CC)cc4)ccc32)cc1] | $C_{24}H_{24}N_2O_2$ | 1H NMR in CDCl3: δ 7.99 (s, 1H), 7.32-7.41 (m, 6H), 7.22 (d, 2H), 7.01-7.07 (m, 3H), 5.11 (s, 2H), 4.10 (q, 2H), 2.66 (q, 2H), 1.47 (t, 3H), 1.24 (t, 3H); 13C NMR in CDCl3: δ 158.6, 155.5, 144.6, 144.1, 142.6, 134.3, 129.1, 129.0, 128.1, 127.8, 125.4, 115.6, 114.4, 110.8, 103.8, 70.7, 63.9, 28.6, 15.6, 14.8; Mass Spec: 373.2 (M + H)+ | 1-(4-ethoxyphenyl)-5-[(4-ethylphenyl)-methoxy]benzimidazole |
| 30 | 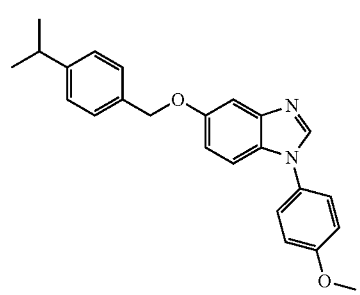 [SMILES: COc1ccc(-n2cnc3cc(OCc4ccc(C(C)C)cc4)ccc32)cc1] | $C_{24}H_{24}N_2O_2$ | 1H NMR in CDCl3: δ 7.98 (s, 1H), 7.37-7.42 (m, 5H), 7.33 (d, 1H), 7.24-7.26 (m, 2H), 7.01-7.08 (m, 3H), 5.11 (s, 2H), 3.88 (s, 3H), 2.87-2.96 (m, 1H), 1.26 (d, 6H); 13C NMR in CDCl3: δ 159.2, 155.6, 148.7, 144.6, 142.6, 134.5, 129.3, 129.0, 127.8, 126.7, 125.5, 115.1, 114.4, 110.7, 103.8, 70.7, 55.6, 33.9, 24.0; Mass Spec: 373.2 (M + H)+ | 5-[(4-isopropylphenyl)methoxy]-1-(4-methoxyphenyl)benzimidazole |

TABLE 1-continued

Compounds of the invention of Formula I

| Cmpd | Chemical Structure | Molecular Formula | Analytical Data | Chemical Name |
|---|---|---|---|---|
| 31 | 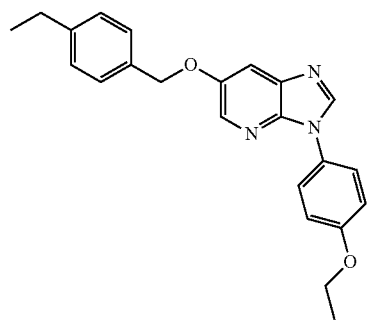 [SMILES: CCOc1ccc(-n2cnc3cc(OCc4ccc(CC)cc4)cnc32)cc1] | $C_{23}H_{23}N_3O_2$ | 1H NMR in CDCl3: δ 8.27 (d, 1H), 8.19 (s, 1H), 7.69 (d, 1H), 7.56-7.61 (m, 2H), 7.39 (d, 2H), 7.23 (d, 2H), 7.03-7.08 (m, 2H), 5.13 (s, 2H), 4.09 (m, 2H), 2.66 (q, 2H), 1.46 (t, 3H), 1.24 (t, 3H); 13C NMR in CDCl3: δ 158.6, 152.6, 144.4, 143.5, 141.9, 136.3, 136.0, 133.5, 128.2, 128.0, 127.8, 125.1, 115.5, 112.4, 71.3, 63.9, 28.6, 15.6, 14.8; Mass Spec: 374.1 (M + H)+ | 3-(4-ethoxyphenyl)-6-[(4-ethylphenyl)-methoxy]imidazo[4,5-b]pyridine |
| 32 | 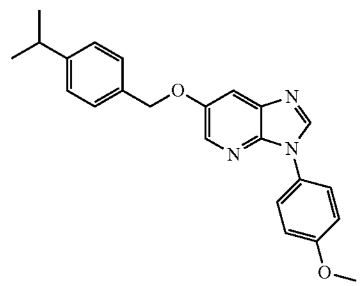 [SMILES: COc1ccc(-n2cnc3cc(OCc4ccc(C(C)C)cc4)cnc32)cc1] | $C_{23}H_{23}N_3O_2$ | 1H NMR in CDCl3: δ 8.27 (d, 1H), 8.20 (s, 1H), 7.70 (d, 1H), 7.57-7.63 (m, 2H), 7.40 (d, 2H), 7.26 (d, 2H), 7.05-7.10 (m, 2H), 5.13 (s, 2H), 3.87 (s, 3H), 2.88-2.97 (m, 1H), 1.26 (d, 6H); 13C NMR in CDCl3: δ 159.2, 152.7, 149.1, 143.5, 136.3, 136.0, 133.7, 128.1, 127.8, 126.8, 125.1, 115.0, 112.4, 71.3, 55.6, 33.9, 24.0; Mass Spec: 374.1 (M + H)+ | 6-[(4-isopropyl-phenyl)methoxy]-3-(4-methoxyphenyl)imidazo[4,5-b]pyridine |
| 33 | 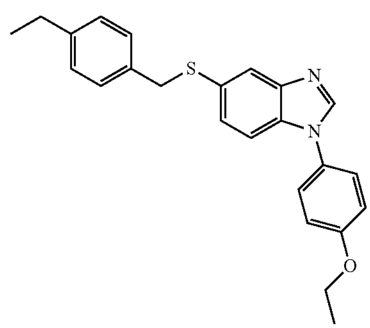 [SMILES: CCOc1ccc(-n2cnc3cc(SCc4ccc(CC)cc4)ccc32)cc1] | $C_{24}H_{24}N_2OS$ | 1H NMR in CDCl3: δ 8.02 (s, 1H), 7.88 (bs, 1H), 7.35-7.39 (m, 2H), 7.27-7.32 (m, 2H), 7.20 (d, 2H), 7.04-7.11 (m, 4H), 4.07-4.14 (m, 4H), 2.61 (q, 2H), 1.47 (t, 3H), 1.21 (t, 3H); 13C NMR in CDCl3: δ 158.8, 144.4, 143.1, 134.9, 133.4, 129.7, 128.8, 128.7, 127.9, 127.3, 125.6, 123.3, 115.6, 110.6, 63.9, 40.6, 28.5, 15.5, 14.8; Mass Spec: 389.1 (M + H)+ | 1-(4-ethoxyphenyl)-5-[(4-ethylphenyl)-methylsulfanyl]benzimidazole |
| 34 | 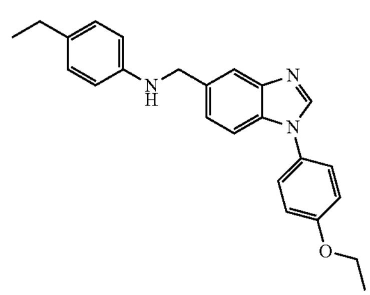 [SMILES: CCOc1ccc(-n2cnc3cc(CNc4ccc(CC)cc4)ccc32)cc1] | $C_{24}H_{25}N_3O$ | 1H NMR in CDCl3: δ 8.03 (s, 1H), 7.85 (s, 1H), 7.32-7.42 (m, 4H), 6.98-7.07 (m, 4H), 6.60-6.64 (m, 2H), 4.45 (s, 2H), 4.11 (q, 2H), 3.99 (bs, 1H), 2.53 (q, 2H), 1.47 (t, 3H), 1.18 (t, 3H); Mass Spec: 372.0 (M + H)+ | N-[[1-(4-ethoxyphenyl)benzimidazol-5-yl]methyl]-4-ethyl-aniline |
| 35 | 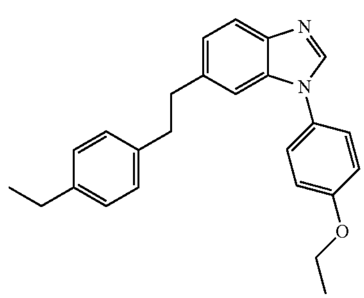 [SMILES: CCOc1ccc(-n2cnc3ccc(CCc4ccc(CC)cc4)cc32)cc1] | $C_{25}H_{26}N_2O$ | 1H NMR in CDCl3: δ 7.99 (s, 1H), 7.77 (d, 1H), 7.31-7.36 (m, 2H), 7.16-7.20 (m, 2H), 7.02-7.13 (m, 6H), 4.11 (q, 2H), 2.99-3.05 (m, 2H), 2.88-2.94 (m, 2H), 2.63 (q, 2H), 1.48 (t, 3H), 1.23 (t, 3H); 13C NMR in CDCl3: δ 158.6, 142.3, 141.8, 138.9, 137.7, 129.1, 128.5, 127.8, 125.7, 123.6, 120.1, 115.6, 109.8, 63.9, 38.4, 38.1, 28.4, 15.7, 14.8; Mass Spec: 371.1 (M + H)+ | 1-(4-ethoxyphenyl)-6-[2-(4-ethylphenyl)-ethyl]benzimidazole |

TABLE 1-continued

Compounds of the invention of Formula I

| Cmpd | Chemical Structure | Molecular Formula | Analytical Data | Chemical Name |
|------|-------------------|-------------------|-----------------|---------------|
| 36 | 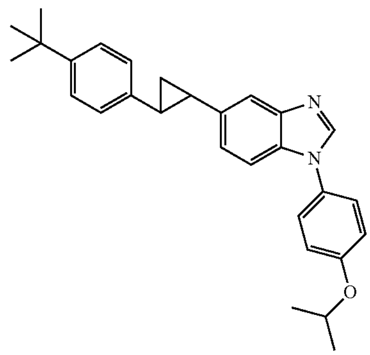 [SMILES: CC(C)Oc1ccc(-n2cnc3cc(C4CC4c4ccc(C(C)(C)C)cc4)ccc32)cc1] | $C_{29}H_{32}N_2O$ | 1H NMR in CDCl3: δ 8.01 (s, 1H), 7.60 (s, 1H), 7.31-7.40 (m, 5H), 7.08-7.16 (m, 3H), 7.01-7.06 (m, 2H), 4.57-4.63 (m, 1H), 2.29-2.35 (m, 1H), 2.16-2.22 (m, 1H), 1.43-1.53 (m, 2H), 1.40 (d, 6H), 1.32 (s, 9H); 13C NMR in CDCl3: δ 157.6, 148.6, 144.3, 142.7, 139.7, 137.4, 132.7, 129.0, 125.5, 125.5, 125.3, 122.6, 116.8, 110.1, 70.4, 34.4, 31.4, 28.0, 27.7, 22.0, 18.2; Mass Spec: 425.4 (M + H)+ | 5-[2-(4-tert-butylphenyl) cyclopropyl]-1-(4-isopropoxyphenyl)-benzimidazole |
| 37 | 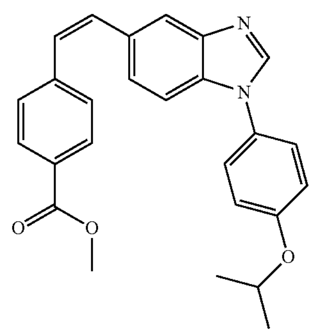 [SMILES: COC(=O)c1ccc(/C=C\c2ccc3c(c2)ncn3-c2ccc(OC(C)C)cc2)cc1] | $C_{26}H_{24}N_2O_3$ | 1H NMR in CDCl3: δ 8.02 (s, 1H), 7.87 (d, 2H), 7.73 (s, 1H), 7.27-7.40 (m, 5H), 7.16 (dd, 1H), 7.03 (d, 2H), 6.87 (d, 1H), 6.63 (d, 1H), 4.57-4.65 (m, 1H), 3.88 (s, 3H), 1.39 (d, 6H); 13C NMR in CDCl3: δ 166.9, 157.7, 144.0, 143.1, 142.4, 133.6, 132.6, 131.4, 129.6, 128.9, 128.7, 128.5, 128.4, 125.6, 124.8, 120.9, 116.9, 110.1, 70.4, 52.0, 22.0; Mass Spec: 413.1 (M + H)+ | methyl4-[(Z)-2-[1-(4-isopropoxyphenyl)-benzimidazol-5-yl]vinyl]benzoate |
| 38 | 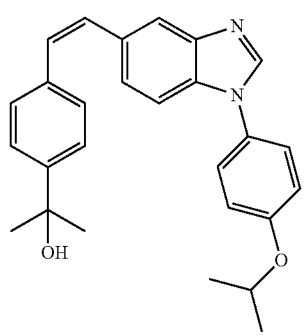 [SMILES: CC(C)Oc1ccc(-n2cnc3cc(/C=C\c4ccc(C(C)(C)O)cc4)ccc32)cc1] | $C_{27}H_{28}N_2O_2$ | 1H NMR in CDCl3: δ 8.00 (s, 1H), 7.78 (s, 1H), 7.38 (d, 2H), 7.22-7.35 (m, 6H), 7.03 (d, 2H), 6.74 (d, 1H), 6.58 (d, 1H), 4.57-4.65 (m, 1H), 1.56 (s, 6H), 1.39 (d, 6H); 13C NMR in CDCl3: δ 157.7, 147.9, 144.0, 142.9, 135.8, 133.4, 132.1, 130.4, 129.1, 128.8, 125.6, 124.9, 124.3, 120.6, 116.8, 110.0, 72.4, 70.4, 31.6, 22.0; Mass Spec: 413.1 (M + H)+ | 2-[4-[(Z)-2-[1-(4-isopropoxyphenyl) benzimidazol-5-yl]vinyl]phenyl]-propan-2-ol |
| 39 | 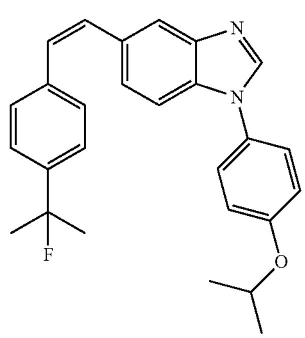 [SMILES: CC(C)Oc1ccc(-n2cnc3cc(/C=C\c4ccc(C(C)(C)F)cc4)ccc32)cc1] | $C_{27}H_{27}FN_2O$ | 1H NMR in CDCl3: δ 8.04 (s, 1H), 7.78 (s, 1H), 7.38 (d, 2H), 7.20-7.32 (m, 6H), 7.037 (d, 2H), 6.76 (d, 1H), 6.58 (d, 1H), 4.57-4.63 (m, 1H), 1.70 (s, 3H), 1.62 (s, 3H), 1.39 (d, 6H); 13C NMR in CDCl3: δ 157.7, 142.9, 132.1, 130.6, 129.0, 128.8, 128.7, 125.6, 124.9, 123.8, 123.7, 120.5, 116.8, 110.1, 70.4, 29.3, 29.0, 22.0; Mass Spec: 395.1 (M − HF)+ | 5-[(Z)-2-[4-(1-fluoro-1-methyl-ethyl)phenyl]vinyl]-1-(4-isopropoxy-phenyl) benzimidazole |

TABLE 1-continued

Compounds of the invention of Formula I

| Cmpd | Chemical Structure | Molecular Formula | Analytical Data | Chemical Name |
|------|--------------------|-------------------|-----------------|---------------|
| 40 | 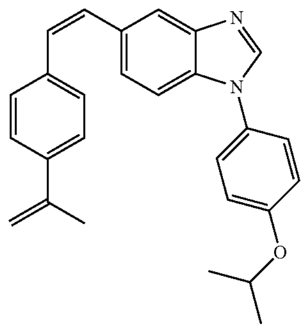 [SMILES: C=C(C)c1ccc(/C=C\c2ccc3c(c2)ncn3-c2ccc(OC(C)C)cc2)cc1] | $C_{27}H_{26}N_2O$ | 1H NMR in CDCl3: δ 8.06 (s, 1H), 7.79 (s, 1H), 7.23-7.40 (m, 8H), 7.03 (d, 2H), 6.75 (d, 1H), 6.59 (d, 1H), 5.36 (s, 1H), 5.05 (s, 1H), 4.57-4.65 (m, 1H), 2.12 (s, 3H), 1.39 (d, 6H); 13C NMR in CDCl3: δ 157.8, 142.8, 142.8, 139.7, 136.5, 132.3, 130.4, 129.3, 128.8, 128.6, 126.3, 125.6, 125.3, 125.0, 120.5, 116.9, 112.2, 110.1, 70.4, 22.0, 21.7; Mass Spec: 395.1 (M + H)+ | 5-[(Z)-2-(4-isopropenylphenyl)-vinyl]-1-(4-isopropoxyphenyl)-benzimidazole |
| 41 | 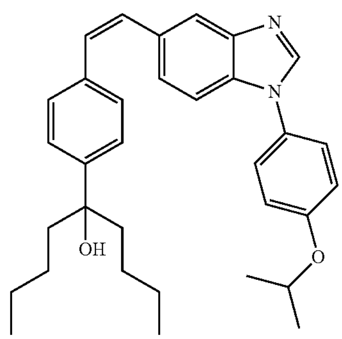 [SMILES: CCCCC(O)(CCCC)c1ccc(/C=C\c2ccc3c(c2)ncn3-c2ccc(OC(C)C)cc2)cc1] | $C_{33}H_{40}N_2O_2$ | 1H NMR in CDCl3: δ 9.34 (s, 1H). 7.99 (s, 1H), 7.51 (d, 2H), 7.40 (dd, 1H), 7.32 (d, 1H), 7.24 (d, 2H), 7.08-7.14 (m, 4H), 6.77 (d, 1H), 6.69 (d, 1H), 4.60-4.66 (m, 1H), 1.71-1.78 (m, 4H), 1.40 (d, 6H), 1.18-1.28 (m, 6H), 1.03-1.09 (m, 2H), 0.79-0.84 (m, 6H); 13C NMR in CDCl3: δ 159.7, 146.5, 138.9, 137.4, 134.3, 132.5, 131.8, 130.5, 128.5, 128.3, 128.0, 126.2, 125.6, 125.3, 117.2, 116.5, 111.8, 70.7, 42.3, 25.7, 23.1, 21.9, 14.0; Mass Spec: 497.4 (M + H)+ | 5-[4-[(Z)-2-[1-(4-isopropoxyphenyl) benzimidazol-5-yl]vinyl]phenyl] nonan-5-ol |
| 42 | 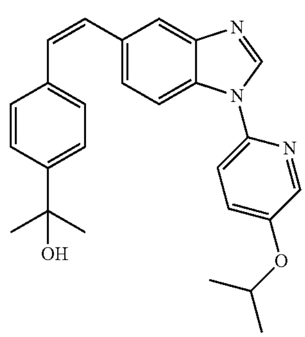 [SMILES: CC(C)Oc1ccc(-n2cnc3cc(/C=C\c4ccc(C(C)(C)O)cc4)ccc32)nc1] | $C_{26}H_{27}N_3O_2$ | 1H NMR in CDCl3: δ 8.40 (s, 1H), 8.23-8.25 (m, 1H), 7.76-7.78 (m, 2H), 7.45 (d, 1H), 7.39 (dd, 1H), 7.24-7.34 (m, 5H), 6.74 (d, 1H), 6.59 (d, 1H), 4.61-4.65 (m, 1H), 1.56 (s, 6H), 1.41 (d, 6H); 13C NMR in CDCl3: δ 153.0, 147.9, 144.5, 142.7, 141.7, 137.9, 135.7, 132.5, 131.5, 130.3, 129.3, 128.8, 125.6, 125.3, 124.3, 120.7, 115.4, 111.7, 72.4, 71.3, 31.6, 21.9; Mass Spec: 414.3 (M + H)+ | 2-[4-[(Z)-2-[1-(5-isopropoxy-2-pyridyl)benzimidazol-5-yl]vinyl] phenyl]propan-2-ol |
| 43 | 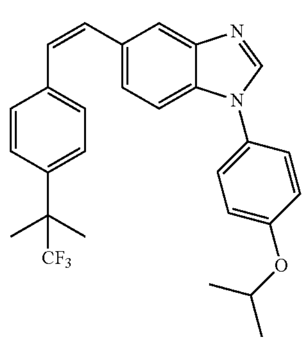 [SMILES: CC(C)Oc1ccc(-n2cnc3cc(/C=C\c4ccc(C(C)(C)C(F)(F)F)cc4)ccc32)cc1] | $C_{28}H_{27}F_3N_2O$ | 1H NMR in CDCl3: δ 8.02 (s, 1H), 7.79 (s, 1H), 7.22-7.41 (m, 8H), 7.04 (dd, 2H), 6.77 (d, 1H), 6.57 (d, 1H), 4.59-4.63 (m, 1H), 1.54 (s, 6H), 1.40 (d, 6H); ); 13C NMR in CDCl3: δ 157.7, 144.0, 143.0, 138.6, 136.6, 133.4, 131.9, 130.9, 130.2, 128.7, 128.7, 127.2, 126.5, 125.6, 124.8, 120.6, 116.9, 110.1, 70.4, 43.8, 43.5, 22.6, 22.5, 22.0; Mass Spec: 465.3 (M + H)+ | 1-(4-isopropoxyphenyl)-5-[(Z)-2-[4-(2,2,2-trifluoro-1,1-dimethyl-ethyl)phenyl]vinyl] benzimidazole |

TABLE 1-continued

Compounds of the invention of Formula I

| Cmpd | Chemical Structure | Molecular Formula | Analytical Data | Chemical Name |
|---|---|---|---|---|
| 44 | 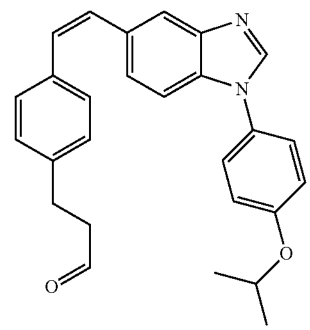 [SMILES: CC(C)Oc1ccc(-n2cnc3cc(/C=C\c4ccc(CCC=O)cc4)ccc32)cc1] | $C_{27}H_{26}N_2O_2$ | Mass Spec: 411.3 (M + H)+ | 3-[4-[(Z)-2-[1-(4-isopropoxyphenyl)benzimidazol-5-yl]vinyl]phenyl]propanal |
| 45 | 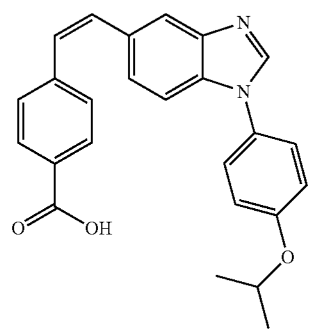 [SMILES: CC(C)Oc1ccc(-n2cnc3cc(/C=C\c4ccc(C(=O)O)cc4)ccc32)cc1] | $C_{25}H_{22}N_2O_3$ | 1H NMR in CDCl3: δ 8.13 (s, 1H), 7.95 (d, 2H), 7.88 (s, 1H), 7.32-7.40 (m, 5H), 7.20 (dd, 1H), 7.01-7.07 (m, 2H), 6.83 (d, 1H), 6.65 (d, 1H), 4.57-4.65 (m, 1H), 1.39 (d, 6H); ); 13C NMR in CDCl3: δ 169.6, 157.9, 143.0, 142.4, 132.1, 131.6, 130.1, 128.8, 128.8, 128.7, 128.4, 125.7, 125.5, 120.3, 116.9, 110.4, 70.4, 27.0, 22.0; Mass Spec: 399.3 (M + H)+ | 4-[(Z)-2-[1-(4-isopropoxyphenyl)benzimidazol-5-yl]vinyl]benzoic acid |
| 46 | 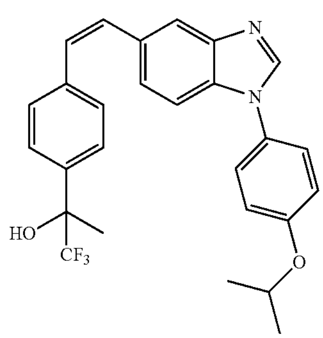 [SMILES: CC(C)Oc1ccc(-n2cnc3cc(/C=C\c4ccc(C(C)(O)C(F)(F)F)cc4)ccc32)cc1] | $C_{27}H_{25}F_3N_2O_2$ | 1H NMR in CDCl3: δ 8.01 (s, 1H), 7.75 (s, 1H), 7.20-7.43 (m, 8H), 7.02-7.06 (m, 2H), 6.78 (d, 1H), 6.59 (d, 1H), 4.57-4.65 (m, 1H), 2.88 (s, 1H), 1.75 (s, 3H), 1.39 (d, 6H); 13C NMR in CDCl3: δ 174.2, 157.7, 143.8, 143.0, 137.7, 137.2, 131.8, 131.2, 128.8, 128.7, 126.0, 125.6, 124.9, 120.6, 116.9, 110.1, 70.4, 23.8, 22.0; Mass Spec: 467.1 (M + H)+ | 1,1,1-trifluoro-2-[4-[(Z)-2-[1-(4-isopropoxyphenyl)benzimidazol-5-yl]vinyl]phenyl]propan-2-ol |
| 47 | 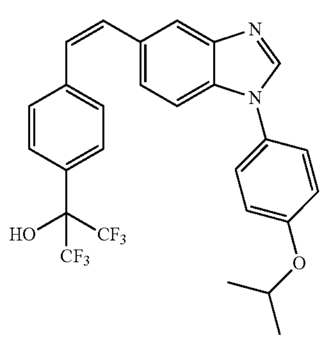 [SMILES: CC(C)Oc1ccc(-n2cnc3cc(/C=C\c4ccc(C(O)(C(F)(F)F)C(F)(F)F)cc4)ccc32)cc1] | $C_{27}H_{22}F_6N_2O_2$ | 1H NMR in CDCl3: δ 7.99 (s, 1H), 7.62 (s, 2H), 7.59 (s, 1H), 7.29-7.39 (m, 5H), 7.20 (dd, 1H), 7.02-7.06 (m, 2H), 6.87 (bs, 1H), 6.77 (d, 1H), 6.58 (d, 1H), 4.57-4.65 (m, 1H), 1.39 (d, 6H); Mass Spec: 521.1 (M + H)+ | 1,1,1,3,3,3-hexafluoro-2-[4-[(Z)-2-[1-(4-isopropoxyphenyl)benzimidazol-5-yl]vinyl]phenyl]propan-2-ol |

TABLE 1-continued

Compounds of the invention of Formula I

| Cmpd | Chemical Structure | Molecular Formula | Analytical Data | Chemical Name |
|---|---|---|---|---|
| 48 | 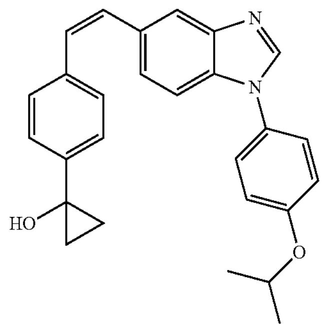 [SMILES: CC(C)Oc1ccc(-n2cnc3cc(/C=C\c4ccc(C5(O)CC5)cc4)ccc32)cc1] | $C_{27}H_{26}N_2O_2$ | 1H NMR in CDCl3: δ 8.02 (s, 1H), 7.76 (s, 1H), 7.22-7.40 (m, 6H), 7.14-7.16 (m, 2H), 7.03-7.06 (m, 2H), 6.75 (d, 1H), 6.60 (d, 1H), 4.58-4.64 (m, 1H), 1.40 (d, 6H), 1.23-1.27 (m, 2H), 1.01-1.05 (m, 2H); Mass Spec: 411.3 (M + H)+ | 1-[4-[(Z)-2-[1-(4-isopropoxyphenyl) benzimidazol-5-yl]vinyl]phenyl] cyclopropanol |
| 49 | 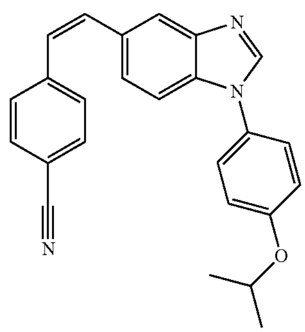 [SMILES: CC(C)Oc1ccc(-n2cnc3cc(/C=C\c4ccc(C#N)cc4)ccc32)cc1] | $C_{25}H_{21}N_3O$ | 1H NMR in CDCl3: δ 8.03 (s, 1H), 7.71 (s, 1H), 7.48 (dd, 2H), 7.26-7.40 (m, 5H), 7.12 (dd, 1H), 7.02-7.06 (m, 2H), 6.91 (d, 1H), 6.58 (d, 1H), 4.57-4.65 (m, 1H), 1.39 (d, 6H); 13C NMR in CDCl3: δ 157.8, 144.1, 143.3, 142.4, 133.8, 133.7, 132.1, 130.9, 129.6, 128.6, 127.7, 125.6, 124.7, 120.8, 119.0, 116.9, 110.4, 110.3, 70.5, 22.0; Mass Spec: 380.1 (M + H)+ | 4-[(Z)-2-[1-(4-isopropoxyphenyl) benzimidazol-5-yl]vinyl]benzonitrile |
| 50 | 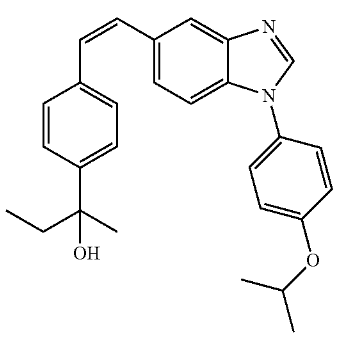 [SMILES: CCC(C)(O)c1ccc(/C=C\c2ccc3c(c2)ncn3-c2ccc(OC(C)C)cc2)cc1] | $C_{28}H_{30}N_2O_2$ | 1H NMR in CDCl3: δ 8.00 (s, 1H), 7.77 (s, 1H), 7.36-7.39 (m, 2H), 7.21-7.31 (m, 6H), 7.02-7.05 (m, 2H), 6.73 (d, 1H), 6.58 (d, 1H); ); 13C NMR in CDCl3: δ 157.7, 146.6, 143.9, 142.9, 135.6, 133.4, 132.1, 130.3, 129.2, 128.8, 128.7, 125.6, 124.9, 124.8, 120.6, 116.9, 110.0, 74.8, 70.4, 36.6, 29.4, 22.0, 8.4; Mass Spec: 427.2 (M + H)+ | 2-[4-[(Z)-2-[1-(4-isopropoxyphenyl) benzimidazol-5-yl]vinyl]phenyl] butan-2-ol |
| 51 | 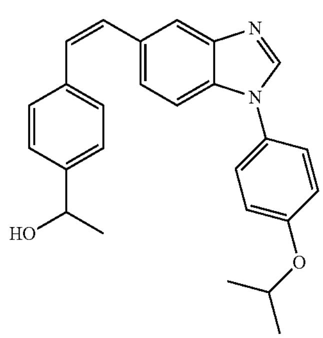 [SMILES: CC(C)Oc1ccc(-n2cnc3cc(/C=C\c4ccc(C(C)O)cc4)ccc32)cc1] | $C_{26}H_{26}N_2O_2$ | 1H NMR in CDCl3: δ 7.99 (s, 1H), 7.74 (s, 1H), 7.34-7.39 (m, 2H), 7.20-7.31 (m, 6H), 7.00-7.06 (m, 2H), 7.74 (d, 1H), 6.59 (d, 1H); ); 13C NMR in CDCl3: δ 157.7, 144.6, 143.9, 142.9, 136.6, 133.4, 132.0, 130.5, 129.2, 129.0, 128.7, 125.6, 125.4, 124.9, 120.6, 116.9, 110.0, 70.4, 70.2, 24.9, 22.0; Mass Spec: 399.3 (M + H)+ | 1-[4-[(Z)-2-[1-(4-isopropoxyphenyl) benzimidazol-5-yl]vinyl] phenyl]ethanol |

TABLE 1-continued

Compounds of the invention of Formula I

| Cmpd | Chemical Structure | Molecular Formula | Analytical Data | Chemical Name |
|---|---|---|---|---|
| 52 | 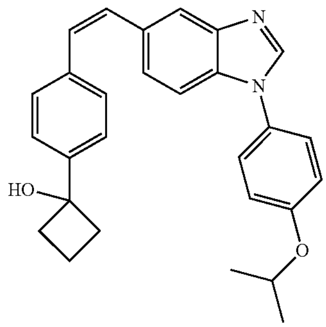 [SMILES: CC(C)Oc1ccc(-n2cnc3cc(/C=C\c4ccc(C5(O)CCC5)cc4)ccc32)cc1] | $C_{28}H_{28}N_2O_2$ | 1H NMR in CDCl3: δ 7.99 (s, 1H), 7.76 (s, 1H), 7.21-7.40 (m, 8H), 7.00-7.05 (m, 2H), 6.75 (d, 1H), 6.59 (d, 1H), 4.57-4.65 (m, 1H), 2.48-2.58 (m, 2H), 2.29-2.39 (m, 2H), 2.19 (s, 1H), 1.95-2.07 (m, 1H), 1.63-1.75 (m, 1H), 1.39 (d, 6H); 13C NMR in CDCl3: δ 157.7, 145.1, 143.9, 142.9, 136.4, 133.4, 132.0, 130.6, 129.1, 129.0, 128.8, 125.6, 124.9, 120.7, 116.9, 110.1, 70.4, 36.8, 22.0, 13.0; Mass Spec: 425.1 (M + H)+ | 1-[4-[(Z)-2-[1-(4-isopropoxyphenyl)benzimidazol-5-yl]vinyl]phenyl]cyclobutanol |
| 53 | 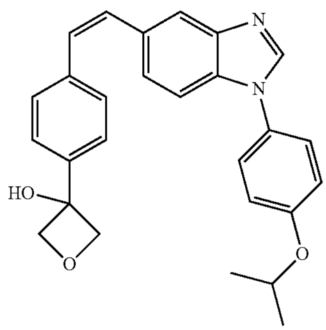 [SMILES: CC(C)Oc1ccc(-n2cnc3cc(/C=C\c4ccc(C5(O)COC5)cc4)ccc32)cc1] | $C_{27}H_{26}N_2O_3$ | 1H NMR in CDCl3: δ 7.95 (s, 1H), 7.69 (s, 1H), 7.43-7.46 (m, 2H), 7.28-7.38 (m, 5H), 7.21 (dd, 1H), 7.00-7.05 (m, 2H), 6.75 (d, 1H), 6.61 (d, 1H), 4.81-4.87 (m, 4H), 4.56-4.64 (m, 1H), 1.39 (d, 6H); 13C NMR in CDCl3: δ 157.9, 143.7, 143.1, 141.8, 137.1, 133.6, 132.1, 131.1, 129.3, 129.2, 128.8, 125.8, 125.3, 124.8, 120.6, 117.1, 110.4, 85.9, 75.6, 70.7, 22.4; Mass Spec: 427.2 (M + H)+ | 3-[4-[(Z)-2-[1-(4-isopropoxyphenyl)benzimidazol-5-yl]vinyl]phenyl]oxetan-3-ol |
| 54 | 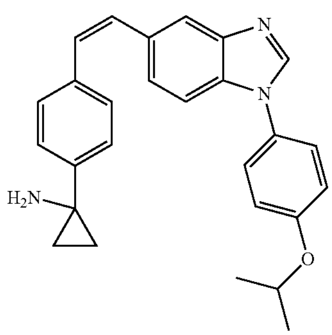 [SMILES: CC(C)Oc1ccc(-n2cnc3cc(/C=C\c4ccc(C5(N)CC5)cc4)ccc32)cc1] | $C_{27}H_{27}N_3O$ | 1H NMR in CDCl3: δ 8.00 (s, 1H), 7.77 (s, 1H), 7.34-7.39 (m, 2H), 7.21-7.31 (m, 4H), 7.10-7.12 (m, 2H), 7.00-7.06 (m, 2H), 6.72 (d, 1H), 6.56 (d, 1H), 4.56-4.64 (m, 1H), 1.39 (d, 6H), 1.01-1.06 (m, 2H), 0.93-0.98 (m, 2H); ); 13C NMR in CDCl3: δ 157.7, 145.7, 143.9, 142.9, 135.0, 133.4, 132.1, 130.2, 129.1, 128.9, 128.8, 125.5, 125.1, 124.9, 120.6, 116.8, 110.0, 72.5, 70.4, 61.6, 36.5, 22.0, 18.0; Mass Spec: 410.1 (M + H)+ | 1-[4-[(Z)-2-[1-(4-isopropoxyphenyl)benzimidazol-5-yl]vinyl]phenyl]cyclopropanamine |
| 55 | 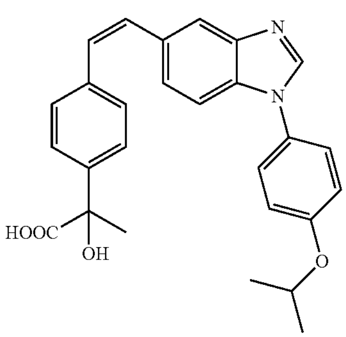 [SMILES: CC(C)Oc1ccc(-n2cnc3cc(/C=C\c4ccc(C(C)(O)C(=O)O)cc4)ccc32)cc1] | $C_{27}H_{26}N_2O_4$ | 1H NMR in CDCl3: δ 8.03 (s, 1H), 7.54 (s, 1H), 7.39 (d, 2H), 7.08-7.30 (m, 6H), 6.98 (d, 2H), 6.63 (d, 1H), 6.52 (d, 1H), 4.54-4.62 (m, 1H), 1.69 (s, 3H), 1.37 (d, 6H); Mass Spec: 443.1 (M + H)+ | 2-hydroxy-2-[4-[(Z)-2-[1-(4-isopropoxyphenyl)benzimidazol-5-yl]vinyl]phenyl]propanoic acid |

TABLE 1-continued

Compounds of the invention of Formula I

| Cmpd | Chemical Structure | Molecular Formula | Analytical Data | Chemical Name |
|---|---|---|---|---|
| 56 | 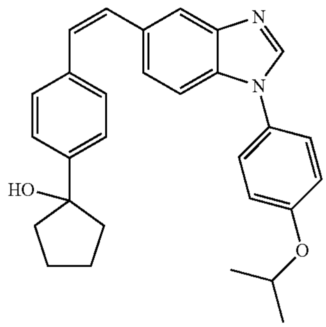 [SMILES: CC(C)Oc1ccc(-n2cnc3cc(/C=C\c4ccc(C5(O)CCCC5)cc4)ccc32)cc1] | $C_{29}H_{30}N_2O_2$ | 1H NMR in CDCl3: δ 8.00 (s, 1H), 7.77 (s, 1H), 7.22-7.40 (m, 8H), 7.00-7.06 (m, 2H), 6.74 (d, 1H), 6.58 (d, 1H), 4.57-4.65 (m, 1H), 1.97 (s, 6H), 1.81-1.95 (m, 2H), 1.39 (d, 6H); 13C NMR in CDCl3: δ 157.7, 145.9, 143.9, 142.9, 135.9, 133.4, 132.1, 130.4, 129.2, 128.8, 125.6, 125.0, 124.9, 120.6, 116.9, 110.1, 83.4, 70.4, 41.7, 23.8, 22.0; Mass Spec: 439.2 (M + H)+ | 1-[4-[(Z)-2-[1-(4-isopropoxyphenyl)benzimidazol-5-yl]vinyl]phenyl]cyclopentanol |
| 57 | 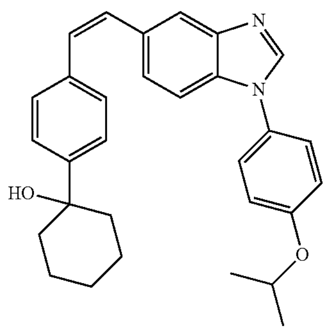 [SMILES: CC(C)Oc1ccc(-n2cnc3cc(/C=C\c4ccc(C5(O)CCCCC5)cc4)ccc32)cc1] | $C_{30}H_{32}N_2O_2$ | 1H NMR in CDCl3: δ 8.00 (s, 1H), 7.77 (s, 1H), 7.22-7.39 (m, 8H), 7.01-7.05 (m, 2H), 6.73 (d, 1H), 6.58 (d, 1H), 4.59-4.63 (m, 1H), 1.59-1.81 (m, 10H), 1.39 (d, 6H); 13C NMR in CDCl3: δ 157.7, 148.2, 143.9, 142.9, 135.8, 133.4, 132.1, 130.3, 129.2, 128.8, 125.6, 124.9, 124.5, 120.6, 116.9, 110.0, 73.0, 70.4, 38.7, 25.5, 22.2, 22.0; Mass Spec: 453.3 (M + H)+ | 1-[4-[(Z)-2-[1-(4-isopropoxyphenyl)benzimidazol-5-yl]vinyl]phenyl]cyclohexanol |
| 58 | 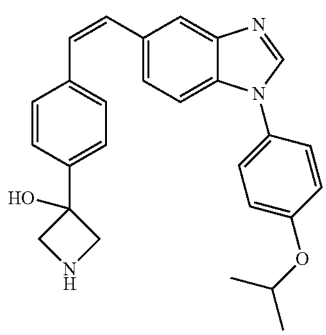 [SMILES: CC(C)Oc1ccc(-n2cnc3cc(/C=C\c4ccc(C5(O)CNC5)cc4)ccc32)cc1] | $C_{27}H_{27}N_3O_2$ | 1H NMR in CDCl3: δ 7.94 (s, 1H), 7.51 (s, 1H), 7.29-7.35 (m, 5H), 7.19-7.25 (m, 3H), 7.01 (d, 2H), 6.71 (d, 1H), 6.54 (d, 1H), 4.55-4.63 (m, 1H), 4.31 (d, 2H), 4.11 (d, 2H), 1.38 (d, 6H); Mass Spec: 426.3 (M + H)+ | 3-[4-[(Z)-2-[1-(4-isopropoxyphenyl)benzimidazol-5-yl]vinyl]phenyl]azetidin-3-ol |
| 59 | 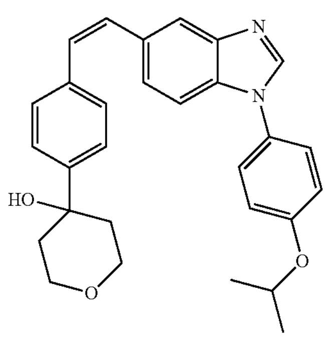 | $C_{29}H_{30}N_2O_3$ | 1H NMR in CDCl3: δ 7.99 (s, 1H), 7.75 (s, 1H), 7.21-7.39 (m, 8H), 7.01-7.06 (m, 2H), 6.75 (d, 1H), 6.58 (d, 1H), 4.57-4.65 (m, 1H), 3.81-3.96 (m, 4H), 2.04-2.19 (m, 2H), 1.70 (s, 2H), 1.39 (d, 6H); 13C NMR in CDCl3: δ 157.7, 146.9, 143.9, 142.9, 136.4, 133.4, 132.0, 130.7, 129.0, 129.0, 128.7, 125.6, 125.0, 124.5, 120.5, 116.9, 110.1, 70.5, 70.5, 63.9, 38.7, 22.0; Mass Spec: 455.4 (M + H)+ | 4-[4-[(Z)-2-[1-(4-isopropoxyphenyl)benzimidazol-5-yl]vinyl]phenyl]tetrahydropyran-4-ol |

TABLE 1-continued

Compounds of the invention of Formula I

| Cmpd | Chemical Structure | Molecular Formula | Analytical Data | Chemical Name |
|------|--------------------|-------------------|-----------------|---------------|
| 60 | 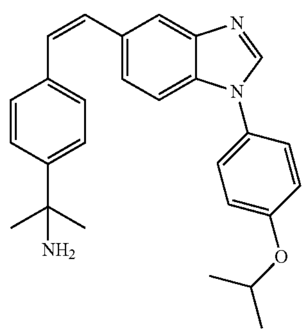 [SMILES: CC(C)Oc1ccc(-n2cnc3cc(/C=C\c4ccc(C(C)(C)N)cc4)ccc32)cc1] | $C_{27}H_{29}N_3O$ | 1H NMR in CDCl3: δ 7.97 (s, 1H), 7.77 (s, 1H), 7.22-7.40 (m, 8H), 7.00-7.06 (m, 2H), 6.73 (d, 1H), 6.56 (d, 1H), 4.57-4.65 (m, 1H), 1.50 (s, 6H), 1.39 (d, 6H); ); 13C NMR in CDCl3: δ 157.7, 143.9, 142.9, 135.5, 133.4, 132.1, 130.3, 129.1, 128.8, 125.6, 125.0, 124.7, 120.6, 116.9, 110.1, 70.4, 52.8, 32.0, 22.0; Mass Spec: 434.4 (M + Na)+ | 2-[4-[(Z)-2-[1-(4-isopropoxyphenyl)benzimidazol-5-yl]vinyl]phenyl]propan-2-amine |
| 61 | 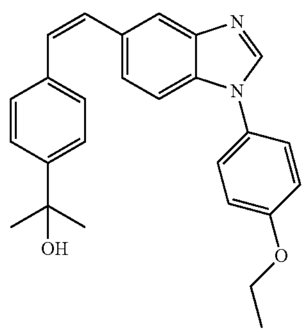 [SMILES: CCOc1ccc(-n2cnc3cc(/C=C\c4ccc(C(C)(C)O)cc4)ccc32)cc1] | $C_{26}H_{26}N_2O_2$ | 1H NMR in CDCl3: δ 8.01 (s, 1H), 7.78 (s, 1H), 7.23-7.42 (m, 8H), 7.03-7.08 (m, 2H), 6.75 (d, 1H), 6.59 (d, 1H), 4.11 (q, 2H), 1.57 (s, 6H), 1.48 (t, 3H); 13C NMR in CDCl3: δ 158.7, 147.9, 143.9, 142.9, 135.8, 133.4, 132.1, 130.4, 129.1, 128.9, 128.8, 125.6, 124.9, 124.3, 120.6, 115.6, 110.0, 72.4, 63.9, 31.6, 14.8; Mass Spec: 399.3 (M + H)+ | 2-[4-[(Z)-2-[1-(4-ethoxyphenyl)benzimidazol-5-yl]vinyl]phenyl]propan-2-ol |

The compounds of the invention include compounds which are of the following general Formula II or a pharmaceutically acceptable salt thereof:

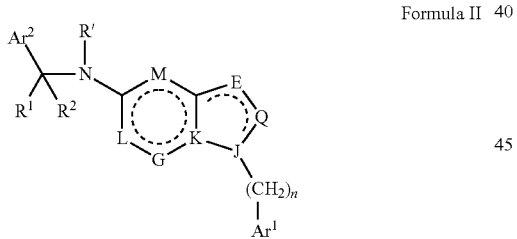

Formula II wherein, E is independently N, N+—O−, or C—R; G, L, M, and Q are independently N or C—R; and J and K are independently N or C with the proviso that when n=0, E and J cannot both be N;

R is selected from the group consisting of hydrogen, substituted or unsubstituted alkyl, haloalkyl, alkenyl, alkynyl, cycloalkyl, heterocycloalkyl, arylalkyl, aryl, heteroaryl, hydroxy, alkyloxy, aryloxy, heteroaryloxy, acyloxy, arylacyloxy, heteroarylacyloxy, alkylsulfonyloxy, arylsulfonyloxy, thio, alkylthio, arylthio, amino, alkylamino, dialkylamino, cycloalkylamino, heterocycloalkylamino, arylamino, heteroarylamino, acylamino, arylacylamino, heteroarylacylamino, alkylsulfonylamino, arylsulfonylamino, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, carboxy, alkoxycarbonyl, cycloalkyloxycarbonyl, aryloxycarbonyl, carbamoyl, substituted carbamoyl, halogen, cyano, isocyano and nitro;

R' is as follows:
(a) R' is independently selected from the group consisting of: hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;
(b) R' together with the nitrogen atom it is attached to, the carbon atom $R^1$ and $R^2$ are attached to, $R^1$ or $R^2$, form a substituted or unsubstituted ring, which optionally includes one or more heteroatoms in the ring;
(c) R' together with the nitrogen atom it is attached to, the carbon atom $R^1$ and $R^2$ are attached to, some carbons of $Ar^2$, form a substituted or unsubstituted ring, which optionally includes one or more heteroatoms in the ring; or
(d) R' together with the nitrogen atom it is attached to, some carbons of the aromatic ring next to this nitrogen, form a substituted or unsubstituted ring, which optionally includes one or more heteroatoms in the ring;

$R^1$ and $R^2$ are as follows:
(a) $R^1$ and $R^2$ are independently selected from the group consisting of hydrogen, alkyl, alkenyl, alkynyl, cycloalkyl, heterocycloalkyl, arylalkyl, aryl, heteroaryl, acyl, arylacyl, heteroarylacyl, alkylsulfinyl, arylsulfinyl, heteroarylsulfinyl, hydroxysulfonyl, alkylsulfonyl, arylsulfonyl, heteroarylsulfonyl, aminosulfonyl, substituted aminosulfonyl, alkoxycarbonyl, cycloalkyloxycarbonyl, aryloxycarbonyl, carbamoyl and substituted carbamoyl;

(b) R¹ and R² together with the carbon atom they are attached to form a substituted or unsubstituted ring, which optionally include one or more heteroatoms in the ring;

(c) R¹ or R² together with the carbon atom it is attached to, the nitrogen next to this carbon, and some carbons of the aromatic ring next to this nitrogen, form a substituted or unsubstituted ring, which optionally include one or more heteroatoms in the ring; or (d) R¹ or R² together with the carbon atom it is attached to, some carbons of Ar², form a substituted or unsubstituted ring, which optionally includes one or more heteroatoms in the ring;

n is an integer from 0-4; and

Ar¹ and Ar² are independently (un)substituted aryl or heteroaryl.

Preferably for compounds of Formula II, each of E and K is N; each of G, L, M and Q is C—R and R is hydrogen; and J is C.

Preferably, the compound of Formula II of the present invention is selected from the group consisting of 3-[(4-ethoxyphenyl)methyl]-N-[(4-ethylphenyl)-methyl]imidazo-[4,5-b]pyridin-6-amine; 1-(4-ethoxyphenyl)-N-[(4-ethylphenyl)-methyl]indol-5-amine; 3-(4-ethoxyphenyl)-N-[(4-ethylphenyl)-methyl]-1H-indol-6-amine; 3-(4-ethoxyphenyl)-N-[(4-ethylphenyl)-methyl]imidazo[1,2-a]pyridin-7-amine; 1-(4-ethoxyphenyl)-N-[(4-ethylphenyl)-methyl]pyrrolo[2,3-b]pyridin-5-amine; and 1-(4-ethoxyphenyl)-N-[(4-ethylphenyl)-methyl]-3-oxido-benzimidazol-3-ium-5-amine shown below in Table 2.

TABLE 2

Compounds of the invention of Formula II

| Cmpd | Chemical Structure | Molecular Formula | Analytical Data | Chemical Name |
|---|---|---|---|---|
| 62 | 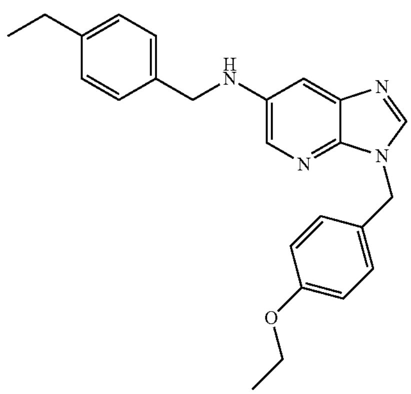 [SMILES: CCOc1ccc(Cn2cnc3cc(NCc4ccc(CC)cc4)cnc32)cc1] | $C_{24}H_{26}N_4O$ | 1H NMR in CDCl3: δ 7.96 (d, 1H), 7.83 (s, 1H), 7.28-7.33 (m, 3H), 7.16-7.25 (m, 4H), 6.82-6.85 (m, 2H), 5.31 (s, 2H), 4.33 (s, 2H), 3.97-4.08 (m, 3H), 2.64 (q, 2H), 1.39 (t, 3H), 1.23 (t, 3H); 13C NMR in CDCl3: δ 158.8, 143.5, 143.3, 141.7, 136.1, 136.0, 133.8, 129.2, 128.2, 127.9, 127.6, 114.8, 109.8, 63.5, 48.9, 46.6, 28.5, 15.6, 14.8; Mass Spec: 387.3 (M + H)⁺ | 3-[(4-ethoxyphenyl)methyl]-N-[(4-ethylphenyl)-methyl]imidazo[4,5-b]pyridin-6-amine |
| 63 | 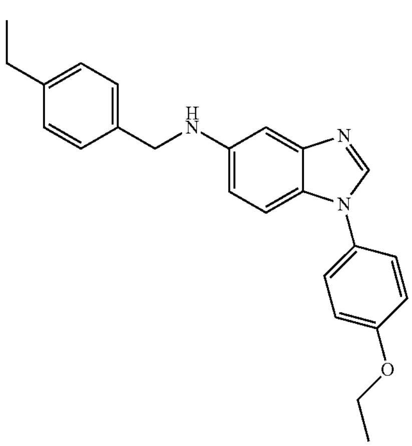 [SMILES: CCOc1ccc(-n2cnc3cc(NCc4ccc(CC)cc4)ccc32)cc1] | $C_{25}H_{26}N_2O$ | 1H NMR in CDCl3: δ 7.24-7.38 (m, 5H), 7.16-7.19 (m, 3H), 6.96-7.01 (m, 2H), 6.89 (d, 1H), 6.64 (dd, 1H), 6.46 (dd, 1H), 4.34 (s, 2H), 4.07 (q, 2H), 3.82 (bs, 1H), 2.64 (q, 2H), 1.45 (t, 3H), 1.24 (t, 3H); 13C NMR in CDCl3: δ 157.2, 143.1, 142.7, 137.2, 133.1, 130.6, 129.9, 128.2, 128.1, 127.7, 125.4, 115.2, 112.1, 111.1, 102.4, 102.0, 63.8, 49.4, 28.5, 15.7, 14.9; Mass Spec: 371.1 (M + H)⁺ | 1-(4-ethoxyphenyl)-N-[(4-ethylphenyl)-methyl]indol-5-amine |

TABLE 2-continued

Compounds of the invention of Formula II

| Cmpd | Chemical Structure | Molecular Formula | Analytical Data | Chemical Name |
|---|---|---|---|---|
| 64 | 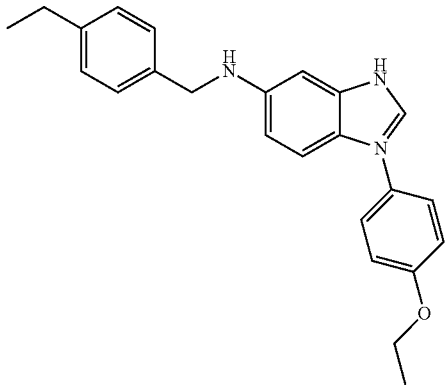 | $C_{25}H_{26}N_2O$ | 1H NMR in CDCl3: δ 7.83 (bs, 1H), 7.65 (d, 1H), 7.51-7.56 (m, 2H), 7.32 (d, 2H), 7.17 (d, 2H), 7.05 (d, 1H), 6.93-6.98 (m, 2H), 6.57-6.63 (m, 2H), 4.34 (s, 2H), 4.07 (q, 2H), 2.64 (q, 2H), 1.43 (t, 3H), 1.24 (t, 3H); 13C NMR in CDCl3: δ 157.4, 145.0, 143.4, 138.4, 137.0, 128.6, 128.5, 128.3, 127.8, 120.6, 118.7, 118.2, 115.0, 110.4, 93.6, 63.8, 49.2, 28.9, 16.1, 15.3; Mass Spec: 371.1 (M + H)+ | 3-(4-ethoxyphenyl)-N-[(4-ethylphenyl)-methyl]-1H-indol-6-amine |
| 65 | 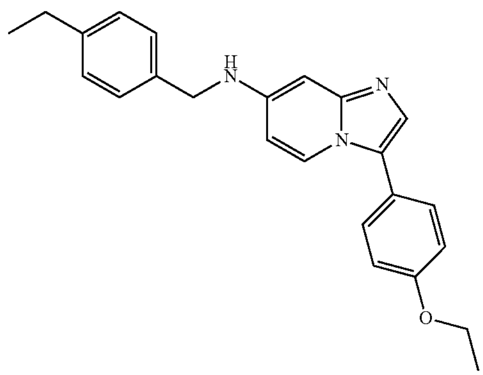 [SMILES: CCOc1ccc(-c2cnc3cc(NCc4ccc(CC)cc4)ccn23)cc1] | $C_{24}H_{25}N_3O$ | 1H NMR in CDCl3: δ 7.95 (bs, 1H), 7.15-7.39 (m, 7H), 6.98 (d, 2H), 6.54 (bs, 1H), 6.25 (d, 1H), 4.49 (bs, 1H), 4.30 (s, 2H), 4.07 (q, 2H), 2.62 (q, 2H), 1.44 (t, 3H), 1.22 (t, 3H); 13C NMR in CDCl3: δ 158.5, 145.2, 143.6, 135.3, 129.2, 128.6, 128.2, 128.1, 127.6, 127.2, 123.6, 122.1, 115.1, 106.4, 92.4, 63.6, 47.6, 28.5, 15.6, 14.8; Mass Spec: 372.0 (M + H)+ | 3-(4-ethoxyphenyl)-N-[(4-ethylphenyl)-methyl]imidazo[1,2-a]pyridin-7-amine |
| 66 | 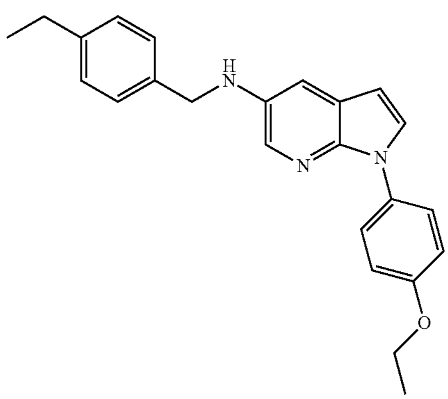 [SMILES: CCOc1ccc(-n2ccc3cc(NCc4ccc(CC)cc4)cnc32)cc1] | $C_{24}H_{25}N_3O$ | 1H NMR in CDCl3: δ 7.92 (d, 1H), 7.55-7.59 (m, 2H), 7.31-7.35 (m, 3H), 7.17-7.20 (m, 3H), 6.99-7.03 (m, 2H), 6.41 (d, 1H), 4.34 (s, 2H), 4.07 (q, 2H), 2.64 (q, 2H), 1.44 (t, 3H), 1.23 (t, 3H); 13C NMR in CDCl3: δ 157.1, 143.4, 142.5, 139.5, 136.4, 133.3, 131.8, 128.2, 128.1, 127.7, 125.1, 121.5, 115.2, 111.0, 100.0, 63.8, 49.2, 28.5, 15.6, 14.9; Mass Spec: 372.3 (M + H)+ | 1-(4-ethoxyphenyl)-N-[(4-ethylphenyl)-methyl]pyrrolo[2,3-b]pyridin-5-amine |
| 67 | 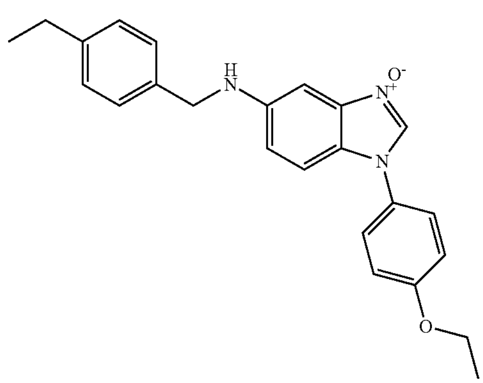 | $C_{24}H_{25}N_3O_2$ | 1H NMR in CD3OD: δ 8.78 (s, 1H), 7.45-7.50 (m, 2H), 7.27-7.31 (m, 3H), 7.08-7.15 (m, 4H), 6.96 (dd, 1H), 6.83 (d, 1H), 4.36 (s, 2H), 4.11 (q, 2H), 2.59 (q, 2H), 1.42 (t, 3H), 1.19 (t, 3H); 13C NMR in CDCl3: δ 159.5, 147.4, 142.8, 136.3, 133.3, 127.6, 127.1, 127.0, 125.6, 121.8, 116.4, 115.4, 112.2, 91.2, 63.6, 28.1, 14.8, 13.6; Mass Spec: 388.2 (M + H)+ | 1-(4-ethoxyphenyl)-N-[(4-ethylphenyl)-methyl]-3-oxido-benzimidazol-3-ium-5-amine |

The method of the present invention is for the treatment or prophylaxis of a viral infection or disease associated therewith, comprising administering in a therapeutically effective amount to a mammal in need thereof, a compound of Formula I or II described above.

Preferably, the mammal is a human and the viral infection is an *arenavirus* infection. More preferably, the *arenavirus* virus is selected from the group consisting of Lassa, Junin, Machupo, Guanarito, Sabia, Whitewater Arroyo, Chapare, LCMV, LCMV-like viruses such as Dandenong, Tacaribe, and Pichinde.

Preferably, the viral infection is associated with a condition selected from the group consisting of Lassa fever, Argentine hemorrhagic fever, Bolivian hemorrhagic fever, and Venezuelan hemorrhagic fever. Most preferably, the viral infection is associated with Lassa fever.

The method of the present invention may also comprise co-administration of: a) other antivirals such as ribavirin or cidofovir; b) vaccines; and/or c) interferons or pegylated interferons.

Definitions

In accordance with this detailed description, the following abbreviations and definitions apply. It must be noted that as used herein, the singular forms "a," "an," and "the" include plural referents unless the context clearly dictates otherwise.

The publications discussed herein are provided solely for their disclosure. Nothing herein is to be construed as an admission regarding antedating the publications. Further, the dates of publication provided may be different from the actual publication dates, which may need to be independently confirmed.

Where a range of values is provided, it is understood that each intervening value is encompassed. The upper and lower limits of these smaller ranges may independently be included in the smaller, subject to any specifically-excluded limit in the stated range. Where the stated range includes one or both of the limits, ranges excluding either both of those included limits are also included in the invention. Also contemplated are any values that fall within the cited ranges.

Unless defined otherwise, all technical and scientific terms used herein have the same meaning as commonly understood by one of ordinary skill in the art. Any methods and materials similar or equivalent to those described herein can also be used in practice or testing. All publications mentioned herein are incorporated herein by reference to disclose and describe the methods and/or materials in connection with which the publications are cited.

By "patient" or "subject" is meant to include any mammal. A "mammal," for purposes of treatment, refers to any animal classified as a mammal, including but not limited to, humans, experimental animals including rats, mice, and guinea pigs, domestic and farm animals, and zoo, sports, or pet animals, such as dogs, horses, cats, cows, and the like.

The term "efficacy" as used herein refers to the effectiveness of a particular treatment regime. Efficacy can be measured based on change of the course of the disease in response to an agent.

The term "success" as used herein in the context of a chronic treatment regime refers to the effectiveness of a particular treatment regime. This includes a balance of efficacy, toxicity (e.g., side effects and patient tolerance of a formulation or dosage unit), patient compliance, and the like. For a chronic administration regime to be considered "successful" it must balance different aspects of patient care and efficacy to produce a favorable patient outcome.

The terms "treating," "treatment," and the like are used herein to refer to obtaining a desired pharmacological and physiological effect. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment," as used herein, covers any treatment of a disease in a mammal, such as a human, and includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; and (c) relieving the disease, i.e., causing regression of the disease and/or its symptoms or conditions. Treating a patient's suffering from disease related to pathological inflammation is contemplated. Preventing, inhibiting, or relieving adverse effects attributed to pathological inflammation over long periods of time and/or are such caused by the physiological responses to inappropriate inflammation present in a biological system over long periods of time are also contemplated.

As used herein, "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkylC—(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkylamino" refers to the group —NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R is joined to form together with the nitrogen atom a heterocyclic or substituted heterocyclic ring wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 10 carbon atoms and more preferably 2 to 6 carbon atoms and having at least 1 and preferably from 1-2 sites of alkenyl unsaturation.

"Alkoxy" refers to the group "alkyl-O—" which includes, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkyl" refers to linear or branched alkyl groups having from 1 to 10 carbon atoms, alternatively 1 to 6 carbon atoms. This term is exemplified by groups such as methyl, t-butyl, n-heptyl, octyl and the like.

"Amino" refers to the group —NH$_2$.

"Aryl" or "Ar" refers to an unsaturated aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3

(4H)-one, and the like) provided that the point of attachment is through an aromatic ring atom.

"Substituted aryl" refers to aryl groups which are substituted with from 1 to 3 substituents selected from the group consisting of hydroxy, acyl, acylamino, thiocarbonylamino, acyloxy, alkyl, substituted alkyl, haloalkyl, hydroxyalkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, oxetane, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OS(O)$_2$—NRR where R is hydrogen. or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR— substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl)amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Cycloalkyl" refers to cyclic alkyl groups of from 3 to 8 carbon atoms having a single cyclic ring including, by way of example, cyclopropyl, cyclobutyl, cyclopentyl, cyclohexyl, cyclooctyl and the like. Excluded from this definition are multi-ring alkyl groups such as adamantanyl, etc.

"Halo" or "halogen" refers to fluoro, chloro, bromo and iodo.

"Heteroaryl" refers to an aromatic carbocyclic group of from 2 to 10 carbon atoms and 1 to 4 heteroatoms selected from the group consisting of oxygen, nitrogen and sulfur within the ring or oxides thereof. Such heteroaryl groups can have a single ring (e.g., pyridyl or furyl) or multiple condensed rings (e.g., indolizinyl or benzothienyl) wherein one or more of the condensed rings may or may not be aromatic provided that the point of attachment is through an aromatic ring atom. Additionally, the heteroatoms of the heteroaryl group may be oxidized, i.e., to form pyridine N-oxides or 1,1-dioxo-1,2,5-thiadiazoles and the like. Additionally, the carbon atoms of the ring may be substituted with an oxo (=O). The term "heteroaryl having two nitrogen atoms in the heteroaryl, ring" refers to a heteroaryl group having two, and only two, nitrogen atoms in the heteroaryl ring and optionally containing 1 or 2 other heteroatoms in the heteroaryl ring, such as oxygen or sulfur.

"Substituted heteroaryl" refers to heteroaryl groups which are substituted with from 1 to 3 substituents selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxylalkyl, carboxyl-substituted alkyl, carboxyl-cycloalkyl, carboxyl-substituted cycloalkyl, carboxylaryl, carboxyl-substituted aryl, carboxylheteroaryl, carboxyl-substituted heteroaryl, carboxylheterocyclic, carboxyl-substituted heterocyclic, carboxylamido, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, guanidinosulfone, halo, nitro, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NRR where R is hydrogen or alkyl, —NRS(O)$_2$-alkyl, —NRS(O)$_2$-substituted alkyl, —NRS(O)$_2$-aryl, —NRS(O)$_2$-substituted aryl, —NRS(O)$_2$-heteroaryl, —NRS(O)$_2$-substituted heteroaryl, —NRS(O)$_2$-heterocyclic, —NRS(O)$_2$-substituted heterocyclic, —NRS(O)$_2$—NR-alkyl, —NRS(O)$_2$—NR-substituted alkyl, —NRS(O)$_2$—NR-aryl, —NRS(O)$_2$—NR-substituted aryl, —NRS(O)$_2$—NR-heteroaryl, —NRS(O)$_2$—NR-substituted heteroaryl, —NRS(O)$_2$—NR-heterocyclic, —NRS(O)$_2$—NR-substituted heterocyclic where R is hydrogen or alkyl, mono- and di-alkylamino, mono- and di-(substituted alkyl) amino, mono- and di-arylamino, mono- and di-substituted arylamino, mono- and di-heteroarylamino, mono- and di-substituted heteroarylamino, mono- and di-heterocyclic amino, mono- and di-substituted heterocyclic amino, unsymmetric di-substituted amines having different substituents independently selected from the group consisting of alkyl, substituted alkyl, aryl, substituted aryl, heteroaryl, substituted heteroaryl, heterocyclic and substituted heterocyclic and amino groups on the substituted aryl blocked by conventional blocking groups such as Boc, Cbz, formyl, and the like or substituted with —SO$_2$NRR where R is hydrogen or alkyl.

"Sulfonyl" refers to the group —S(O)$_2$R where R is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Optionally substituted" means that the recited group may be unsubstituted or the recited group may be substituted.

"Pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use.

"Pharmaceutically-acceptable cation" refers to the cation of a pharmaceutically-acceptable salt.

"Pharmaceutically-acceptable salt" refers to salts which retain the biological effectiveness and properties of compounds which are not biologically or otherwise undesirable. Pharmaceutically-acceptable salts refer to pharmaceutically-acceptable salts of the compounds, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

Pharmaceutically-acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri (iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower alkyl carboxamides, dialkyl carboxamides, and the like.

Pharmaceutically-acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

A compound may act as a pro-drug. Pro-drug means any compound which releases an active parent drug in vivo when such pro-drug is administered to a mammalian subject. Pro-drugs are prepared by modifying functional groups present in such a way that the modifications may be cleaved in vivo to release the parent compound. Pro-drugs include compounds wherein a hydroxy, amino, or sulfhydryl group is bonded to any group that may be cleaved in vivo to regenerate the free hydroxyl, amino, or sulfhydryl group, respectively. Examples of pro-drugs include, but are not limited to esters (e.g., acetate, formate, and benzoate derivatives), carbamates (e.g., N,N-dimethylamino-carbonyl) of hydroxy functional groups, and the like.

"Treating" or "treatment" of a disease includes:
(1) preventing the disease, i.e. causing the clinical symptoms of the disease not to develop in a mammal that may be exposed to or predisposed to the disease but does not yet experience or display symptoms of the disease,
(2) inhibiting the disease, i.e., arresting or reducing the development of the disease or its clinical symptoms, or
(3) relieving the disease, i.e., causing regression of the disease or its clinical symptoms.

A "therapeutically-effective amount" means the amount of a compound that, when administered to a mammal for treating a disease, is sufficient to effect such treatment for the disease. The "therapeutically-effective amount" will vary depending on the compound, the disease, and its severity and the age, weight, etc., of the mammal to be treated.

Synthesis of Compounds

The compounds are readily prepared via several divergent synthetic routes with the particular route selected relative to the ease of compound preparation, the commercial availability of starting materials, and the like.

The compounds can be prepared from readily-available starting materials using the following general methods and procedures. It will be appreciated that where process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Second Edition, Wiley, New York, 1991, and references cited therein.

Furthermore, the compounds may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included unless otherwise indicated. Pure stereoisomers (or enriched mixtures) may be prepared using, for example, optically-active starting materials or stereoselective reagents well-known in the art. Alternatively, racemic mixtures of such compounds can be separated using, for example, chiral column chromatography, chiral resolving agents, and the like.

Unless otherwise indicated, if the products contain chiral centers, they are a mixture of R, S enantiomers. However, when a chiral product is desired, the chiral product can be obtained via purification techniques which separate enantiomers from a R, S mixture to provide for one or the other stereoisomer. Such techniques are known in the art.

The compounds can be provided as pro-drugs which convert (e.g., hydrolyze, metabolize, etc.) in vivo to a compound above.

Pharmaceutical Formulations of the Compounds

In general, compounds will be administered in a therapeutically-effective amount by any of the accepted modes of administration for these compounds. The compounds can be administered by a variety of routes, including, but not limited to, oral, parenteral (e.g., subcutaneous, subdural, intravenous, intramuscular, intrathecal, intraperitoneal, intracerebral, intraarterial, or intralesional routes of administration), topical, intranasal, localized (e.g., surgical application or surgical suppository), rectal, and pulmonary (e.g., aerosols, inhalation, or powder). Accordingly, these compounds are effective as both injectable and oral compositions. The compounds can be administered continuously by infusion or by bolus injection.

The actual amount of the compound, i.e., the active ingredient, will depend on a number of factors, such as the severity of the disease, i.e., the condition or disease to be treated, age, and relative health of the subject, the potency of the compound used, the route and form of administration, and other factors.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage for use in humans. The dosage of such compounds lies within a range of circulating concentrations that include the $ED_{50}$ with little or no toxicity. The dosage may vary within this range depending upon the dosage form employed and the route of administration utilized. For any compound used, the therapeutically-effective dose can be estimated initially from cell culture assays. A dose may be formulated in animal models to achieve a circulating plasma concentration range which includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The amount of the pharmaceutical composition administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically-effective dose." Amounts effective for this use will depend on the disease condition being treated as well as by the judgment of the attending clinician depending upon factors such as the severity of the inflammation, the age, weight, and general condition of the patient, and the like.

The compositions administered to a patient are in the form of 24 pharmaceutical compositions described supra. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. It will be understood that use of certain of the foregoing excipients, carriers, or stabilizers will result in the formation of pharmaceutical salts.

The active compound is effective over a wide dosage range and is generally administered in a pharmaceutically- or therapeutically-effective amount. The therapeutic dosage of the compounds will vary according to, for example, the particular use for which the treatment is made, the manner of administration of the compound, the health and condition of the patient, and the judgment of the prescribing physician. For example, for intravenous administration, the dose will typically be in the range of about 0.5 mg to about 100 mg per kilogram body weight. Effective doses can be extrapolated from dose-response curves derived from in vitro or animal model test systems. Typically, the clinician will administer the compound until a dosage is reached that achieves the desired effect.

When employed as pharmaceuticals, the compounds are usually administered in the form of pharmaceutical compositions. Pharmaceutical compositions contain as the active ingredient one or more of the compounds above, associated with one or more pharmaceutically-acceptable carriers or excipients. The excipient employed is typically one suitable for administration to human subjects or other mammals. In making the compositions, the active ingredient is usually mixed with an excipient, diluted by an excipient, or enclosed within a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained, or delayed-release of the active ingredient after administration to the patient by employing procedures known in the art.

The quantity of active compound in the pharmaceutical composition and unit dosage form thereof may be varied or adjusted widely depending upon the particular application, the manner or introduction, the potency of the particular compound, and the desired concentration. The term "unit dosage forms" refers to physically-discrete units suitable as unitary dosages for human subjects and other mammals, each unit containing a predetermined quantity of active material calculated to produce the desired therapeutic effect, in association with a suitable pharmaceutical excipient.

The compound can be formulated for parenteral administration in a suitable inert carrier, such as a sterile physiological saline solution. The dose administered will be determined by route of administration.

Administration of therapeutic agents by intravenous formulation is well known in the pharmaceutical industry. An intravenous formulation should possess certain qualities aside from being just a composition in which the therapeutic agent is soluble. For example, the formulation should promote the overall stability of the active ingredient(s), also, the manufacture of the formulation should be cost-effective. All of these factors ultimately determine the overall success and usefulness of an intravenous formulation.

Other accessory additives that may be included in pharmaceutical formulations and compounds as follow: solvents: ethanol, glycerol, propylene glycol; stabilizers: EDTA (ethylene diamine tetraacetic acid), citric acid; antimicrobial preservatives: benzyl alcohol, methyl paraben, propyl paraben; buffering agents: citric acid/sodium citrate, potassium hydrogen tartrate, sodium hydrogen tartrate, acetic acid/sodium acetate, maleic acid/sodium maleate, sodium hydrogen phthalate, phosphoric acid/potassium dihydrogen phosphate, phosphoric acid/disodium hydrogen phosphate; and tonicity modifiers: sodium chloride, mannitol, dextrose.

The presence of a buffer is necessary to maintain the aqueous pH in the range of from about 4 to about 8. The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of drug. Generally, the amount of buffer used is able to maintain a formulation pH in the range of 4 to 8. Generally, a 1:1 to 10:1 mole ratio of buffer (where the moles of buffer are taken as the combined moles of the buffer ingredients, e.g., sodium citrate and citric acid) to drug is used.

A useful buffer is sodium citrate/citric acid in the range of 5 to 50 mg per ml. sodium citrate to 1 to 15 mg per ml. citric acid, sufficient to maintain an aqueous pH of 4-6 of the composition.

The buffer agent may also be present to prevent the precipitation of the drug through soluble metal complex formation with dissolved metal ions, e.g., Ca, Mg, Fe, Al, Ba, which may leach out of glass containers or rubber stoppers or be present in ordinary tap water. The agent may act as a competitive complexing agent with the drug and produce a soluble metal complex leading to the presence of undesirable particulates.

In addition, the presence of an agent, e.g., sodium chloride in an amount of about of 1-8 mg/ml, to adjust the tonicity to the same value of human blood may be required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9% solution of sodium chloride.

An intravenous formulation can be administered by direct intravenous injection, i.v. bolus, or can be administered by infusion by addition to an appropriate infusion solution such as 0.9% sodium chloride injection or other compatible infusion solution.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 2000 mg of the active ingredient.

The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically-acceptable, aqueous or organic solvents, or mixtures thereof, and powders. The liquid or solid compositions may contain suitable pharmaceutically-acceptable excipients as described supra. Compositions in pharmaceutically-acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered from devices which deliver the formulation in an appropriate manner.

The compounds can be administered in a sustained release form. Suitable examples of sustained-release preparations include semipermeable matrices of solid hydrophobic polymers containing the compounds, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.* 15: 167-277 (1981) and Langer, *Chem. Tech.* 12: 98-105 (1982) or poly(vinyl alcohol)), polylactides (U.S. Pat. No. 3,773, 919), copolymers of L-glutamic acid and gamma ethyl-L-glutamate (Sidman et al., *Biopolymers* 22: 547-556, 1983), non-degradable ethylene-vinyl acetate (Langer et al., supra), degradable lactic acid-glycolic acid copolymers such as the LUPRON DEPOT™ (i.e., injectable microspheres composed of lactic acid-glycolic acid copolymer and leuprolide acetate), and poly-D-(−)-3-hydroxybutyric acid (EP 133, 988).

The compounds can be administered in a sustained-release form, for example a depot injection, implant preparation, or osmotic pump, which can be formulated in such a manner as to permit a sustained-release of the active ingredient. Implants for sustained-release formulations are well-known in the art. Implants may be formulated as, including but not limited to, microspheres, slabs, with biodegradable or non-biodegradable polymers. For example, polymers of lactic acid and/or glycolic acid form an erodible polymer that is well-tolerated by the host.

Transdermal delivery devices ("patches") may also be employed. Such transdermal patches may be used to provide continuous or discontinuous infusion of the compounds in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on-demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid-soluble and amenable to transportation across the blood-brain barrier. Alternatively, the delivery of hydrophilic drugs may be enhanced by intra-arterial infusion of hypertonic solutions which can transiently open the blood-brain barrier.

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka et al., U.S. Pat. Nos. 4,235,871, 4,501,728 and 4,837,028 each of which is incorporated herein by reference.

Pharmaceutical compositions are suitable for use in a variety of drug delivery systems. Suitable formulations for use in the present invention are found in *Remington's Pharmaceutical Sciences*, Mace Publishing Company, Philadelphia, Pa., 17th ed. (1985).

The provided compounds and pharmaceutical compositions show biological activity in treating and preventing viral infections and associated diseases, and, accordingly, have utility in treating viral infections and associated diseases, such as hemorrhagic fever viruses, in mammals including humans.

Hemorrhagic fever viruses (HFVs) are RNA viruses that cause a variety of disease syndromes with similar clinical characteristics. HFVs that are of concern as potential biological weapons include but are not limited to: Arenaviridae (Junin, Machupo, Guanarito, Sabia, and Lassa), Filoviridae (Ebola and Marburg viruses), Flaviviridae (yellow fever, Omsk hemorrhagic fever and Kyasanur Forest disease viruses), and Bunyaviridae (Rift Valley fever and Crimean-Congo hemorrhagic fever). The naturally-occurring arenaviruses and potential engineered arenaviruses are included in the Category A Pathogen list according to the Centers for Disease Control and Prevention as being among those agents that have greatest potential for mass casualties.

Risk factors include: travel to Africa or Asia, handling of animal carcasses, contact with infected animals or people, and/or arthropod bites. Arenaviruses are highly infectious after direct contact with infected blood and/or bodily secretions. Humans usually become infected through contact with infected rodents, the bite of an infected arthropod, direct contact with animal carcasses, inhalation of infectious rodent excreta and/or injection of food contaminated with rodent excreta. The Tacaribe virus has been associated with bats. Airborne transmission of hemorrhagic fever is another mode. Person-to-person contact may also occur in some cases.

All of the hemorrhagic fevers exhibit similar clinical symptoms. However, in general the clinical manifestations are non-specific and variable. The incubation period is approximately 7-14 days. The onset is gradual with fever and malaise, tachypnea, relative bradycardia, hypotension, circulatory shock, conjunctival infection, pharyngitis, lymphadenopathy, encephalitis, myalgia, back pain, headache and dizziness, as well as hyperesthesia of the skin. Some infected patients may not develop hemorrhagic manifestations.

Methods of diagnosis at specialized laboratories include antigen detection by antigen-capture enzyme-linked immunosorbent assay (ELISA), IgM antibody detection by antibody-capture enzyme-linked immunosorbent assay, reverse transcriptase polymerase chain reaction (RT-PCR), and viral isolation. Antigen detection (by enzyme-linked immunosorbent assay) and reverse transcriptase polymerase chain reaction are the most useful diagnostic techniques in the acute clinical setting. Viral isolation is of limited value because it requires a biosafety level 4 (BSL-4) laboratory.

In the examples below, if an abbreviation is not defined above, it has its generally accepted meaning. Further, all temperatures are in degrees Celsius (unless otherwise indicated). The following Methods were used to prepare the compounds set forth below as indicated.

Example 1—Formulation 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Example 2—Formulation 2

A tablet formula is prepared using the ingredients below:

| Ingredient | Quantity (mg/capsule) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 3—Formulation 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Example 4—Formulation 4

Tablets, each containing 30 mg of active ingredient, are prepared as follows:

| Ingredient | Quantity (mg/capsule) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium Carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules, which after mixing, are compressed on a tablet machine to yield tablets each weighing 150 mg.

Example 5—Formulation 5

Capsules, each containing 40 mg of medicament, are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Example 6—Formulation 6

Suppositories, each containing 25 mg of active ingredient, are made as follows:

| Ingredient | Amount |
| --- | --- |
| Active Ingredient | 25 mg |
| Saturated fatty acids glycerides | to 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 7—Formulation 7

Suspensions, each containing 50 mg of medicament per 5.0 ml dose, are made as follows:

| Ingredient | Amount |
| --- | --- |
| Active Ingredient | 50.0 mg |
| Xanthan gum | 4.0 mg |
| Sodium carboxymethyl cellose (11%) | |
| Microcrystalline cellulose (89%) | 500 mg |
| Sucrose | 1.75 g |
| Sodium benzoate | 10.0 mg |
| Flavor and color | q.v. |
| Purified water | to 5.0 ml |

The medicament, sucrose, and xanthan gum are blended, passed through a NO. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 8—Formulation 8

Hard gelatin tablets, each containing 15 mg of active ingredient, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Example 9—Formulation 9

An intravenous formulation may be prepared as follows:

| Ingredient | (mg/capsule) |
| --- | --- |
| Active Ingredient | 250.0 mg |
| Isotonic saline | 1000 ml |

Therapeutic compound compositions generally are placed into a container having a sterile access port, for example, an intravenous solution bag or vial having a stopper pierceable by a hypodermic injection needle or similar sharp instrument.

Example 10—Formulation 10

A topical formulation may be prepared as follows:

| Ingredient | Quantity |
| --- | --- |
| Active Ingredient | 1-10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Example 11—Formulation 11

An aerosol formulation may be prepared as follows: A solution of the candidate compound in 0.5% sodium bicarbonate/saline (w/v) at a concentration of 30.0 mg/mL is prepared using the following procedure:

Preparation of 0.5% Sodium Bicarbonate/Saline Stock Solution: 100.0 mL

| Ingredient | Gram/100.0 mL | Final Concentration |
| --- | --- | --- |
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

Preparation of 30.0 mg/mL Candidate Compound: 10.0 mL

| Ingredient | Gram/100.0 mL | Final Concentration |
| --- | --- | --- |
| Candidate Compound | 0.300 g | 30.0 mg/mL |
| .05% Sodium Bicarbonte/Saline Stock Solution | q.s. ad 10.0 mL | q.s. ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix.

Example 12—Synthesis of 1-(4-ethoxyphenyl)-5-[(E)-2-(4-ethylphenyl)vinyl]benzimidazole (Compound 1), 1-(4-ethoxyphenyl)-5-[(Z)-2-(4-ethylphenyl)vinyl]benzimidazole (Compound 2), and 1-(4-ethoxyphenyl)-5-[2-(4-ethylphenyl)-ethyl]benzimidazole (Compound 27)

1-(4-ethoxyphenyl)-5-[(E)-2-(4-ethylphenyl)-vinyl]benzimidazole (Compound 1), 1-(4-ethoxyphenyl)-5-[(Z)-2-(4-ethylphenyl)vinyl]benzimidazole (Compound 2), and 1-(4-ethoxyphenyl)-5-[2-(4-ethylphenyl)-ethyl]benzimidazole (Compound 27) were synthesized according to the following scheme:

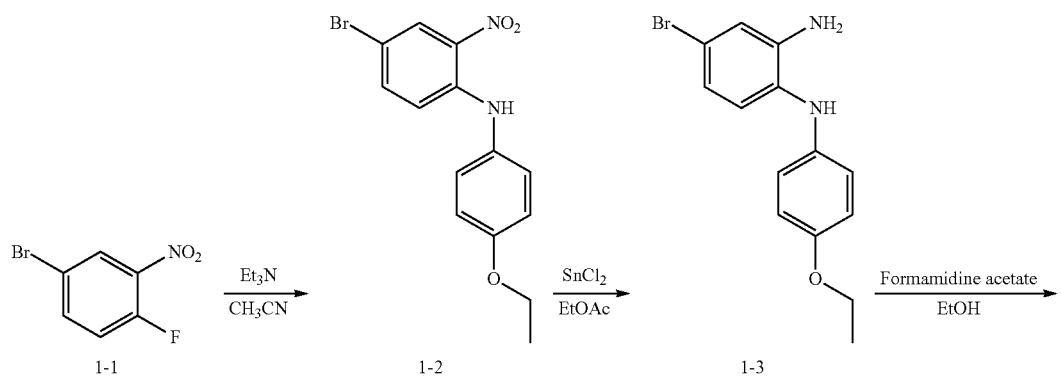
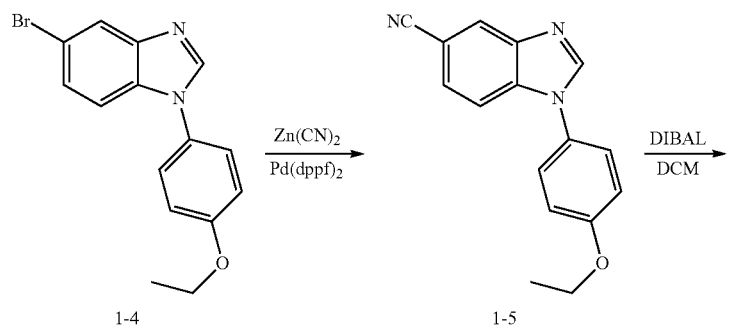
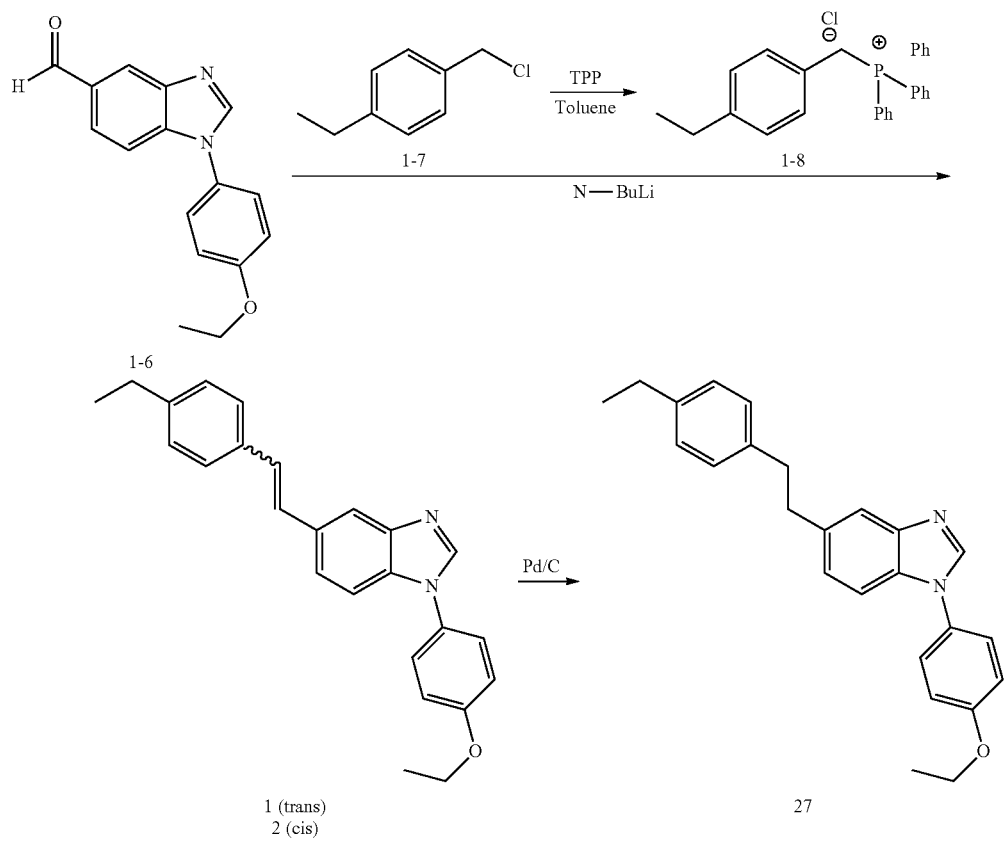

Example 12 was used as general procedure for compounds 1, 2, 4, 5, 6, 7, 8, 9, 10, 11, 12, 13, 14, 15, 16, 17, 27 and 43

Synthesis of 4-Bromo-N-(4-ethoxyphenyl)-2-nitroaniline (Compound 1-2)

To a solution of 4-bromo-1-fluoro-2-nitrobenzene (75.0 g, 0.341 mol, 1.0 equiv) in acetonitrile (375 mL) was added triethylamine (55 mL, 0.394 mol, 1.15 equiv) and 4-ethoxyaniline (55 mL, 0.427 mol, 1.25 equiv). The resulting red solution was stirred at reflux overnight and then cooled and concentrated under reduced pressure. The residue was partitioned between ethyl acetate (2.5 L) and water (1 L). The layers were separated and the aqueous layer was back-extracted with ethyl acetate (200 mL). The combined organic layers were dried over sodium sulfate and concentrated under reduced pressure. The crude material was slurried in tert-butyl methyl ether (250 mL) and filtered to give compound 1-2 (96.7 g, 84% yield) as a red solid which was used in the next step without further purification.

Synthesis of 4-Bromo-N1-(4-ethoxyphenyl)benzene-1,2-diamine (Compound 1-3)

A solution of compound 1-2 (96.7 g, 0.287 mol, 1.0 equiv) in ethyl acetate (2.5 L) was heated to 50° C. Tin chloride dihydrate (226.6 g, 1.00 mol, 3.5 equiv) was added in solid portions over 6 minutes. The temperature decreased from 51.5 to 48.5° C. during the addition and the color changed to orange. Heating was continued until LC-MS indicated that no starting material remained. The reaction was cooled to room temperature and aqueous sodium bicarbonate was added until the pH was basic (3 L). This mixture was stirred for 1 hour and filtered through Celite. The precipitate was washed well with ethyl acetate and water. The filtrate was transferred to a separatory funnel and the layers were separated. The organic layer was dried over sodium sulfate and evaporated under reduced pressure to give compound 1-3 (86.7 g, 98% yield) as a brownish red powder, which was used in the next step without further purification.

Synthesis of 5-Bromo-1-(4-ethoxyphenyl)-1H-benzo[d]imidazole (Compound 1-4)

To a solution of compound 1-3 (86.7 g, 0.28 mol, 1.0 equiv) in ethanol (2.2 L) was added formamidine acetate (88.8 g, 0.85 mol, 3 equiv). The reaction was heated at reflux for 9 hours and cooled to room temperature while stirred overnight. The solvent was removed under reduced pressure and the residue was diluted with water (500 mL), stirred for 30 minutes and filtered. The resulting solid was rinsed well with water and azeotroped repeatedly with toluene. The solid was dried in a vacuum oven at 50° C. to give compound 1-4 (83.5 g, 94% yield) as an orange solid which was used without further purification.

Synthesis of 1-(4-Ethoxyphenyl)-1H-benzo[d]imidazole-5-carbonitrile (Compound 1-5)

A mixture of N,N-dimethylacetamide (125 mL), water (3 mL), and poly(methoxyhydro)siloxane (3 mL) was degassed with a stream of nitrogen for 15 minutes. Compound 1-4 (5 g, 15.7 mmol, 1 equiv.), zinc cyanide (3.7 g, 31.5 mmol, 2 equiv.), and zinc dust (410 mg, 6.3 mmol, 0.4 equiv.) were added to the mixture which was heated to 100° C. Dichloro [1,1'-bis(diphenylphosphino)ferrocene] palladium (II) dichloromethane adduct (255 mg, 0.3 mmol, 0.05 equiv.) was added and heating was continued for 3 hours. The reaction was allowed to cool to room temperature, poured into 500 mL of water and extracted with ethyl acetate (2×500 mL). The combined organic layers were dried over sodium sulfate and concentrated under reduced pressure to give compound 1-5 as a light pink solid (3.6 g, 88% yield).

Synthesis of 1-(4-Ethoxyphenyl)-1H-benzo[d]imidazole-5-carbaldehyde (Compound 1-6)

A solution of compound 1-5 (3.6 g, 13.5 mmol, 1 equiv.) in dichloromethane (90 mL) was cooled with a dry ice/acetonitrile bath. A 1.5 M solution of diisobutyl aluminumhydride in toluene, (2.88 g, 13.5 mL, 20.2 mmol, 1.5 equiv.) was added drop wise via an addition funnel. Upon completion of the addition, the reaction was allowed to slowly warm to room temperature. The reaction was poured into a 10% sodium potassium tartrate solution (250 mL) and stirred for 20 minutes. The layers were separated and the dichloromethane was washed with saturated brine (100 mL). The organic layer was dried over sodium sulfate and concentrated under reduced pressure. The residue was purified by flash chromatography eluting with a gradient of 0-25% ethyl acetate in heptanes to give compound 1-6 as a white solid (1.6 g, 44% yield).

Synthesis of (4-Ethylbenzyl)triphenylphosphonium chloride (Compound 1-8)

To a stirred solution of 4-ethylbenzylchloride (1.54 g, 10 mmol, 1 equiv) was added triphenyl phosphine (2.62 g, 10 mmol, 1 equiv) in toluene (30 mL). The reaction was heated at reflux for 48 hours and allowed to cool to room temperature over the weekend. The suspension was filtered, washed with toluene (2×5 mL) and dried to give compound 1-8 as a white solid (2.5 g, 60% yield).

Synthesis of 1-(4-ethoxyphenyl)-5-[(E)-2-(4-ethylphenyl)vinyl]benzimidazole (compound 1) and 1-(4-ethoxyphenyl)-5-[(Z)-2-(4-ethylphenyl)vinyl]benzimidazole (Compound 2)

Compound 1-8 (157 mg, 0.38 mmol, 1 equiv) was dissolved in anhydrous tetrahydrofuran (5 mL) and cooled to −78° C. A 2.5M solution of n-butyl lithium in hexanes (160 µl, 0.40 mmol, 1.05 equiv) was added and the reaction was stirred at −78° C. for 1 hour. Compound 1-6 (100 mg, 0.38 mmol, 1 equiv) was added and the reaction was allowed to warm to room temperature over 2 hours. The reaction was concentrated and the residue was dissolved in dichloromethane (3 mL). This solution was filtered and purified via chromatography utilizing an AnaLogix 4 g column eluting with a gradient of 0-40% ethyl acetate in heptanes. This gave 1-(4-ethoxyphenyl)-5-(4-ethylstyryl)-1H-benzo[d]imidazole as a pale yellow semisolid (85 mg, 61% yield). An additional run was made at twice the scale and the cis and trans isomers were separated on an AnaLogix 8 g column eluting with a gradient of 0-40% ethyl acetate in heptanes to give 101 mg of compound 1 (37% yield) and 42 mg of compound 2 (15% yield).

Synthesis of 1-(4-Ethoxyphenyl)-5-(4-ethylphenethyl)-1H-benzo[d]imidazole (Compound 27)

A mixture of compound 1 and compound 2 (75 mg, 0.20 mmol, 1 equiv) was dissolved in methanol (40 mL) and 20% palladium on carbon (15 mg, 50% wet) was added. The reaction was hydrogenated at 60 psi for 18 hours. The reaction was filtered through Celite and the pad was washed with methanol (2×10 mL). The filtrates were concentrated under reduced pressure. The residue was concentrated from heptanes (2×5 ml) to give compound 27 as a tan solid (68 mg, 88% yield).

Example 13—Synthesis of E-1-(5-Ethoxypyridin-2-yl)-5-(4-ethylstyryl)-1H-benzo[d]imidazole hydrochloride (Compound 18) and Z-1-(5-ethoxypyridin-2-yl)-5-(4-ethylstyryl)-1H-benzo[d]imidazole hydrochloride (Compound 19)

E-1-(5-Ethoxypyridin-2-yl)-5-(4-ethylstyryl)-1H-benzo[d]imidazole hydrochloride (compound 18) and Z-1-(5-ethoxypyridin-2-yl)-5-(4-ethylstyryl)-1H-benzo[d]imidazole hydrochloride (compound 19) were synthesized according to the following scheme:

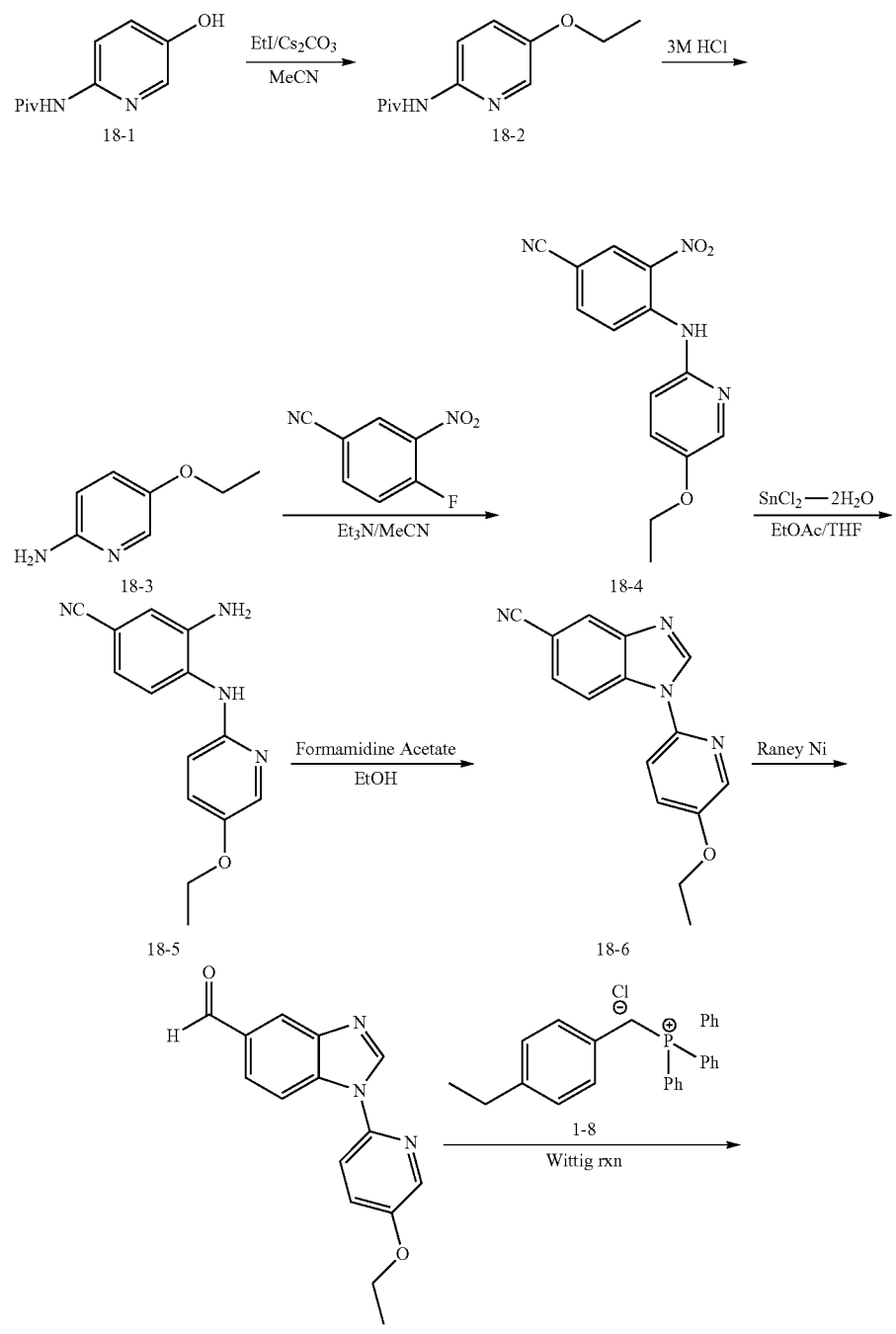

-continued

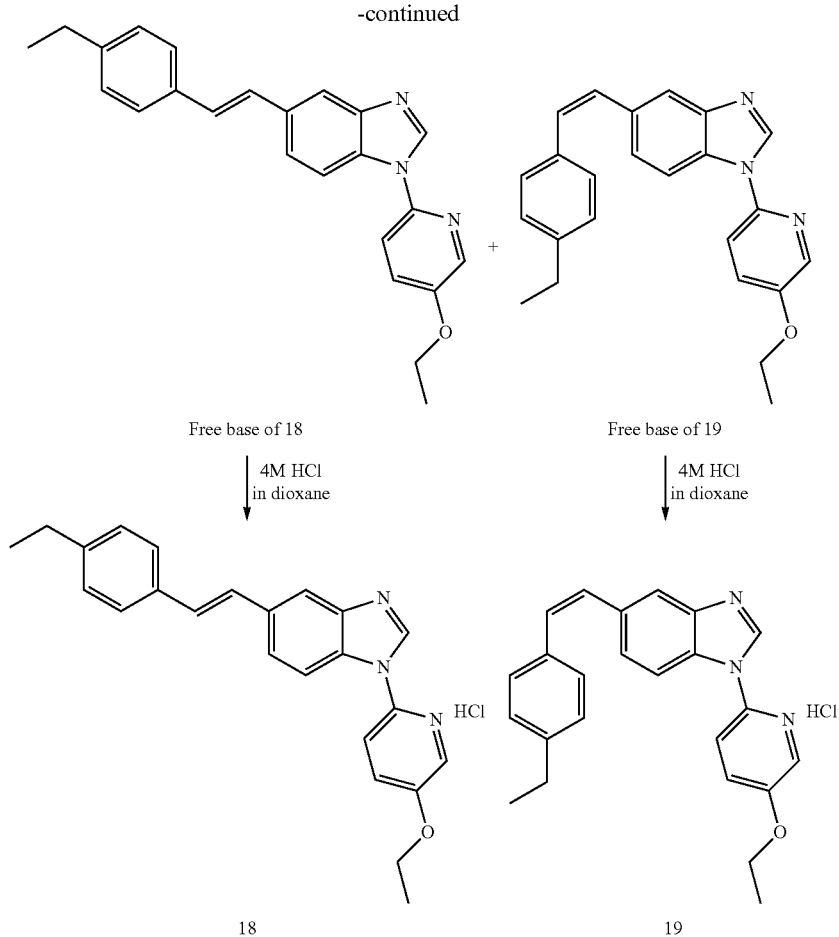

Example 13 was used as general procedure for compounds 18, 19, 20, 21 and 42. The synthesis of compound 42 required an additional step (Grignard reaction) following the installation of a methyl ester group from the Wittig reaction.

Synthesis of N-(5-Ethoxypyridin-2yl)pivalamide (Compound 18-2)

Iodoethane (4.98 g, 2.55 mL, 31.90 mmol, 1.64 equiv) was added to a suspension of N-(5-hydroxypyridin-2yl) pivalamide (18-1) (3.76 g, 19.38 mmol, 1.0 equiv) and $Cs_2CO_3$ (10.37 g, 31.94 mmol, 1.64 equiv) in acetonitrile (125 mL) and the mixture was stirred overnight. The reaction mixture was combined with that from a smaller run (from 1 g of 18-1), filtered, and the solids were washed with ethyl acetate (150 mL). The filtrate was concentrated to near dryness and the residue was partitioned between ethyl acetate (175 mL) and $H_2O$ (100 mL). The organic phase was washed with saturated brine (100 mL), dried over sodium sulfate, filtered, and concentrated under reduced pressure to give crude compound 18-2 (4.59 g, 67% yield) as a tan solid that was used in the next step.

Synthesis of 5-Ethoxypyridin-2-amine (Compound 18-3)

A mixture of crude compound 18-2 (4.59 g, 20.67 mmol, 1.0 equiv) and 3M HCl (75 mL) was refluxed with a Dean-Stark trap to collect pivalic acid that was formed. After 2 hours, the mixture was cooled to room temperature followed by an ice bath. The mixture was made basic (pH 9) by the slow addition of 6N sodium hydroxide. The mixture was extracted with ethyl acetate (1×100 mL, 1×50 mL). The combined organic layers were washed with saturated brine, dried over sodium sulfate, filtered, and concentrated under reduced pressure to give crude compound 18-3 (2.54 g, 86% yield) as a tan solid that was used in the next step.

Synthesis of 4-(5-Ethoxypyridin-2-ylamino)-3-nitrobenzonitrile (Compound 18-4)

Triethylamine (2.04 g, 2.8 mL, 20.16 mmol, 1.15 equiv) was added to a solution of crude compound 18-3 (2.54 g, 18.40 mmol, 1.05 equiv) and 4-fluoro-3-nitrobenzonitrile (2.90 g, 17.53 mmol, 1.0 equiv) in acetonitrile (70 mL). The yellow-orange solution was heated to reflux. The mixture became red-orange that deepened to red. After 4 hours, the mixture was cooled to room temperature and concentrated under reduced pressure. The residue was partitioned between ethyl acetate (300 mL) and $H_2O$ (250 mL). Some insoluble red solid was present at the interface. The organic phase was filtered to remove the small amount of red solid (LC-MS showed the solid was 18-4). The filtrate was washed with $H_2O$ (20 mL), saturated brine (100 mL), dried over sodium sulfate, filtered and concentrated under reduced pressure. The residual solid was combined with that from above, triturated with tert-butyl methyl ether, filtered and dried to give compound 18-4 (2.20 g, 42% yield, 87% purity) as a red solid.

Synthesis of 3-Amino-4-(5-ethoxypyridin-2-ylamino)-3-nitrobenzonitrile (Compound 18-5)

A red-brown solution of compound 18-4 (1.56 g, 5.5 mmol, 1.0 equiv) in a mixture of ethyl acetate (100 mL) and tetrahydrofuran (25 mL) was heated to 50° C. and $SnCl_2 \cdot 2H_2O$ (4.35 g, 19.25 mmol, 3.5 equiv) was added in portions. The mixture was heated to 60-62° C. and held for 3 hours. During the heating period, the color of the reaction mixture gradually lightened to yellow and a light suspension formed. The mixture was cooled to room temperature, quenched by the slow addition of saturated sodium bicarbonate (25 mL) and the resulting yellow suspension was stirred for 15 min. The mixture was filtered through a pad of Celite and the pad was washed with ethyl acetate (4×50 mL). The yellow filtrate was washed with saturated sodium bicarbonate (100 mL) and brine, dried over sodium sulfate and filtered. After concentration under reduced pressure, 18-5 (1.37 g, 98% yield) was isolated as a tan/brown solid that was used subsequently in the next step.

Synthesis of 1-(5-Ethoxypyridin-2-yl)-1H-benzo[d]imidazole-5-carbonitrile (Compound 18-6)

A dark-brown mixture of compound 18-5 (1.37 g, 5.39 mmol, 1.0 equiv), formamidine acetate (1.72 g, 16.5 mmol, 3.06 equiv) and ethanol (70 mL) was refluxed for 17 hours. After 1.5 hours of reflux, a light suspension had formed. The mixture was cooled to room temperature and stirred over the weekend. The gray-brown suspension was concentrated to near dryness under reduced pressure. The residual thick slurry was diluted with $H_2O$ (75 mL) and the suspension was triturated for 30 min with stirring. The suspension was filtered and the solid was washed with water (2×50 mL) and dried on the filter for 3.5 hours. After further drying in a vacuum oven at 50° C. overnight, compound 18-6 (1.31 g, 93% yield) was obtained as a brown solid.

Synthesis of 1-(5-Ethoxypyridin-2-yl)-1H-benzo[d]imidazole-5-carbaldehyde (Compound 18-7)

Compound 18-6 (0.53 g, 2.0 mmol, 1.0 equiv) was dissolved in 98% formic acid. Raney Nickel 2800 (0.66 g of very $H_2O$ wet) was suspended in $H_2O$ (4 mL) and added to the formic acid solution. The mixture was heated to reflux for 30 min. The mixture was cooled to room temperature and filtered through a pad of Celite and the pad was washed with 25% aqueous ethanol (2×25 mL). The filtrate was concentrated to a small volume under reduced pressure and diluted with $H_2O$ which caused a thick tan slurry to form. The slurry was diluted with sufficient dichloromethane (75 mL) to dissolve all solids. The biphasic mixture was made basic (pH>7) by the slow addition of saturated sodium bicarbonate, while stirring vigorously. An emulsion formed whose phases separated very slowly. The organic phase was initially dried with solid sodium chloride and the supernatant solution decanted and further dried over sodium sulfate. The mixture was filtered and concentrated under reduced pressure to give a tan/brown solid. The crude product was purified on an AnaLogix automated chromatography system (dry-loaded) eluting with a gradient of 0-5% methanol in dichloromethane to give compound 18-7 (0.35 g, 66% yield) as a pale, yellowish-tan solid.

Synthesis of E-1-(5-Ethoxypyridin-2-yl)-5-(4-ethylstyryl)-1H-benzo[d]imidazole hydrochloride (Compound 18) and Z-1-(5-ethoxypyridin-2-yl)-5-(4-ethylstyryl)-1H-benzo[d]imidazole hydrochloride (Compound 19)

A white suspension of compound 1-8 (1.09 g, 2.62 mmol, 2.0 equiv) in tetrahydrofuran (40 mL) was cooled to −55° C. and a 2.5 M solution of n-BuLi in hexanes (0.97 mL, 2.43 mmol, 1.85 equiv) was added drop-wise at −55 to −50° C. The yellow-orange, suspension was stirred 1 hour at this same temperature range. The mixture was cooled to −75° C. and compound 18-7 (0.35 g, 1.31 mmol, 1.0 equiv) was added, using tetrahydrofuran (5 mL) to rinse the flask. The mixture was allowed to warm to room temperature and stirred 17.5 hours. The tan, light suspension was concentrated to a small volume under reduced pressure and the residue was partitioned between dichloromethane (75 mL) and a sodium bicarbonate solution (50 mL). The organic phase was washed with saturated brine (50 mL), dried over sodium sulfate, filtered and concentrated under reduced pressure to give a tan viscous oil. The crude product was purified on an AnaLogix automated chromatography system (dry-loaded) eluting with a gradient of 0-60% ethyl acetate/heptanes. Fractions containing the free base of compound 18 were concentrated to give partially purified material. The white solid was repurified on an AnaLogix automated chromatography system eluting with a gradient of 0-3% methanol in dichloromethane to give a colorless film that began to crystallize. The film was dissolved in minimum volume of tert-butyl methyl ether, diluted with heptanes and the mixture slowly concentrated under reduced pressure to give the free base of compound 19 (170 mg, 35% yield) as a white solid. A 4M HCl solution in dioxane (0.4 mL) was added drop-wise to a solution of the free base of compound 19 (140 mg) in dichloromethane (20 mL). The solution was stirred at room temperature for 2 hours, diluted with toluene (10 mL) and the mixture was concentrated under reduced pressure. The residual solid was suspended in toluene (10 mL) and the suspension concentrated under reduced pressure. The solid was triturated with heptanes (10 mL), filtered, washed with heptanes (10 mL) and dried under nitrogen. The solid was further dried overnight in a vacuum oven at 40° C. to give compound 19 (134 mg) as a slightly off-white solid. Fractions containing the free base of compound 18 were concentrated under reduced pressure to give partially purified material. The viscous film was repurified on an AnaLogix automated chromatography system eluting with a gradient of 0-3% methanol in dichloromethane to give a colorless film that began to crystallize. The partially crystallized residue was triturated with a minimum volume of tert-butyl methyl ether and the suspension was diluted with heptanes followed by concentration to give the free base of compound 18 (190 mg, 44% yield) as a white solid. The HCl salt form was prepared in an analogous fashion to 19 to give 164 mg of compound 18 as a slightly off-white solid.

Example 14—Synthesis of (Z)-3-(4-Ethoxyphenyl)-6-(4-ethylstyryl)-3H-imidazo[4,5-b]pyridine (Compound 22)

(Z)-3-(4-Ethoxyphenyl)-6-(4-ethylstyryl)-3H-imidazo[4,5-b]pyridine (compound 22) was synthesized according to the following scheme:

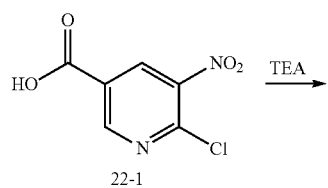
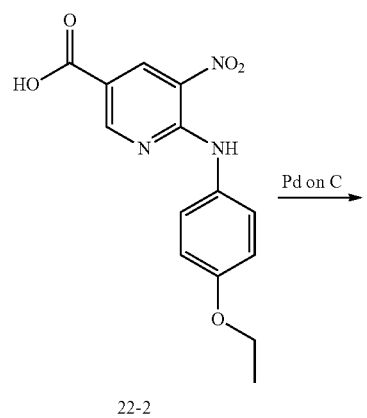
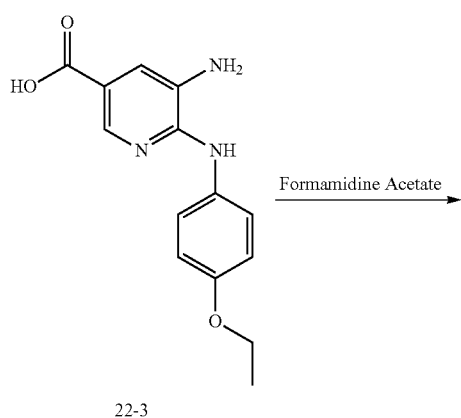
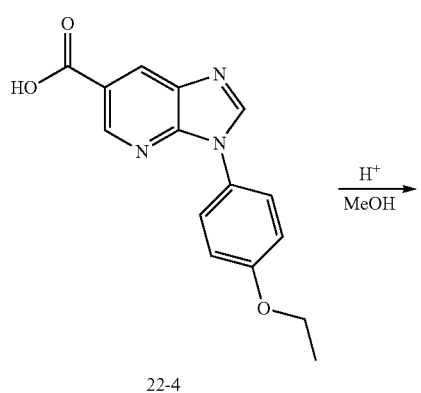
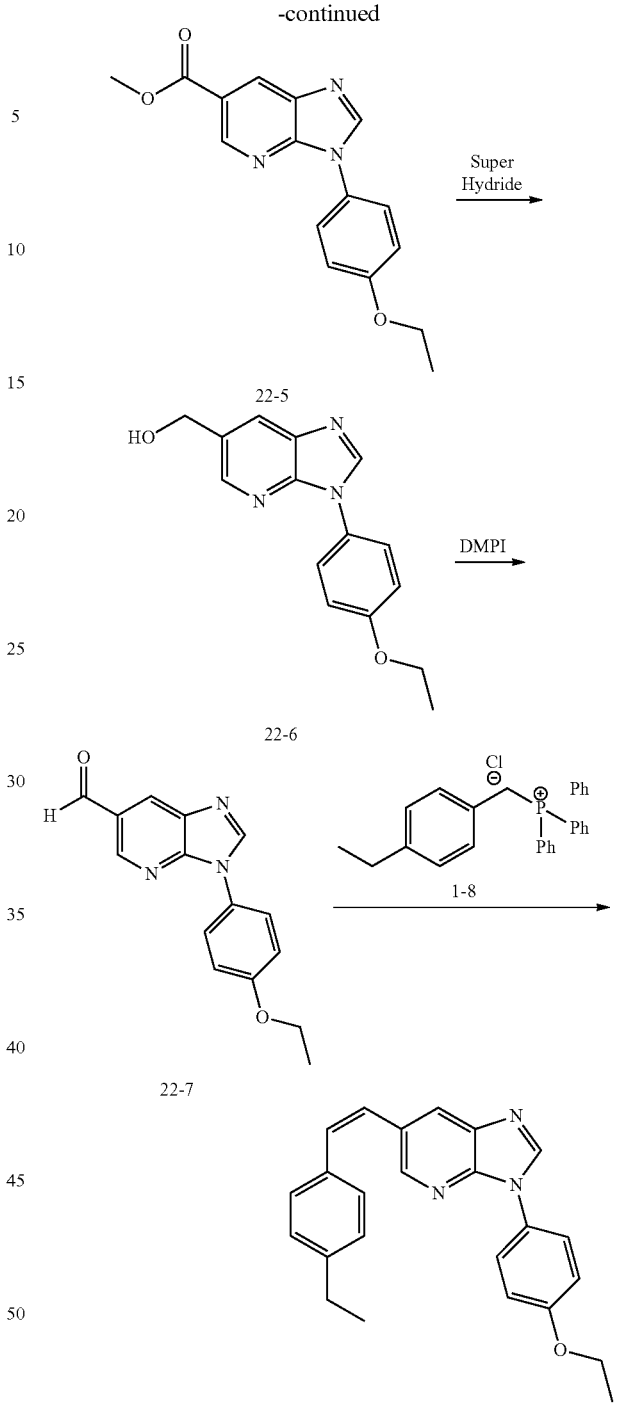
Example 14 was used as general procedure for compounds 22 and 24
Synthesis of 6-(4-Ethoxyphenylamino)-5-nitronicotinic acid (Compound 22-2)
To a solution of 6-chloro-5-nitronicotinic acid (22-1) (10 g, 49 mmol, 1.0 equiv) in acetonitrile (150 mL) was added triethylamine (15.1 mL, 109 mmol, 2.2 equiv) and 4-ethoxyaniline (6.7 mL, 52 mmol, 1.05 equiv). The mixture was heated refluxed for 18 hours and concentrated under reduced pressure. The residue was suspended in water (100 mL) and the pH adjusted to 4 with 6N hydrochloric acid. The aqueous phase was extracted with a 2:1 mixture of ethyl acetate and tetrahydrofuran (4×100 mL). The organic layers were combined, dried over sodium sulfate, and concentrated under reduced pressure to give crude compound 22-2 (14 g, 96% yield) as a black solid.

Synthesis of 3-(4-Ethoxyphenyl)-3H-imidazo[4,5-b]pyridine-6-carboxylic acid (Compound 22-4)

Crude compound 22-2 (14 g, 46.2 mmol, 1.0 equiv) was suspended in methanol (250 mL) and 20% palladium on carbon (1.5 g, 50% wet) was added. The reaction was hydrogenated @ 50 psi for 78 hours, filtered through Celite and the pad was washed with methanol (50 mL). This solution was carried on to the next step without any further workup. To this solution of 22-3 (~10 g, 33.6 mmol, 1.0 equiv) in methanol (225 ml) was added formamidine acetate (10 g, 96 mmol, 2.8 equiv). The reaction was refluxed for 18 hours. The solvent was removed under reduced pressure and water (100 mL) was added. The pH was adjusted to 4 with 6N hydrochloric acid. The aqueous phase was extracted with a mixture of 2:1 ethyl acetate and tetrahydrofuran (4×100 mL). The organic phases were combined, dried over sodium sulfate, and concentrated under reduced pressure to give compound 22-4 (8.3 g, ~75% yield) as a brown solid which was used in the next step without further purification.

Synthesis of Methyl 3-(4-ethoxyphenyl)-3H-imidazo[4,5-b]pyridine-6-carboxylate (Compound 22-5)

Compound 22-4 (3 g, 10.6 mmol, 1 equiv) was dissolved in methanol (300 mL) and sulfuric acid (0.5 mL) was added. The reaction was refluxed for 48 hours and then concentrated under reduced pressure to a slurry. The material was purified by column chromatography with 30% ethyl acetate in heptanes to give compound 22-5 (1.0 g, 32% yield) as a pale yellow oil.

Synthesis of (3-(4-Ethoxyphenyl)-3H-imidazo[4,5-b]pyridin-6-yl)methanol (Compound 22-6)

Compound 22-5 (750 mg, 2.5 mmol, 1 equiv) was dissolved in anhydrous tetrahydrofuran (20 mL) and a 1.0M super hydride solution in tetrahydrofuran (6.3 mL, 6.3 mmol, 2.5 equiv) was added. The reaction was stirred at room temperature for 1 hour and then poured into saturated ammonium chloride (100 mL). The aqueous phase was extracted with ethyl acetate (4×20 mL). The organic layers were combined, dried over sodium sulfate, and concentrated under reduced pressure. The brown residue was purified by column chromatography with a gradient of 50-100% ethyl acetate in heptanes with a final flush of ethanol to give 22-6 (600 mg, 70% yield) as a pale yellow semi-solid.

Synthesis of 3-(4-Ethoxyphenyl)-3H-imidazo[4,5-b]pyridine-6-carbaldehyde (Compound 22-7)

Compound 22-6 (570 mg, 2.1 mmol, 1 equiv) was dissolved in tetrahydrofuran (30 mL) and Dess-Martin periodinane (1 g, 2.35 mmol, 1.1 mmol) was added. The reaction was stirred at room temperature for 1 hour and then poured into saturated sodium bicarbonate. The aqueous phase was extracted with dichloromethane (4×10 mL). The organic layers were combined, dried over sodium sulfate, filtered, and concentrated under reduced pressure. The residue was triturated with methyl tert-butyl ether (2×10 mL) to give compound 22-7 (500 mg, 80% yield) as an off white solid.

Synthesis of (Z)-3-(4-Ethoxyphenyl)-6-(4-ethylstyryl)-3H-imidazo[4,5-b]pyridine (Compound 22)

Compound 1-8 (328 mg, 0.78 mmol, 1.05 equiv) was dissolved in anhydrous tetrahydrofuran (10 mL) and cooled to −78° C. A 2.5 M solution of n-Butyl lithium in hexane (315 μL, 0.78 mmol, 1.05 equiv) was added and the reaction was stirred at −78° C. for 1 hour. Then, compound 22-7 (200 mg, 0.75 mmol, 1 equiv) was added and the reaction was allowed to warm to room temperature over 2 hours. The reaction was concentrated under reduced pressure and the residue was dissolved in dichloromethane (3 mL). This solution was filtered and chromatographed on an AnaLogix 8 g column eluting with a gradient of 0-60% ethyl acetate in heptanes to give pure compound 22 (35 mg, 13% yield). An additional run was carried out to give a roughly equivalent amount of pure product.

Example 15—Synthesis of (E)-3-(4-ethoxyphenyl)-6-(4-ethylstyryl)-3H-imidazo[4,5-b]pyridine (Compound 23)

(E)-3-(4-ethoxyphenyl)-6-(4-ethylstyryl)-3H-imidazo[4,5-b]pyridine (compound 23) was synthesized according to the following scheme:

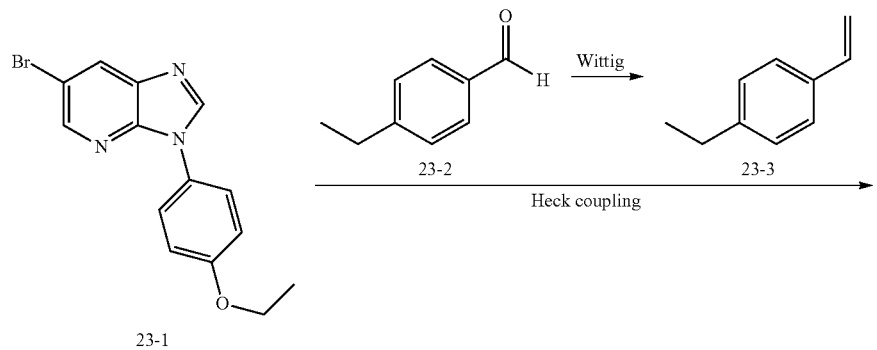

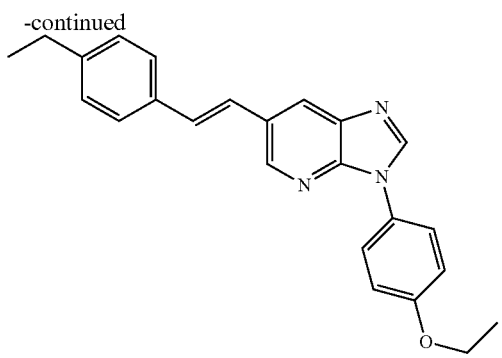

23

Example 15 was used as general procedure for compounds 3, 23 and 25

Compound 23-1 was prepared in a similar manner as compound 1-4

Synthesis of 1-Ethyl-4-vinylbenzene (Compound 23-3)

Methyltriphenylphosphonium iodide (8.08 g, 20 mmol, 1 equiv) was dissolved in anhydrous tetrahydrofuran (50 mL) and cooled to −78° C. A 2.5 M n-butyl lithium in hexane solution (8 mL, 20 mmol, 1 equiv) was added, the reaction was stirred at −78° C. for 1 hour and allowed to warm to room temperature over 1 hour. 4-Ethylbenzaldehyde (2.75 mL, 20 mmol, 1 equiv) was added as a solution in tetrahydrofuran (15 mL) and the reaction was allowed to stir at room temperature for 2 hours. The reaction was concentrated under reduced pressure and the residue was suspended in heptanes (60 mL). This suspension was filtered through basic alumina (20 g) and the pad was washed with heptanes (50 mL). The solvent was removed under reduced pressure to give compound 23-3 as a pale yellow oil (2 g, 76% yield).

Synthesis of (E)-3-(4-ethoxyphenyl)-6-(4-ethylstyryl)-3H-imidazo[4,5-b]pyridine (Compound 23)

Compound 23-1 (150 mg, 0.47 mmol, 1 equiv), compound 23-3 (187 mg, 1.42 mmol, 3 equiv) and triethylamine (1 mL) were dissolved in anhydrous dimethyl formamide (2 mL). Palladium acetate (6.3 mg, 0.028 mmol, 0.06 equiv) and tri-o-tolyl phosphine (14 mg, 0.056 mmol, 0.1 equiv) were added and the reaction was heated in the microwave at 150° C. for 1.5 hours. The reaction was poured into 1:1 mixture of water and ethyl acetate (20 mL), and the layers were separated. The aqueous phase was extracted with ethyl acetate (3×5 mL). The organic layers were combined and dried over sodium sulfate. The solvent was removed under reduced pressure and the resulting residue was chromatographed on an AnaLogix 8 g column eluting with a gradient of 0-100% ethyl acetate in heptanes to give compound 23 as an off white solid (96 mg, 55% yield).

Example 16—Synthesis of 3-(4-ethoxyphenyl)-6-[2-(4-ethylphenyl)-ethynyl]imidazo[4,5-b]pyridine (Compound 26) and 3-(4-Ethoxyphenyl)-6-(4-ethylphenethyl)-3H-imidazo[4,5-b]pyridine (Compound 28)

3-(4-ethoxyphenyl)-6-[2-(4-ethylphenyl)-ethynyl]imidazo[4,5-b]pyridine (compound 26) and 3-(4-Ethoxyphenyl)-6-(4-ethylphenethyl)-3H-imidazo[4,5-b]pyridine (compound 28) was synthesized according to the following scheme:

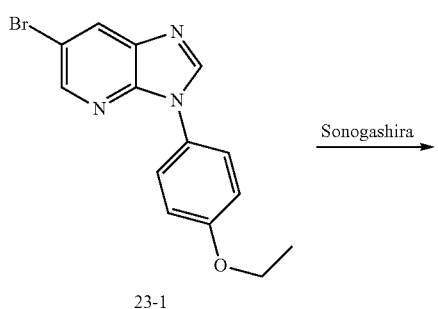

23-1

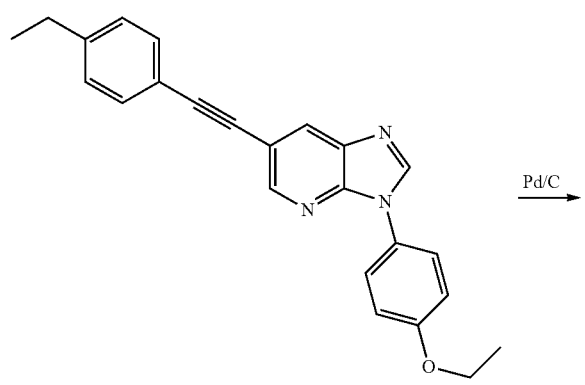

26

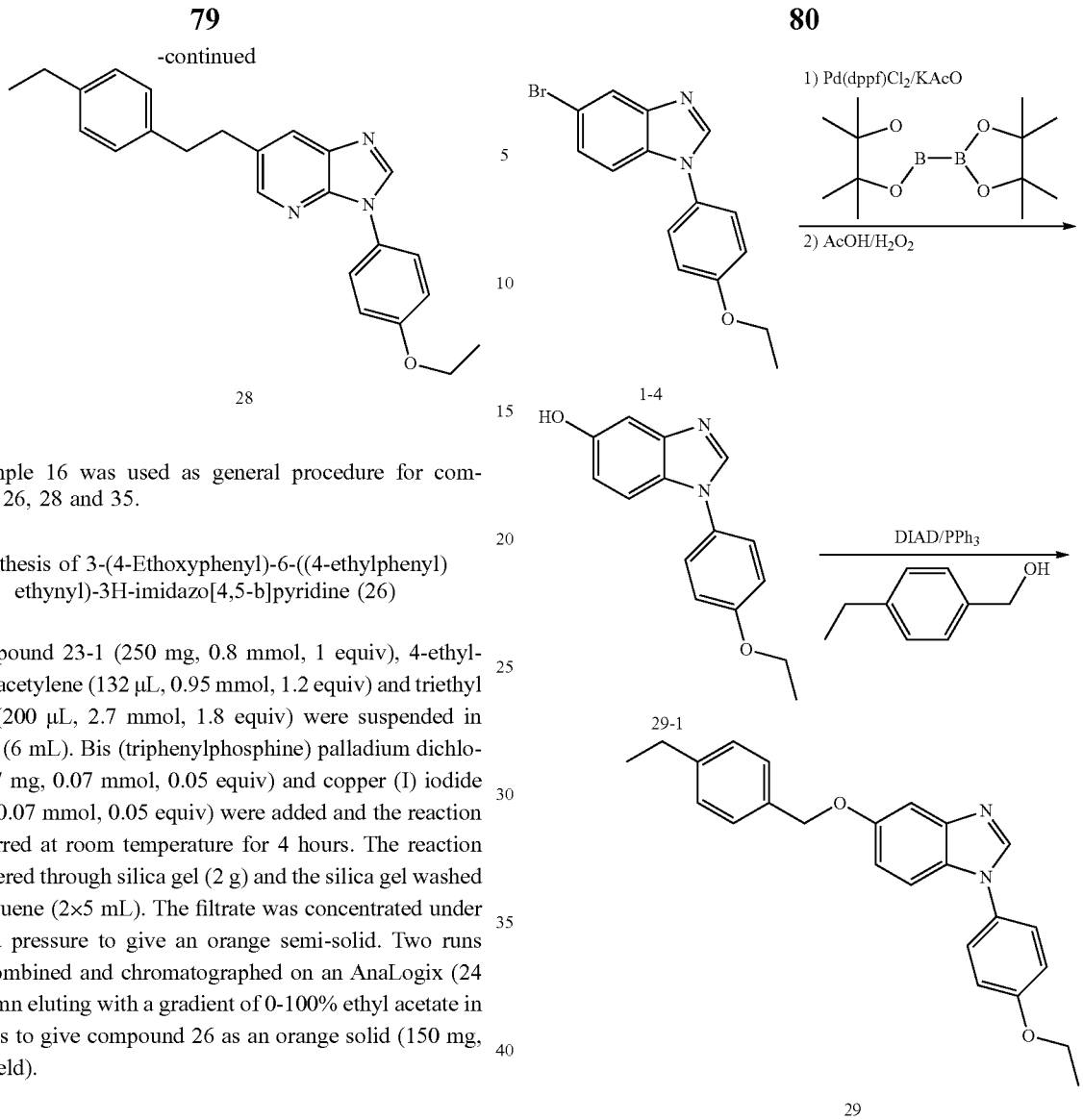

Example 16 was used as general procedure for compounds 26, 28 and 35.

Synthesis of 3-(4-Ethoxyphenyl)-6-((4-ethylphenyl)ethynyl)-3H-imidazo[4,5-b]pyridine (26)

Compound 23-1 (250 mg, 0.8 mmol, 1 equiv), 4-ethylphenyl acetylene (132 µL, 0.95 mmol, 1.2 equiv) and triethyl amine (200 µL, 2.7 mmol, 1.8 equiv) were suspended in toluene (6 mL). Bis (triphenylphosphine) palladium dichloride (27 mg, 0.07 mmol, 0.05 equiv) and copper (I) iodide (7 mg, 0.07 mmol, 0.05 equiv) were added and the reaction was stirred at room temperature for 4 hours. The reaction was filtered through silica gel (2 g) and the silica gel washed with toluene (2×5 mL). The filtrate was concentrated under reduced pressure to give an orange semi-solid. Two runs were combined and chromatographed on an AnaLogix (24 g) column eluting with a gradient of 0-100% ethyl acetate in heptanes to give compound 26 as an orange solid (150 mg, 34% yield).

Synthesis of 3-(4-Ethoxyphenyl)-6-(4-ethylphenethyl)-3H-imidazo[4,5-b]pyridine (Compound 28)

Compound 26 (100 mg, 0.27 mmol, 1 equiv) was dissolved in methanol and 20% palladium on carbon (10 mg, 50% wet) was added. The reaction was hydrogenated at 60 psi for 96 hours. During this time, additional catalyst (5 mg) was added on two occasions to complete the reduction. When the reaction was shown to be complete, it was filtered through Celite and the pad was washed with methanol (10 mL). The solution was concentrated and the residue was triturated with heptanes (3×1 mL) to give compound 28 as a tan solid (54 mg, 52% yield).

Example 17—Synthesis of 1-(4-Ethoxyphenyl)-5-(4-ethylbenzyloxy)-1H-benzo[d]imidazole (Compound 29)

1-(4-Ethoxyphenyl)-5-(4-ethylbenzyloxy)-1H-benzo[d]imidazole (compound 29) was synthesized according to the following scheme:

Example 17 was used as general procedure for compounds 29, 31 and 32.

Synthesis of 1-(4-Ethoxyphenyl)-1H-benzo[d]imidazol-5-ol (Compound 29-1)

Compound 1-4 (0.3 g, 0.9 mmol, 1.0 equiv) was dissolved in dioxane (150 mL) and then bis(pinacolato)diboron (0.3 g, 1.1 mmol, 1.2 equiv), potassium acetate (0.2 g, 1.9 mmol, 2.0 equiv), and [1,1'-bis(diphenylphosphino)ferrocene]-palladium dichloride complex with dichloromethane (40 mg, 0.05 mmol, 0.05 equiv) were added in succession. The reaction was degassed under a stream of nitrogen for 10 minutes and refluxed overnight. The reaction was filtered through Celite and which was then washed with ethyl acetate (50 mL). The solvent was evaporated under reduced pressure and the residue was dissolved in tetrahydrofuran (20 mL). The solution was cooled to 0° C. and glacial acetic acid (90 µL, 1.4 mmol, 1.5 equiv) was added dropwise. The mixture was stirred at 0° C. for 1 h, at which time an aqueous solution of hydrogen peroxide (30% wt. in water, 220 µL, 1.9 mmol, 2 equiv) was added slowly. The reaction mixture was stirred for 5 h, at which time LC-MS showed the reaction was completed and the mixture was diluted with water. The aqueous phase was discarded and the organic layer was treated with an aqueous solution of sodium sulfite (0.2 g, 1.9 mmol, 2 equiv) and stirred at room temperature for 15 minutes. The organic phase was separated and dried over sodium sulfate. The solvent was evaporated under reduced pressure to give compound 29-1 as a red solid (0.3 g, quantitative yield) which was used in the next step without further purification.

Synthesis of 1-(4-Ethoxyphenyl)-5-(4-ethylbenzyloxy)-1H-benzo[d]imidazole (Compound 29)

To a solution of triphenylphosphine (0.5 g, 2.0 mmol, 2.0 equiv) in tetrahydrofuran (10 mL) at 0° C. was added diisopropyldiazocarboxylate (0.4 mL, 2.0 mmol, 2.0 equiv) dropwise. The mixture was stirred at 0° C. for 50 minutes. At this time, a solution of compound 29-1 (0.3 mL, 1.0 mmol, 1.0 equiv) and 4-ethylbenzyl alcohol (0.2 mL, 1.1 mmol, 1.1 equiv) in tetrahydrofuran (10 mL) was added slowly. The reaction was stirred at room temperature overnight at which time LC-MS indicated the reaction was complete. The mixture was concentrated under reduced pressure and absorbed on silica gel (3 g). The compound was purified on an AnaLogix (SF 15-24 g) column eluting with a gradient of from 10-60% ethyl acetate in heptanes for 30 minutes followed by 100% ethyl acetate for 5 minutes to give compound 29 as a tan solid (77 mg, 21% yield).

Example 18—Synthesis of 5-(4-Isopropylbenzyloxy)-1-(4-methoxyphenyl)-1H-benzo[d]imidazole (Compound 30)

5-(4-Isopropylbenzyloxy)-1-(4-methoxyphenyl)-1H-benzo[d]imidazole (compound 30) was synthesized according to the following scheme:

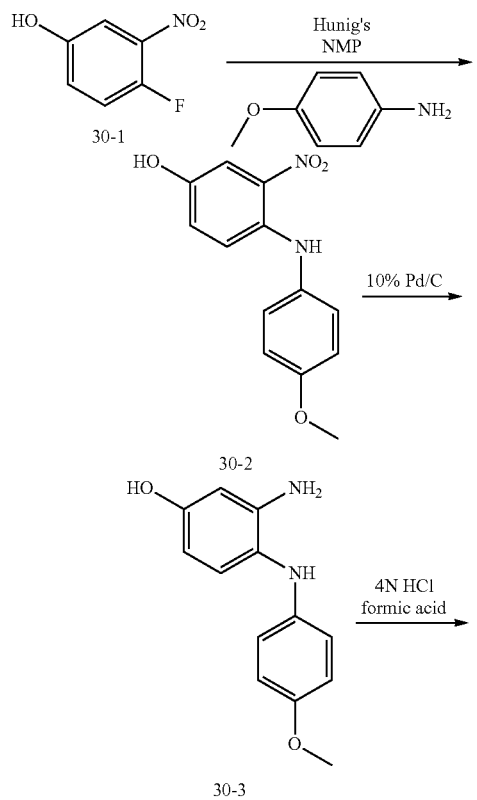

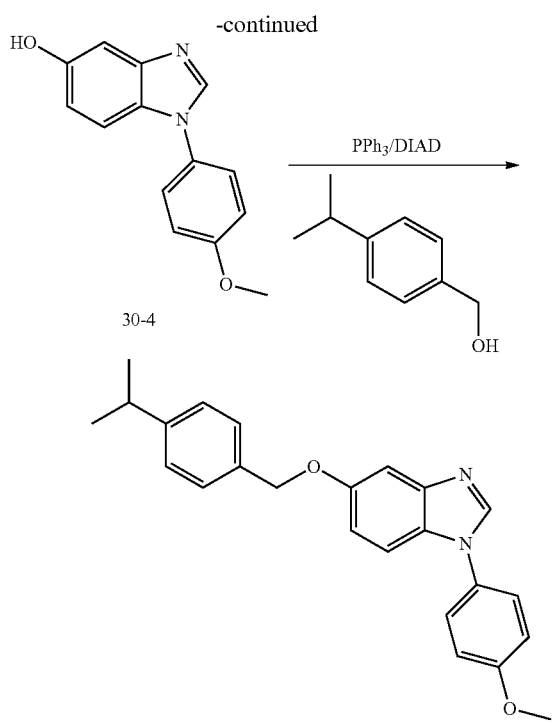

Synthesis of 4-(4-Methoxyphenylamino)-3-nitrophenol (Compound 30-2)

To a solution of 4-fluoro-3-nitrophenol (2.0 g, 13 mmol, 1.0 equiv) in N-methyl-2-pyrrolidone (10 ml) was added N,N-diisopropylethylamine (2.2 mL, 13 mmol, 1.0 equiv) and 4-methoxyaniline (1.9 g, 15 mmol, 1.2 equiv). The mixture was heated to 165° C. overnight, at which time LC-MS indicated that the reaction was complete. The mixture was cooled to room temperature and diluted with ethyl acetate. The organic phase was washed with water, saturated brine, dried over sodium sulfate and evaporated under reduced pressure. The compound was purified on an AnaLogix (SF 40-150 g) column using a gradient of 0-50% ethyl acetate in heptanes over 45 minutes to give compound 30-2 as a red solid (2.2 g, 67% yield).

Synthesis of 3-Amino-4-(4-methoxyphenylamino)phenol (Compound 30-3)

Compound 30-2 (2.2 g, 8.5 mmol, 1.0 equiv) was dissolved in ethyl acetate (200 mL) and 10% Pd/C (0.44 g, 50% wet with water) was added. The reaction was hydrogenated at 20 psi for 4 h until hydrogen consumption was complete. The material was filtered through Celite and the pad was washed with ethyl acetate (200 mL). The filtrate was concentrated under reduced pressure to give compound 30-3 as a dark red oil (2.0 g, quantitative yield).

Synthesis of 1-(4-Methoxyphenyl)-1H-benzo[d]imidazol-5-ol (Compound 30-4)

Compound 30-3 (1.0 g, 4.3 mmol, 1.0 equiv) was suspended in 4 N aqueous hydrochloric acid (10 mL) and formic acid (1.3 mL) was added. The reaction was heated in a sealed tube at 100° C. for 2 h, at which time LC-MS indicated the reaction was complete. The reaction was cooled to room temperature and diluted with water (30 mL). The pH of the mixture was adjusted to 8 with solid sodium bicarbonate and extracted with ethyl acetate (3×50 mL). The organic layers were combined, dried over sodium sulfate, and evaporated under reduce pressure. The crude solid was triturated with methyl tert-butyl ether to give compound 30-4 as a dark red solid (0.9 g, 87% yield).

Synthesis of 5-(4-Isopropylbenzyloxy)-1-(4-methoxyphenyl)-1H-benzo[d]imidazole (Compound 30)

This procedure is analogous to the one used for the conversion of compound 29-1 to compound 29. The compound was purified on an AnaLogix (SF 25-40 g) column using a gradient of 0-70% ethyl acetate in heptanes over 35 minutes to give compound 30 as a tan solid (0.2 g, 28% yield).

Example 19—Synthesis of 1-(4-Ethoxyphenyl)-5-(4-ethylbenzylthio)-1H-benzo[d]imidazole (Compound 33)

1-(4-Ethoxyphenyl)-5-(4-ethylbenzylthio)-1H-benzo[d]imidazole (compound 33) was synthesized according to the following scheme:

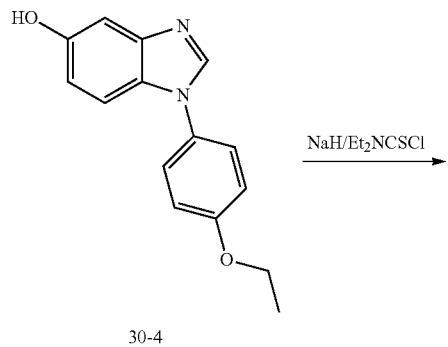

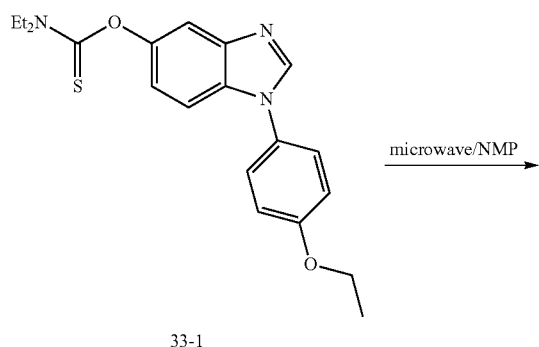

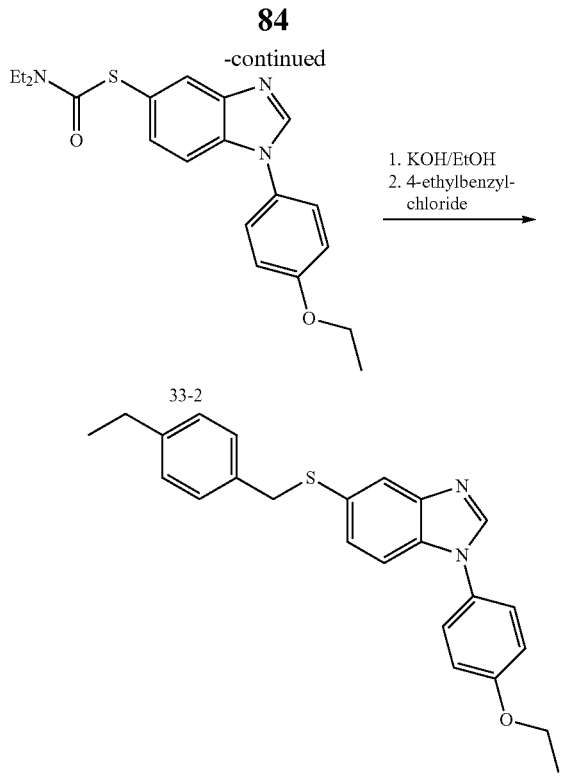

Synthesis of O-1-(4-Ethoxyphenyl)-1H-benzo[d]imidazol-5-yl diethylcarbamothioate (Compound 33-1)

A solution of compound 30-4 (0.4 g, 1.6 mmol, 1.0 equiv) in tetrahydrofuran/dimethylformamide (1:1, 10 mL) was added dropwise to a suspension of sodium hydride (60% dispersion in mineral oil) (77 mg, 1.9 mmol, 1.2 equiv) in tetrahydrofuran (5 mL). After 10 minutes, diethylthiocarbamoyl chloride (0.3 g, 1.8 mmol, 1.1 equiv) was added and the reaction heated at 60° C. for 5 h. The cooled mixture was poured in 1N aqueous sodium hydroxide (20 mL) and extracted with ethyl acetate (3×20 mL). The organic layers were combined, dried with sodium sulfate and evaporated under reduced pressure. The compound was purified on an AnaLogix (SF 15-24 g) column eluting with a gradient of 30-100% ethyl acetate in heptanes over 40 minutes to give compound 33-1 as a brown oil (0.4 g, 65% yield).

Synthesis of S-1-(4-Ethoxyphenyl)-1H-benzo[d]imidazol-5-yl diethylcarbamothioate (Compound 33-2)

A solution of compound 33-1 (0.5 g, 1.5 mmol, 1.0 equiv) in N-methyl-2-pyrrolidone (4 ml) was placed in the microwave (250 W) and heated at 250° C. for 1.5 h, at which time TLC indicated the reaction was complete. The mixture was cooled to room temperature and diluted with ethyl acetate (20 mL). The organic phase was washed with water (2×20 mL), dried over sodium sulfate and evaporated under reduced pressure. The compound was purified on an AnaLogix (SF 15-24 g) column eluting with a gradient of 0-60% ethyl acetate in heptanes to give compound 33-2 as a brown oil (0.13 g, 23% yield).

Synthesis of 1-(4-Ethoxyphenyl)-5-(4-ethylbenzyl-thio)-1H-benzo[d]imidazole (Compound 33)

A solution of compound 33-2 (0.13 g, 0.35 mmol, 1.0 equiv) in ethanol (10 mL) was treated with 6 N aqueous potassium hydroxide (5 mL). The reaction was heated at reflux overnight, at which time LC-MS indicated the reaction was complete (Note: the m/z observed on the LC-MS corresponded to 1,2-bis(1-(4-ethoxyphenyl)-1H-benzo[d]imidazol-5-yl)disulfane). The solvents were evaporated under reduced pressure, and the residue was dissolved in ethanol (20 mL). The mixture was treated with excess sodium borohydride (200 mg) and stirred at room temperature until no more disulfide product was observed via LC-MS. 4-Ethylbenzyl chloride (61 mg, 0.39 mmol, 1.1 equiv) was added and the mixture was stirred at room temperature overnight. The solvent was evaporated under reduced pressure and the residue was diluted with ethyl acetate. The organic layer was washed with saturated aqueous sodium bicarbonate, dried over sodium sulfate, and evaporated under reduce pressure. The compound was purified on an AnaLogix (SF 10-8 g) column eluting with a gradient of 0-35% ethyl acetate in heptanes over 25 minutes to give compound 33 as an off white solid (50 mg, 10% yield).

Example 20—Synthesis of N-((1-(4-Ethoxyphenyl)-1H-benzo[d]imidazol-5-yl)methyl)-4-ethylaniline (Compound 34)

N-((1-(4-Ethoxyphenyl)-1H-benzo[d]imidazol-5-yl)methyl)-4-ethylaniline (compound 34) was synthesized according to the following scheme:

Synthesis of N-((1-(4-Ethoxyphenyl)-1H-benzo[d]imidazol-5-yl)methyl)-4-ethylaniline (Compound 34)

To a solution of compound 1-6 (1 g, 3.8 mmol, 1 equiv.) in 30 mL of methanol was added 4-ethylaniline (455 mg, 3.8 mmol, 1 equiv.) via an addition funnel. Upon completion of the addition, the reaction was heated to 60° C. for 1 h and then allowed to cool to room temperature. Upon reaching room temperature, sodium borohydride (143 mg, 3.8 mmol, 1 equiv.) was added slowly and stirred at room temperature for 30 minutes. A saturated solution of sodium bicarbonate (10 mL) was added followed by stirring for 20 minutes. The reaction was diluted with dichloromethane (50 mL), the organic layer was separated, dried over sodium sulfate and concentrated under reduced pressure. The resulting material was dry loaded onto an AnaLogix (80 g) column and eluted with a gradient of 25-100% ethyl acetate in heptanes to give compound 34 as a white solid (430 mg, 31% yield).

Example 21—Synthesis of 5-[2-(4-tert-butylphenyl)-cyclopropyl]-1-(4-isopropoxyphenyl)-benzimidazole (Compound 36)

5-[2-(4-tert-butylphenyl)cyclopropyl]-1-(4-isopropoxyphenyl)-benzimidazole (compound 36) was synthesized according to the following scheme:

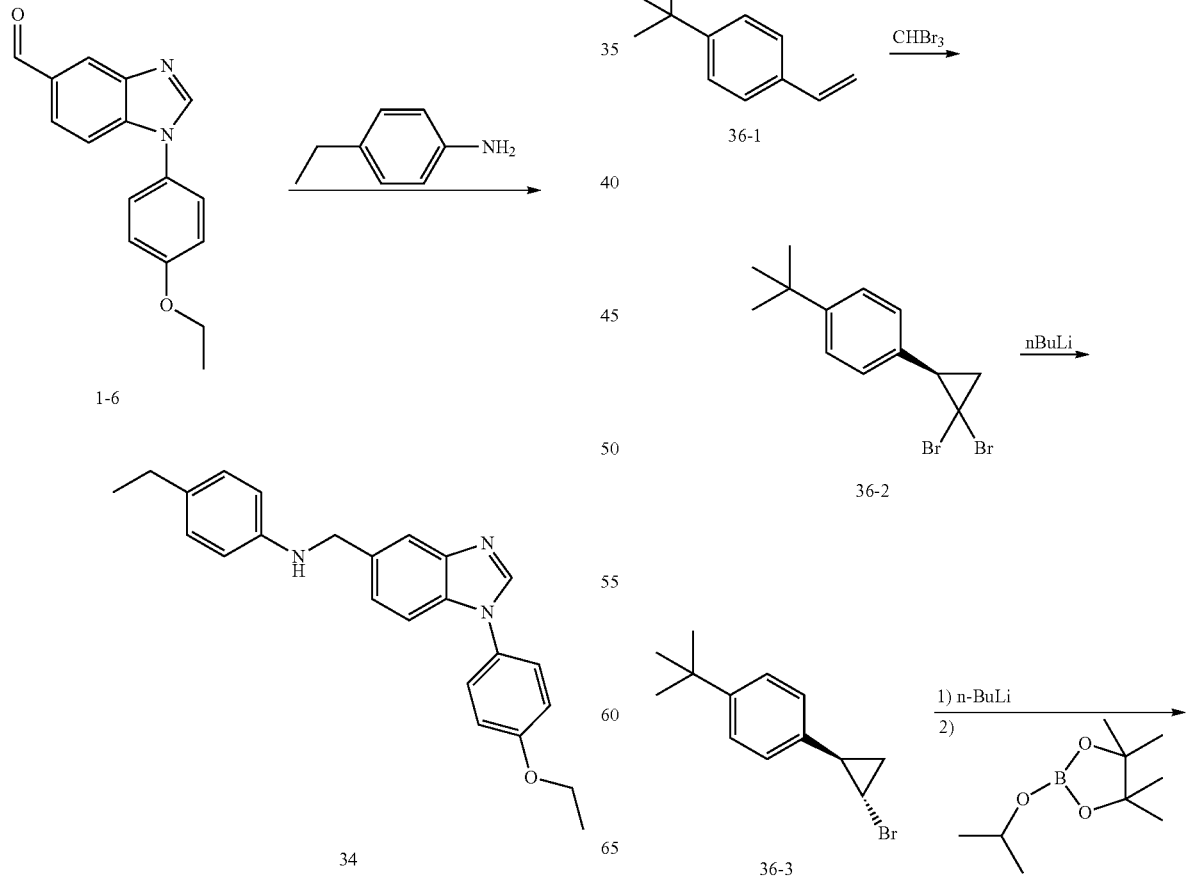

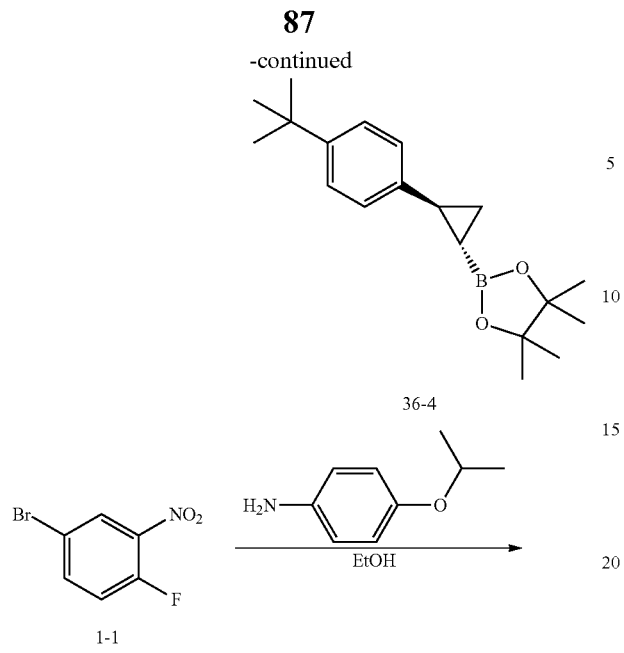

Synthesis of 1-(tert-Butyl)-4-(2,2-dibromocyclopropyl)-benzene (Compound 36-2)

A solution of 1-(tert-butyl)-4-vinylbenzene (36-1) (29.1 g, 182 mmol, 1 equiv) and benzyltriethylammonium bromide (1.2 g, 4.4 mmol, 0.02 equiv) in bromoform (135 mL, 1.55 mol, 8.5 equiv) was cooled to 0° C. With vigorous mechanical stirring, a 50% aqueous sodium hydroxide (145 mL, 2.77 mol, 23 equiv) was added in one portion (caution: exothermic; temperature reached 60° C.) resulting in the formation of a thick tan suspension. Stirring was continued for 2 hours while the reaction returned to room temperature at which point GC-MS indicated the reaction was complete. The reaction mixture was diluted with methyl tert-butyl ether (200 mL) and filtered. The filtrate was transferred to a separatory funnel and the layers were separated. The aqueous layer was extracted with methyl tert-butyl ether (2×200 mL). The combined organic layers were washed with saturated brine (500 mL), dried over sodium sulfate, filtered, and evaporated under reduced pressure to a brown liquid (90 g). The crude material was passed through a plug of silica gel (300 g) eluting with heptanes to give 36-2 (67 g, quantitative yield) as a slightly yellow liquid.

Synthesis of (trans)-1-(2-Bromocyclopropyl)-4-(tert-butyl)benzene (36-3)

A 2.5M solution of n-butyl lithium in hexane (22 mL, 55 mmol, 1.1 equiv) was added at such a rate keeping the temperature below −70° C. to a solution of 36-2 (16.6 g, 50 mmol, 1 equiv) in tetrahydrofuran (250 mL). Upon completion of the addition, the reaction was stirred for 2 hours at −78° C. GC-MS of a reaction aliquot quenched into methanol indicated 10% stating material remained along with a 1:1 mixture of trans and cis isomers. Additional 2.5 M n-butyl lithium in hexane (2 mL) was added and the reaction was stirred an additional 1 hour at −78° C. The reaction was quenched at −78° C. by the addition of acetic acid (3 mL) in tetrahydrofuran (30 mL). The mixture was warmed to room temperature, diluted with methyl tert-butyl ether (300 mL) and extracted with 1 N HCl (300 mL). The organic layer was washed with saturated brine (300 mL), dried over sodium sulfate, filtered, and evaporated under reduced pressure. The crude material was purified on an AnaLogix automated chromatography system eluting with heptanes. The desired trans isomer eluted first followed immediately by the cis isomer with several mixed fractions in between. After evaporation, 36-3 was recovered as a colorless liquid (3.3 g, 26% yield). The cis isomer was also recovered (2.9 g, 23% yield). Note: The determination of the relative stereochemistry (cis vs. trans) was done by comparing coupling constants of the cyclopropane ring protons ($J_{cis} > J_{trans}$).

Synthesis of 2-((trans)-2-(4-(tert-Butyl)phenyl)-cyclopropyl)-4,4,5,5-tetramethyl-1,3,2-dioxaborolane (36-4)

A 2.5M solution of n-butyl lithium in hexane (5 mL, 12.4 mmol, 1.5 equiv) was added to a solution of 36-3 (2.1 g, 8.2 mmol, 1 equiv) in tetrahydrofuran (100 mL) at −78° C. The mixture was stirred at −78° C. for 1 hour. Once completion of the lithium/halogen exchange was confirmed by GC-MS of a reaction aliquot quenched into methanol, 2-isopropoxy-4,4,5,5-tetramethyl-1,3,2-dioxaborolane (2.6 mL, 12.4 mmol, 1.5 equiv) was added in one portion (caution: exothermic; temperature reached −50° C.). Stirring was continued for 2 hours while warming to room temperature. The reaction was quenched by the addition of saturated ammonium chloride (200 mL) and extracted with methyl tert-butyl ether (250 mL). The organic layer was washed with saturated brine (150 mL), dried over sodium sulfate, filtered, and evaporated under reduced pressure to give 36-4 [3.2 g, quantitative yield, 85% purity (major impurity is pinacol)] which forms a white semi-solid upon storage at −20° C.

Synthesis of 5-Bromo-1-(4-isopropoxyphenyl)-1H-benzo[d]imidazole (36-7)

Compound 36-7 was prepared from compound 1-1 in a similar fashion to that used to synthesize compound 1-4.

Synthesis of 5-((trans)-2-(4-(tert-Butyl)phenyl)-cyclopropyl)-1-(4-isopropoxyphenyl)-1H-benzo[d]imidazole (36)

A 100 mL round bottom flask was charged with 36-4 (1.5 g, 5 mmol, 1.5 equiv), 36-7 (1.1 g, 3.3 mmol, 1 equiv), tripotassium phosphate dihydrate (3.46 g, 15 mmol, 4.5 equiv), tricyclohexyl phosphine (280 mg, 1.0 mmol, 0.33 equiv), toluene (20 mL), and water (2 mL). The mixture was degassed with a stream of nitrogen for 10 minutes. Palladium (II) acetate (113 mg, 0.5 mmol. 0.15 equiv) was added and the reaction was degassed with a stream of nitrogen for an additional 5 minutes. The reaction was refluxed for 24 hours, cooled to room temperature and filtered through a pad of Celite, washing with methyl tert-butyl ether. The filtrate was transferred to a separatory funnel and washed with water (100 mL), saturated brine (100 mL), dried over sodium sulfate, filtered, and evaporated under reduced pressure. The crude material was purified on an AnaLogix automated chromatography system eluting with a gradient of 0-3% methanol in dichloromethane which removed baseline impurities. The material was further purified on an AnaLogix automated chromatography system eluting with a gradient of 0-15% acetone in toluene to give 36 (370 mg, 27% yield) as a yellow glass.

Example 22—Synthesis of methyl 4-[(Z)-2-[1-(4-isopropoxyphenyl)-benzimidazol-5-yl]vinyl]benzoate (Compound 37), 2-[4-[(Z)-2-[1-(4-isopropoxyphenyl)-benzimidazol-5-yl]vinyl]phenyl]-propan-2-ol (Compound 38), and 5-[(Z)-2-[4-(1-fluoro-1-methyl-ethyl)phenyl]vinyl]-1-(4-isopropoxy-phenyl)benzimidazole (Compound 39)

Methyl 4-[(Z)-2-[1-(4-isopropoxyphenyl)-benzimidazol-5-yl]vinyl]benzoate (compound 37), 2-[4-[(Z)-2-[1-(4-isopropoxyphenyl)benzimidazol-5-yl]vinyl]phenyl]-propan-2-ol (compound 38), and 5-[(Z)-2-[4-(1-fluoro-1-methyl-ethyl)phenyl]-vinyl]-1-(4-isopropoxy-phenyl)benzimidazole (compound 39) were synthesized according to the following scheme:

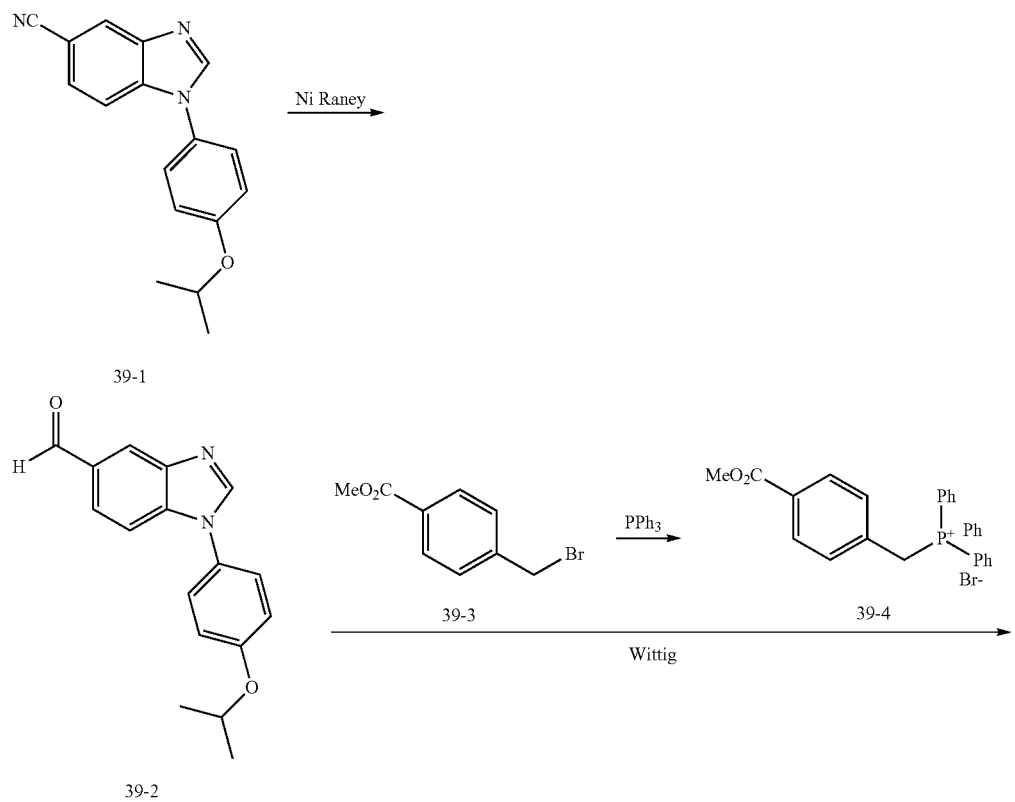

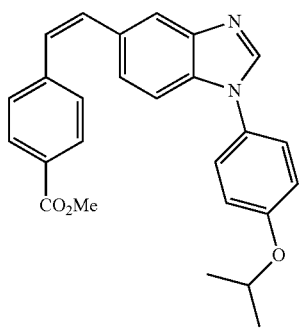

37

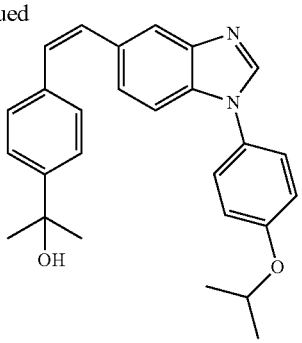

38

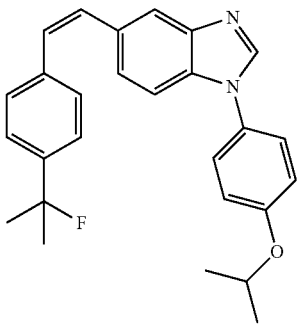

39

Note that compound 41 was formed as a by-product during the Wittig reaction to form compound 38. Compound 45 was isolated following saponification of compound 37. Additionally, compound 61 was synthesized in a similar fashion as compound 38.

Synthesis of 1-(4-Isopropoxyphenyl)-1H-benzo[d]imidazole-5-carbaldehyde (39-2)

A suspension of Raney Nickel (6 g) in water (35 mL) was added to a stirred solution of compound 39-1 (4.9 g, 18 mmol, 1.0 equiv) in formic acid (35 mL). The reaction was refluxed for 2 hours, at which point LC-MS analysis indicated the reaction was complete. The mixture was cooled to room temperature, diluted with dichloromethane (100 mL) and water (100 mL) and filtered through Celite. The layers were separated and the aqueous portion was extracted with dichloromethane (2×50 mL). The combined organic layers were dried over sodium sulfate, filtered, and evaporated under reduced pressure. The residue was purified on an AnaLogix (SF 40-115 g) column eluting with a gradient of 0-3.5% methanol in dichloromethane to give compound 39-2 as a white solid (3.5 g, 72% yield).

Synthesis of (4-(Methoxycarbonyl)benzyl)triphenyl-phosphonium bromide (39-4)

Compound 39-4 was prepared from compound 39-3 using a similar procedure to that used to synthesize compound 1-8.

Synthesis of (Z)-Methyl 4-(2-(1-(4-isopropoxyphenyl)-1H-benzo[d]imidazol-5-yl)vinyl)benzoate (37)

Compound 39-4 (5.9 g, 12 mmol, 1.0 equiv) was suspended in anhydrous tetrahydrofuran (200 mL) and cooled to −78° C. A 2.5 M solution of n-butyl lithium in hexane (5 mL, 13 mmol, 1.05 equiv) was added and the reaction was stirred at −78° C. for 1 hour. Compound 39-2 (3.4 g, 12 mmol, 1.0 equiv) was added and the reaction was allowed to warm to room temperature. After 12 hours, LC-MS indicated the reaction was 80% completed. The reaction was concentrated to dryness under reduced pressure. The residue was purified on an AnaLogix (SF 40-150 g) column eluting with a gradient of 0-100% ethyl acetate in heptanes to give compound 37 (2.6 g, 49% yield) as a light yellow oil.

Synthesis of (Z)-2-(4-(2-(1-(4-Isopropoxyphenyl)-1H-benzo[d]imidazol-5-yl)vinyl)phenyl)propan-2-ol (38)

A 3.0M solution of methylmagnesium bromide in tetrahydrofuran (6.1 mL, 18 mmol, 3.0 equiv) was added at room temperature to a solution of compound 37 (2.5 g, 6.1 mmol, 1.0 equiv) in anhydrous tetrahydrofuran (100 mL). After 3 hours, LC-MS indicated the reaction was completed. The reaction was quenched with an ice cold saturated ammonium chloride. The layers were separated and the aqueous portion was extracted with ethyl acetate (2×100 mL). The combined organic layers were dried over sodium sulfate, filtered, and evaporated under reduced pressure. The residue was purified on an AnaLogix (SF 40-115 g) column eluting with a gradient of 0-3.5% methanol in dichloromethane to give compound 38 as an light yellow oil (1.7 g, 68% yield).

Synthesis of (Z)-5-(4-(2-Fluoropropan-2-yl)styryl)-1-(4-isopropoxyphenyl)-1H-benzo[d]imidazole (39)

Diethylaminosulfur trifluoride (0.18 mL, 1.3 mmol, 1.3 equiv) was added to a solution of compound 38 (0.4 g, 0.97 mmol, 1.0 equiv) in dichloromethane (50 mL) at 0° C. The reaction was allowed to warm to room temperature and after 3 hours LC-MS indicated the reaction was complete. The reaction was quenched with water and diluted with dichloromethane. The layers were separated and the aqueous portion was extracted with dichloromethane (2×50 mL). The combined organic layers were dried over sodium sulfate, filtered, and evaporated under reduced pressure. The residue was purified by preparative HPLC using a gradient of 0%-95% water (0.1% formic acid) in acetonitrile (0.1% formic acid) to give compound 39 (120 mg) as a light yellow oil.

Example 23—Synthesis of 5-[(Z)-2-(4-isopropenyl-phenyl)-vinyl]-1-(4-isopropoxyphenyl)-benzimidazole (Compound 40)

5-[(Z)-2-(4-isopropenylphenyl)-vinyl]-1-(4-isopropoxyphenyl)-benzimidazole (compound 40) was synthesized according to the following scheme:

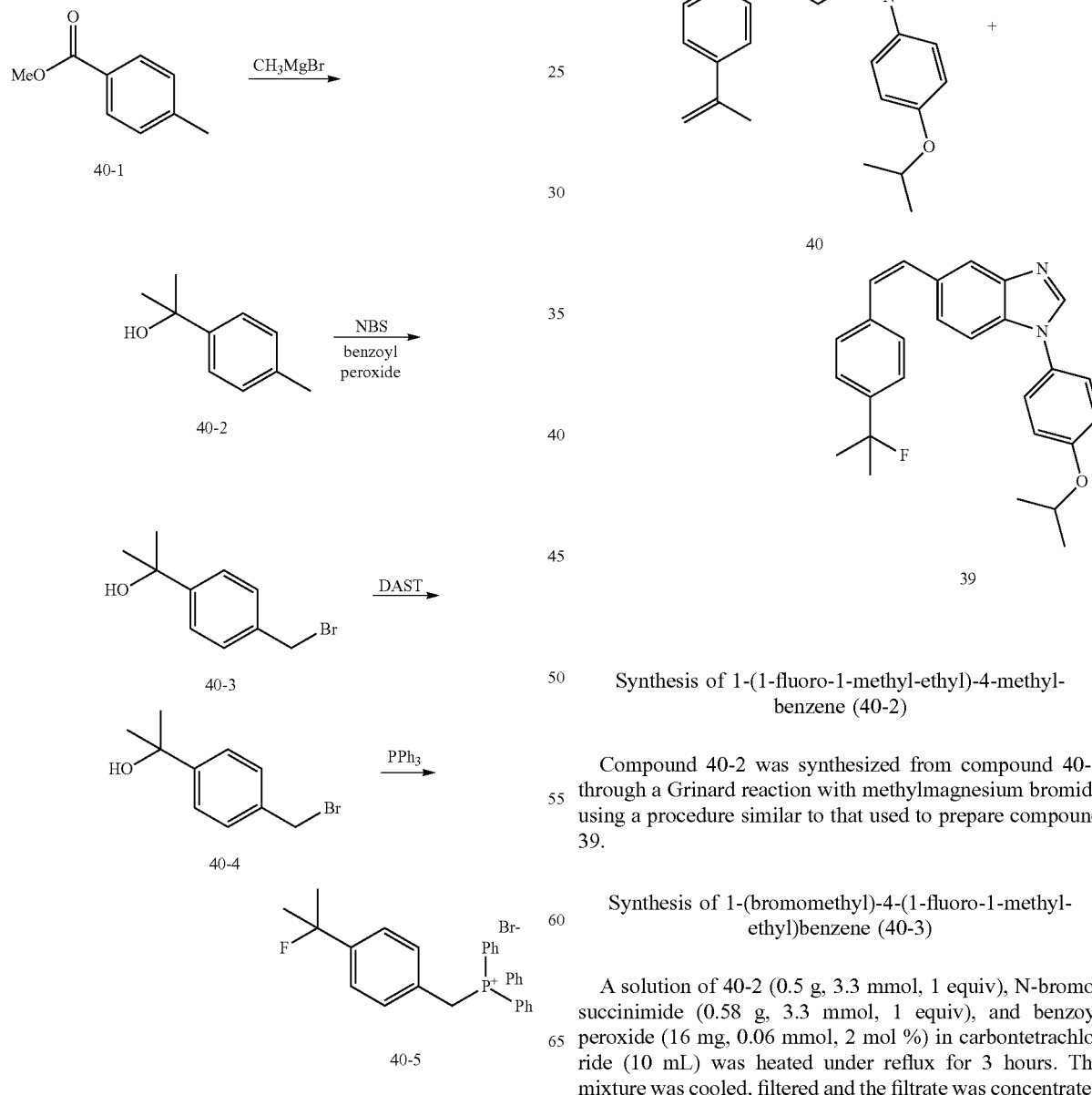

Synthesis of 1-(1-fluoro-1-methyl-ethyl)-4-methyl-benzene (40-2)

Compound 40-2 was synthesized from compound 40-1 through a Grinard reaction with methylmagnesium bromide using a procedure similar to that used to prepare compound 39.

Synthesis of 1-(bromomethyl)-4-(1-fluoro-1-methyl-ethyl)benzene (40-3)

A solution of 40-2 (0.5 g, 3.3 mmol, 1 equiv), N-bromo-succinimide (0.58 g, 3.3 mmol, 1 equiv), and benzoyl peroxide (16 mg, 0.06 mmol, 2 mol %) in carbontetrachloride (10 mL) was heated under reflux for 3 hours. The mixture was cooled, filtered and the filtrate was concentrated under reduced pressure. Ethyl acetate (20 mL) and water (20 mL) were added and the layers were separated. The organic portion was dried with sodium sulfate, filtered and concentrated under reduced pressure to afford compound 40-3 (0.3 g, 45% yield).

Synthesis of [4-(1-fluoro-1-methyl-ethyl)phenyl]methyl-triphenyl-phosphonium bromide (40-5)

Compound 40-5 was prepared by reacting compound 40-3 with diethylaminosulfur trifluoride using a procedure similar to that used for compound 37 followed by treatment with triphenylphosphine similar to the procedure utilized to synthesize compound 1-8.

Synthesis of 5-[(Z)-2-(4-isopropenylphenyl)-vinyl]-1-(4-isopropoxyphenyl)-benzimidazole (40)

Compound 40 was the major product following a Wittig reaction that followed a similar procedure to that used to prepare compound 38.

Example 24—Synthesis of 1,1,1-trifluoro-2-[4-[(Z)-2-[1-(4-isopropoxyphenyl)benzimidazol-5-yl]vinyl]phenyl]propan-2-ol (Compound 46)

1,1,1-trifluoro-2-[4-[(Z)-2-[1-(4-isopropoxyphenyl)benzimidazol-5-yl]vinyl]phenyl]propan-2-ol (compound 46) was synthesized according to the following scheme:

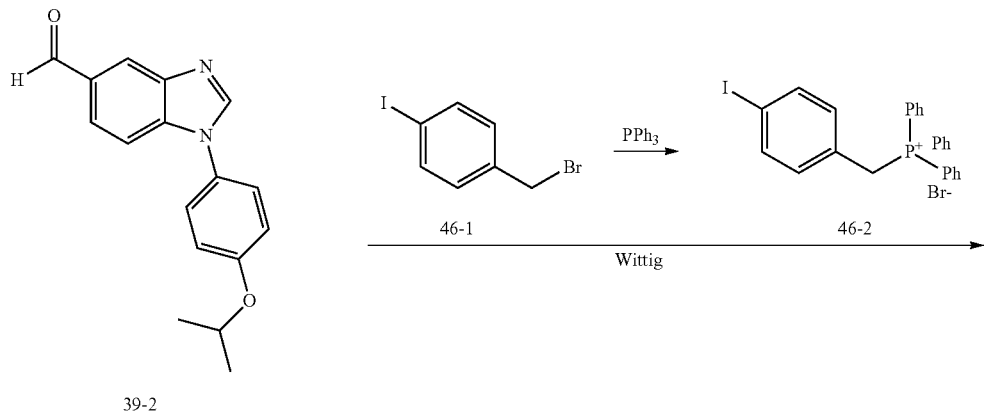

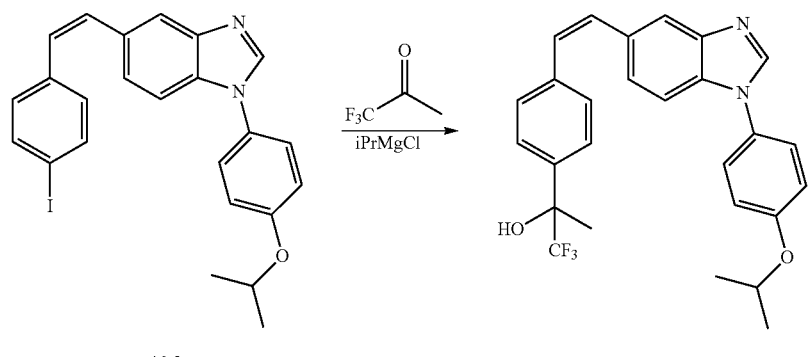

97

Example 24 was used as a general procedure for the synthesis of compounds 50, 51, 52, 53, 55, 56, 57, 58 and 59. Please note that compounds 55 and 58 required an extra step following the Grignard reaction involving either saponification (compound 55) or removal of a Boc group (compound 58).

Synthesis of (4-iodobenzyl)triphenylphosphonium bromide (46-2)

Compound 46-2 was prepared from compound 46-1 using a similar procedure to that used to synthesize compound 1-8.

Synthesis of (Z)-5-(4-iodostyryl)-1-(4-isopropoxyphenyl)-1H-benzo[d]imidazole (Compound 46-3)

Compound 46-3 was synthesized in the same fashion as compound 1-8.

Synthesis of 1,1,1-trifluoro-2-[4-[(Z)-2-[1-(4-isopropoxyphenyl)benzimidazol-5-yl]vinyl]phenyl]propan-2-ol (Compound 46)

2M Isopropylmagnesium chloride in THF (3.85 mL, 7.75 mmol, 6.2 equiv) was added dropwise to a cold solution (−40° C.) of compound 46-3 (0.60 g, 1.25 mmol, 1 equiv) in anhydrous THF (12 mL). The reaction was stirred at −40° C. for 30 minutes, then cooled to −78° C. 1,1,1-Trifluoroacetone (0.23 mL, 2.5 mmol, 2 equiv) was added dropwise and the reaction was stirred at room temperature for 16 hours. The reaction was cooled to 0° C. and quenched with water (50 mL). The mixture was extracted with ethyl acetate (3×50 mL) and the combined organic layers were dried over sodium sulfate, filtered and concentrated under reduced pressure. The residue was purified on an AnaLogix automated chromatography system, eluting with a gradient of 0 to 40% ethyl acetate in heptanes to give compound 46 as a white solid (0.14 g, 24% yield).

Example 25—Synthesis of 1,1,1,3,3,3-hexafluoro-2-[4-[(Z)-2-[1-(4-isopropoxyphenyl)benzimidazol-5-yl]vinyl]phenyl]propan-2-ol (Compound 47)

1,1,1,3,3,3-hexafluoro-2-[4-[(Z)-2-[1-(4-isopropoxyphenyl)benzimidazol-5-yl]vinyl]phenyl]propan-2-ol (compound 47) was synthesized according to the following scheme:

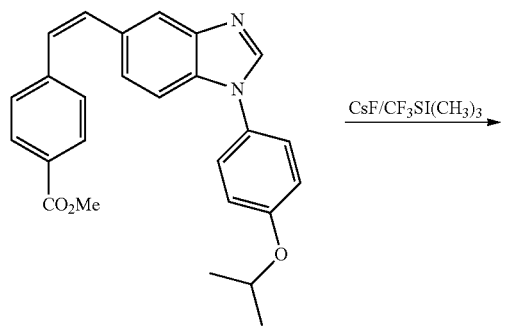

37

-continued

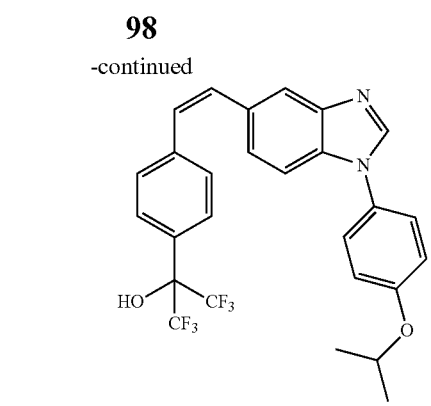

47

Synthesis of 1,1,1,3,3,3-hexafluoro-2-[4-[(Z)-2-[1-(4-isopropoxyphenyl)benzimidazol-5-yl]vinyl]phenyl]propan-2-ol (Compound 47)

Cesium fluoride (0.23 g, 1.5 mmol, 0.9 equiv) and (trifluoromethyl)trimethylsilane (0.75 mL, 5.1 mmol, 3 equiv) were added to a cold solution (0° C.) of compound 37 (0.7 g, 1.7 mmol, 1.0 equiv) in tetrahydrofuran (50 mL). The reaction was stirred overnight at room temperature, when LC/MS analysis indicated that the starting material was not completely consumed. Additional (trifluoromethyl)trimethylsilane (0.38 mL, 2.6 mmol, 1.5 equiv) was added and after 6 hours the reaction was partitioned between ethyl acetate (10 mL) and water (10 mL). The aqueous layer was extracted with ethyl acetate (2×10 mL). The combined organic layers were dried over sodium sulfate and concentrated under reduced pressure. The residue was purified on an AnaLogix (SF 15-24 g) column, eluting with a gradient of 0 to 3% methanol in dichloromethane, to give compound 47 as an off white solid (82 mg, 10% yield).

Example 26—Synthesis of 1-[4-[(Z)-2-[1-(4-isopropoxyphenyl)benzimidazol-5-yl]vinyl]phenyl]cyclopropanol (Compound 48)

1-[4-[(Z)-2-[1-(4-isopropoxyphenyl)benzimidazol-5-yl]vinyl]phenyl]cyclopropanol (compound 48) was synthesized according to the following scheme:

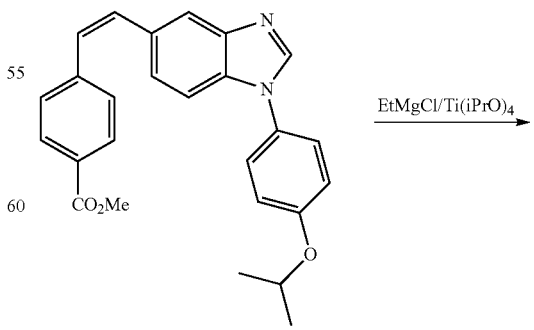

37

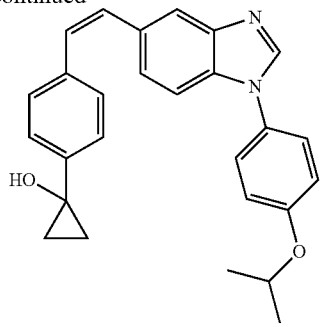

48

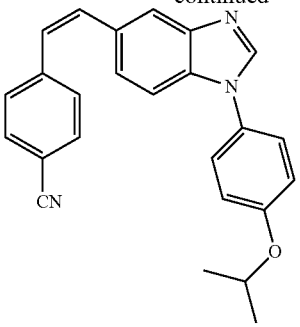

49

Synthesis of 1-[4-[(Z)-2-[1-(4-isopropoxyphenyl) benzimidazol-5-yl]vinyl]phenyl]cyclopropanol (Compound 48)

2.7M Ethylmagnesium chloride (2.5 mL, 6.8 mmol, 2.8 equiv) was added dropwise, at room temperature, to a solution of compound 37 (1 g, 2.4 mmol, 1.0 equiv), titanium isopropoxide (1 mL, 3.4 mmol, 1.4 equiv) and tetrahydrofuran (10 mL). The reaction was stirred overnight, when LC/MS analysis indicated the presence of starting material. Additional titanium isopropoxide (1 mL, 3.4 mmol, 1.4 equiv) and 2.7M ethylmagnesium chloride in tetrahydrofuran (2.5 mL, 6.8 mmol, 2.8 equiv) were added. The reaction was quenched with water (10 mL) and extracted with ethyl acetate (3×10 mL). The combined organic layers were dried over sodium sulfate and concentrated under reduced pressure. The residue was purified on an AnaLogix (SF 15-24 g) column, eluting with a gradient of 0 to 40% ethyl acetate in heptanes. The product was subjected to further purification by preparative HPLC, using a gradient of 0% to 95% acetonitrile (0.1% formic acid) in water (0.1% formic acid), to give compound 48 as a light yellow solid (50 mg, 5% yield).

Example 27—Synthesis of 4-[(Z)-2-[1-(4-isopropoxyphenyl)benzimidazol-5-yl]vinyl]benzonitrile (Compound 49) and 1-[4-[(Z)-2-[1-(4-isopropoxyphenyl)benzimidazol-5-yl]vinyl]phenyl]cyclopropanamine (Compound 54)

4-[(Z)-2-[1-(4-isopropoxyphenyl)benzimidazol-5-yl]vinyl]benzonitrile (compound 49) and 1-[4-[(Z)-2-[1-(4-isopropoxyphenyl)benzimidazol-5-yl]vinyl]phenyl]cyclopropanamine (compound 54) were synthesized according to the following scheme:

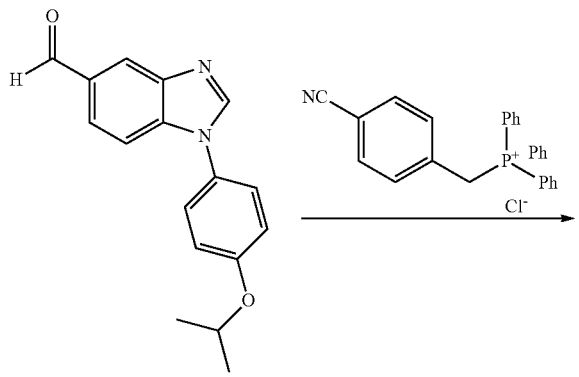

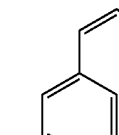

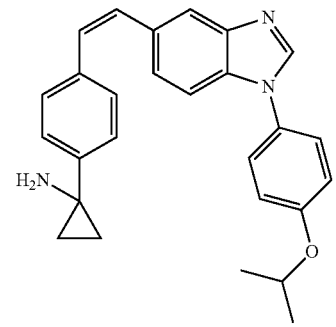

54

Synthesis of 4-[(Z)-2-[1-(4-isopropoxyphenyl)benzimidazol-5-yl]vinyl]benzonitrile (Compound 49)

To a suspension of (4-cyanobenzyl)triphenylphosphonium chloride (9.50 g, 22.95 mmol, 1.2 equiv) in anhydrous tetrahydrofuran (380 mL) at 0° C. was added a 60% dispersion of sodium hydride in mineral oil (1.53 g, 38.24 mmol, 2 equiv). The reaction was stirred at 0° C. for 1 hour, then cooled to −78° C. Compound 39-2 (5.35 g, 19.12 mmol, 1 equiv) was added and the reaction was slowly warmed to room temperature and stirred for 16 hours. The reaction was filtered, concentrated under reduced pressure and the residue was purified on an AnaLogix automated chromatography system (dry-loaded), eluting with a gradient of 5 to 40% ethyl acetate in heptanes, to give compound 49 as a white solid (1.57 g, 22% yield).

Synthesis of 1-[4-[(Z)-2-[1-(4-isopropoxyphenyl) benzimidazol-5-yl]vinyl]phenyl]cyclopropanamine (Compound 54)

To a solution of compound 49 (1 g, 2.6 mmol, 1.0 equiv) and titanium tetra-isopropoxide (18 mL, 6.3 mmol, 2.4 equiv) in tetrahydrofuran (50 mL) was added dropwise 2.7M ethylmagnesium chloride (4.3 mL, 11.6 mmol, 4.4 equiv) at −78° C. The reaction was allowed to slowly warm to room temperature for 1 hour. Boron trifluoride etherate (0.65 mL, 5.3 mmol, 2 equiv) was added, stirred for 16 hours and then quenched with the sequential addition of 1N HCl (aq.) (20 mL) and 10% sodium hydroxide (100 mL). The mixture was extracted with ethyl acetate (3×20 mL) and the combined organic layers were dried over sodium sulfate and concentrated under reduced pressure. The residue was purified on an AnaLogix automated chromatography system, eluting with a gradient of 0 to 4% methanol in dichloromethane. The product was subject to a second purification by preparative HPLC using a gradient of 0% to 95% acetonitrile (0.1% formic acid) in water (0.1% formic acid). The resulting salt was adjusted to pH 8 with 10% sodium hydroxide. The aqueous layer was extracted with MTBE (3×20 mL), dried over sodium sulfate and concentrated under reduced pressure. The residue was again purified on an AnaLogix automated chromatography system, eluting with a gradient of 0 to 4% methanol in dichloromethane, to give compound 54 as an off-white wax (63 mg, 6% yield).

Example 28—Synthesis of 2-[4-[(Z)-2-[1-(4-isopropoxyphenyl)benzimidazol-5-yl]vinyl]phenyl]propan-2-amine (Compound 60)

2-[4-[(Z)-2-[1-(4-isopropoxyphenyl)benzimidazol-5-yl]vinyl]phenyl]propan-2-amine (compound 60) was synthesized according to the following scheme:

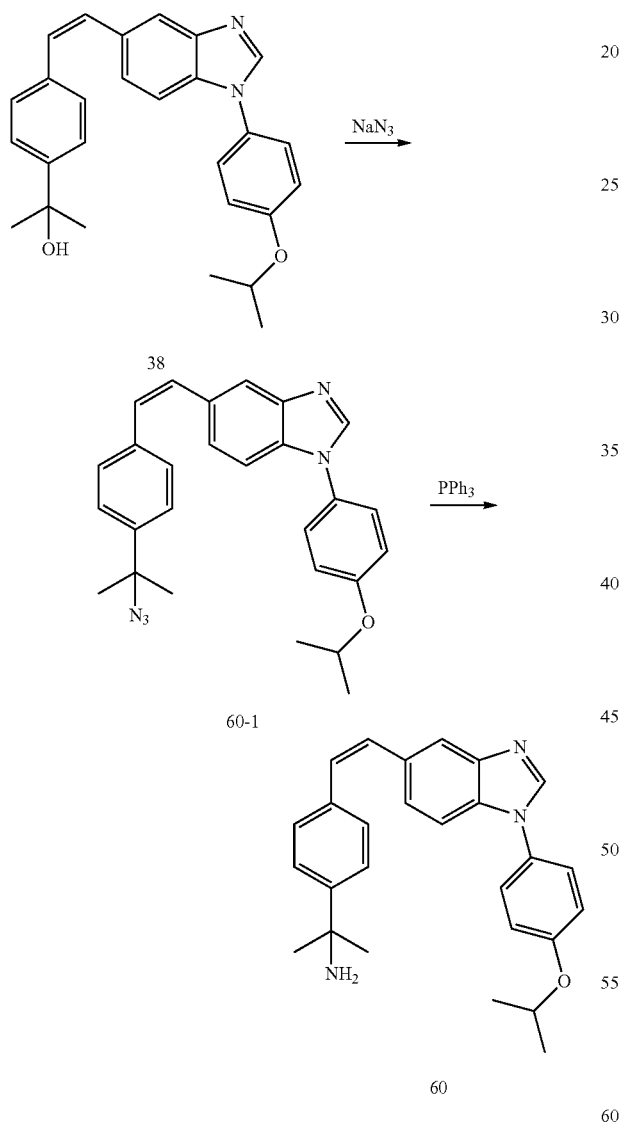

Synthesis of (Z)-5-(4-(2-azidopropan-2-yl)styryl)-1-(4-isopropoxyphenyl)-1H-benzo[d]imidazole (Compound 60-1)

Trifluoroacetic acid (0.5 mL) was added dropwise at room temperature to a suspension of compound 38 (0.39 g, 0.95 mmol, 1 equiv) and sodium azide (0.14 g, 2.08 mmol, 2.2 equiv) in chloroform (1 mL). The reaction was stirred at room temperature for 16 hours and then quenched with saturated ammonium hydroxide (5 mL). The mixture was extracted with dichloromethane (3×5 mL) and the combined organic layers were dried over sodium sulfate, filtered, and concentrated under reduced pressure to give compound 60-1 as an orange oil (0.42 g, >99% yield), which was used directly in the next step.

Synthesis of 2-[4-[(Z)-2-[1-(4-isopropoxyphenyl)benzimidazol-5-yl]vinyl]phenyl]propan-2-amine (Compound 60)

Compound 60-1 (0.42 g, 0.95 mmol, 1 equiv) and triphenylphosphine (0.27 g, 1.05 mmol, 1.1 equiv) were heated in a mixture of THF (2 mL) and water (0.2 mL) at 50° C. for 16 hours. The reaction was concentrated under reduced pressure and the residue was purified on an AnaLogix automated chromatography system, eluting with a gradient of 0 to 10% methanol in dichloromethane, to give compound 60 as a clear wax (59 mg, 15% yield).

Example 29—Synthesis of 3-(4-Ethoxybenzyl)-N-(4-ethylbenzyl)-3H-imidazo[4,5-b]pyridin-6-amine (Compound 62)

3-(4-Ethoxybenzyl)-N-(4-ethylbenzyl)-3H-imidazo[4,5-b]pyridin-6-amine (compound 62) was synthesized according to the following scheme:

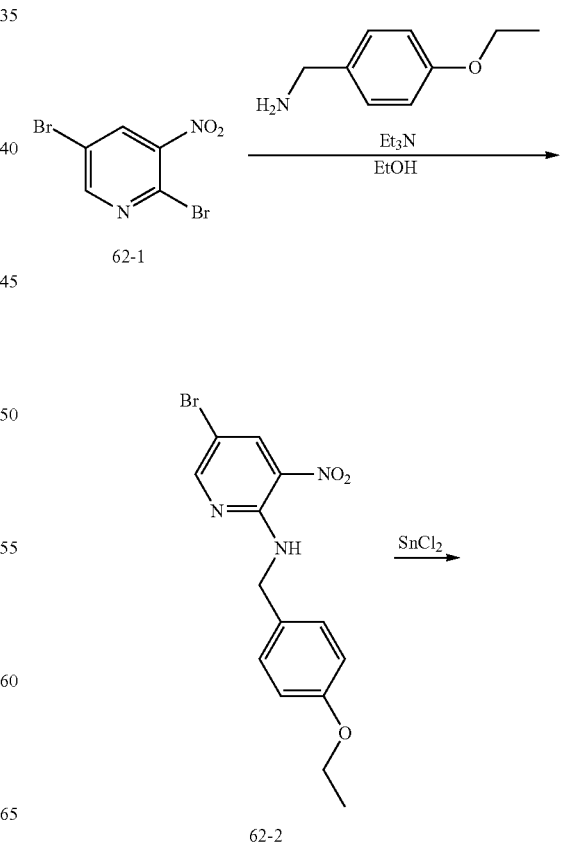

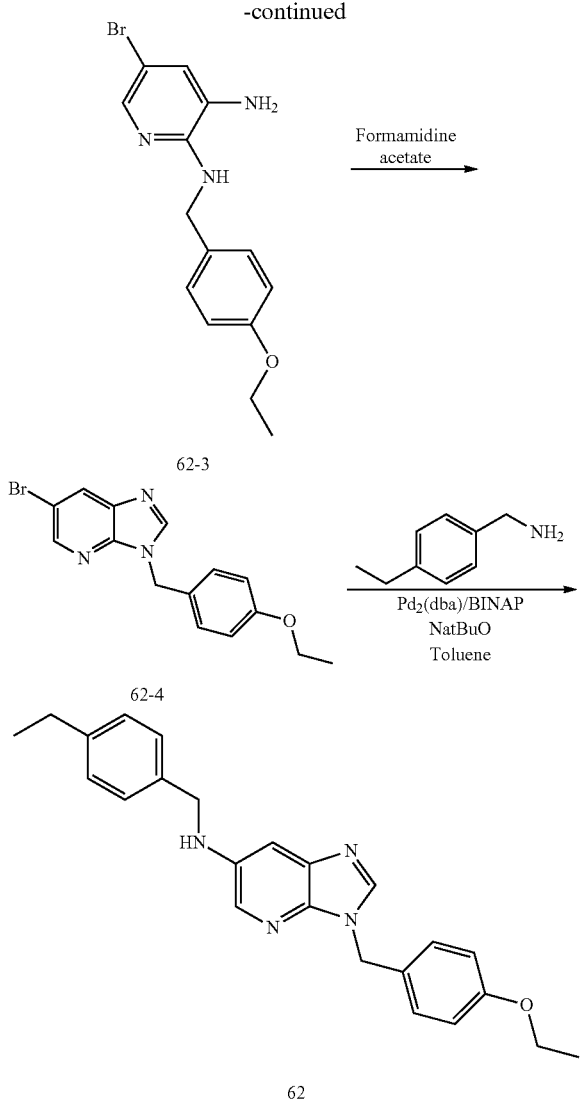

Synthesis of 5-Bromo-N-(4-ethoxybenzyl)-3-nitropyridin-2-amine (Compound 62-2)

To a stirred solution of 2,5-dibromo-3-nitropyridine (1 g, 3.5 mmol, 1 equiv) in ethanol (10 mL) was added a (4-ethoxyphenyl)methanamine (580 µL, 3.9 mmol, 1.1 equiv) and triethylamine (1 mL, 7.1 mmol, 2 equiv). The reaction mixture was allowed to stir at room temperature for 18 hours, at which time LC-MS indicated the reaction was complete. The suspension was filtered and the solid washed with ethanol (2×5 mL) to produce compound 62-2 as a yellow solid (1.1 g, 92% yield).

Synthesis of 5-Bromo-N2-(4-ethoxybenzyl)pyridine-2,3-diamine (Compound 62-3)

A solution of compound 62-2 (1.1 g, 3.1 mmol, 1 equiv) in a 1:1 mixture of ethyl acetate/tetrahydrofuran (20 mL) was heated to 60° C. Tin(II) chloride dihydrate (2.5 g, 11 mmol, 3.5 equiv) was added portion wise and the reaction was stirred at 60° C. overnight. The reaction mixture was cooled to room temperature and diluted with saturated aqueous sodium bicarbonate (50 mL). The mixture was filtered through Celite and the pad was washed with ethyl acetate (2×50 mL). The layers were separated and the aqueous phase was washed with ethyl acetate (2×50 mL). The combined organic phases were dried over sodium sulfate and evaporated to dryness under reduce pressure to produce compound 62-3 as a brown oil (1 g, quantitative yield).

Synthesis of 6-Bromo-3-(4-ethoxybenzyl)-3H-imidazo[4,5-b]pyridine (Compound 62-4)

Compound 62-3 (1 g, 3.1 mmol, 1 equiv) was dissolved in 2-methoxyethanol (80 mL) and formamidine acetate (1.0 g, 9.3 mmol, 3 equiv) was added. The reaction was heated at reflux overnight, at which time LC-MS indicated the reaction was complete. The reaction was cooled to room temperature and concentrated to dryness. The residue was suspended in water (30 ml) and stirred for 1 h. The suspension was filtered and the solid was washed with water (2×5 mL). The material was dried in a vacuum oven at 45° C. overnight to give compound 62-4 as a tan solid (0.8 g, 81% yield).

Synthesis of 3-(4-Ethoxybenzyl)-N-(4-ethylbenzyl)-3H-imidazo[4,5-b]pyridin-6-amine (Compound 62)

A solution of compound 62-4 (0.5 g, 1.5 mmol, 1 equiv), tris(dibenzylideneacetone) palladium(0) chloroform adduct (0.08 g, 0.08 mmol, 0.05 equiv), racemic BINAP (0.09 g, 0.15 mmol, 0.1 equiv), (4-ethylphenyl)methanamine (325 µL, 2.3 mmol, 1.5 equiv), and sodium tert-butoxide (0.22 g, 2.3 mmol, 1.5 equiv) in toluene (30 mL) was degassed with a stream of nitrogen for 10 minutes. The reaction was heated at reflux overnight, at which time LC-MS indicated the reaction was complete. The reaction was diluted with ethyl acetate (50 mL), filtered through Celite and the pad was washed with ethyl acetate (50 mL). The filtrate was concentrated under reduced pressure, diluted with water (50 mL) and extracted with ethyl acetate (3×50 mL). The organic layers were combined, dried over sodium sulfate, and evaporated under reduce pressure. The compound was purified on an AnaLogix (SF 15-24 g) column. The gradient utilized for the purification was 2 minutes isocratic at 30% ethyl acetate in heptanes followed by a ramp to 80% ethyl acetate in heptanes over 40 minutes to give compound 62 as a tan solid (100 mg, 17% yield).

Example 30—Synthesis of 1-(4-Ethoxyphenyl)-N-(4-ethylbenzyl)-1H-indol-5-amine (Compound 63)

1-(4-Ethoxyphenyl)-N-(4-ethylbenzyl)-1H-indol-5-amine (compound 63) was synthesized according to the following scheme:

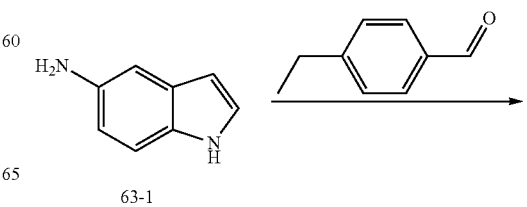

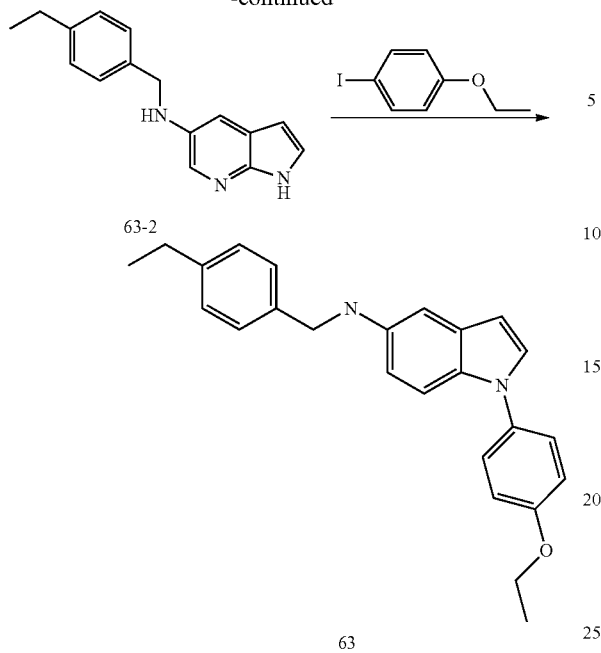

Synthesis of N-(4-Ethylbenzyl)-1H-indol-5-amine (Compound 63-2)

To a stirred solution of 5-aminoindole (0.73 g, 5.5 mmol, 1 equiv) in methanol (10 mL) was added 4-ethylbenzaldehyde (0.74 g, 5.5 mmol, 1.1 equiv). The reaction mixture was allowed to stir at room temperature for 30 minutes at which time sodium borohydride (0.21 g, 5.5 mmol, 1 equiv) was added and stirring continued for 30 minutes. Upon completion of the reaction, saturated aqueous sodium bicarbonate (4 mL) was added and the solution was stirred for 30 minutes. This reaction mixture was poured into dichloromethane (10 mL) and extracted. The dichloromethane was separated, dried over sodium sulfate and removed under reduced pressure. This material (compound 63-2) was used in the next step without further purification.

Synthesis of 1-(4-Ethoxyphenyl)-N-(4-ethylbenzyl)-1H-indol-5-amine (Compound 63)

Crude compound 63-2 was dissolved in N,N'-dimethylformamide (10 mL) along with 4-iodophenetole (1.37 g, 5.5 mmol, 1 equiv), copper iodide (0.105 g, 0.55 mmol, 0.1 equiv), N,N,N',N'-tetramethylenediamine (0.126 g, 1.10 mmol, 0.2 equiv), and potassium carbonate (1.14 g, 8.25 mmol, 1.5 equiv). The mixture was heated at 100° C. for 48 hours. Upon completion, the mixture was concentrated under reduced pressure and the residue was purified by silica gel chromatography using a gradient of 0-50% ethyl acetate in heptanes to give compound 63 as a white solid (117 mg, 6% yield).

Example 31—Synthesis of 3-(4-Ethoxyphenyl)-N-(4-ethylbenzyl)-1H-indol-6-amine (Compound 64)

3-(4-Ethoxyphenyl)-N-(4-ethylbenzyl)-1H-indol-6-amine (compound 64) was synthesized according to the following scheme:

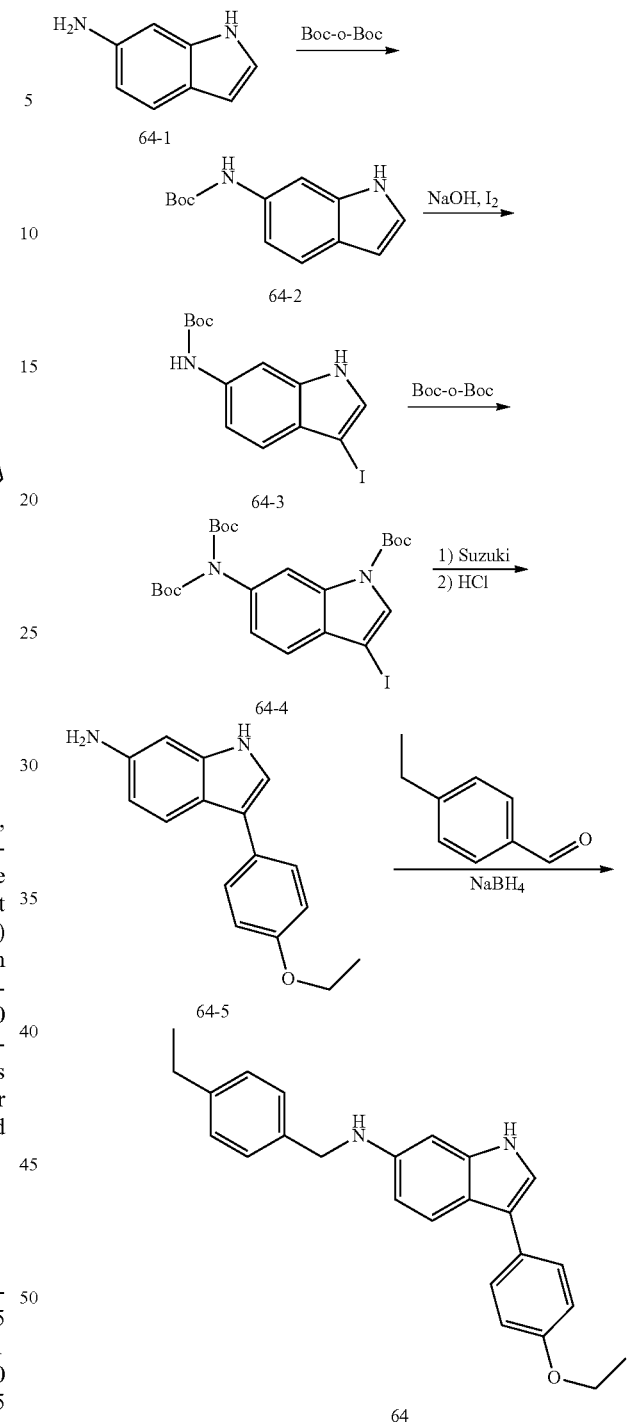

Synthesis of tert-Butyl 1H-indol-6-ylcarbamate (Compound 64-2)

To a stirred solution of 1H-indol-6-amine (1.12 g, 8.5 mmol, 1 equiv) was added di-tert-butyl dicarbonate (1.95 g, 8.9 mmol, 1.05 equiv) in tetrahydrofuran (6 mL). Saturated aqueous sodium bicarbonate (6 mL) was added and the reaction was stirred at room temperature for 18 hours. The layers were separated and the aqueous layer was extracted with ethyl acetate (3×5 mL). The organic layers were combined, dried over sodium sulfate and concentrated under reduced pressure to give compound 64-2 as a white solid (2.2 g, 97% yield).

Synthesis of tert-Butyl 3-iodo-1H-indol-6-ylcarbamate (Compound 64-3)

To a solution of compound 64-2 (2.3 g, 10 mmol, 1 equiv) in dimethyl formamide (10 mL) was added potassium carbonate powder (3.5 g, 25 mmol, 2.5 equiv) followed by a solution of iodine (2.7 g, 10.5 mmol, 1.05 equiv) in dimethyl formamide (10 mL). The reaction was stirred at room temperature for 3 h and then poured into saturated brine (200 mL) and methyl tert-butyl ether (100 mL). The layers were separated and the aqueous phase was extracted with methyl tert-butyl ether (3×50 mL). The organic layers were combined, back extracted with brine (3×100 mL), and dried over sodium sulfate. The extracts were filtered and concentrated under reduced pressure to give compound 64-3 as a yellow solid (3.5 g, 99% yield).

Synthesis of tert-Butyl 6-(bis(tert-butoxycarbonyl) amino)-3-iodo-1H-indole-1-carboxylate (Compound 64-4)

To a solution of compound 64-3 (3.5 g, 10 mmol, 1 equiv) in dichloromethane (50 mL) was added di-tert-butyl dicarbonate (4.5 g, 21 mmol, 2.5 equiv) followed by triethylamine (3.5 mL, 25 mmol, 2.5 equiv) and N,N-4-dimethyl aminopyridine (120 mg, 1 mmol, 0.1 equiv). The solution began to reflux on its own upon addition of the dimethylaminopyridine. The reaction was stirred at room temperature for 18 hours. At that time, the reaction was concentrated under reduced pressure to a thick white residue. The residue was purified by column chromatography utilizing a gradient of 0-50% ethyl acetate in heptanes to produce compound 64-4 as a white solid (3.5 g, 63% yield).

Synthesis of 3-(4-Ethoxyphenyl)-1H-indol-6-amine (Compound 64-5)

A suspension of compound 64-4 (1.12 g, 2 mmol, 1 equiv), Pd(PPh$_3$)$_4$ (116 mg, 0.1 mmol, 0.05 equiv), 4-ethoxyphenylboronic acid (350 mg, 2.1 mmol, 1.05 equiv), and sodium carbonate (424 mg, 4 mmol, 2 equiv) in a 3:1 mixture of dioxane and water (20 mL) was degassed with a stream of nitrogen for 10 minutes. The reaction was heated at reflux for 3 h, at which time LC-MS indicated the reaction was complete. Ethyl acetate (20 mL) was added and the layers were separated. The organic layer was dried over sodium sulfate, filtered through silica gel (2 g) and the silica gel was washed with ethyl acetate (15 mL). The filtrates were evaporated under reduce pressure and the residue was purified by column chromatography eluting with a gradient of 0-25% ethyl acetate in heptanes. This purified material was dissolved in dioxane (10 mL) and a 4.0M hydrogen chloride solution in dioxane (3.5 mL) was added. The reaction was stirred at room temperature over the weekend. The solvent was removed under reduced pressure and water (50 mL) was added. The pH was adjusted to 8 with 1N sodium hydroxide and the aqueous phase was extracted with a 3:1 mixture of ethyl acetate:tetrahydrofuran (3×20 mL). The organic layers were combined, dried over sodium sulfate, and concentrated under reduced pressure to give compound 64-5 as an off white solid (270 mg, 54% yield).

Synthesis of 3-(4-Ethoxyphenyl)-N-(4-ethylbenzyl)-1H-indol-6-amine (Compound 64)

To a solution of compound 64-5 (270 mg, 1.07 mmol, 1 equiv) in methanol was added 4-ethyl benzaldehyde (250 µL, 1.7 mmol, 1.7 equiv). Then, acetic acid (5 drops) was added and the reaction was stirred at room temperature for 2 hours. Sodium borohydride (250 mg) was added until LC analysis showed complete conversion of the peak assumed to be the imine. The product from 4 runs was chromatographed on an AnaLogix 12 g column using a gradient of 15-30% ethyl acetate in heptanes as the eluent. The product containing fractions were combined and concentrated under reduced pressure. This residue was triturated with 10% ethyl acetate in heptanes (5 mL) and the solid dried to give compound 64 as a yellow solid (58 mg, 14% yield).

Example 32—Synthesis of 3-(4-Ethoxyphenyl)-N-(4-ethylbenzyl) imidazo[1,2-a]pyridin-7-amine (Compound 65)

3-(4-Ethoxyphenyl)-N-(4-ethylbenzyl)imidazo[1,2-a] pyridin-7-amine (compound 65) was synthesized according to the following scheme:

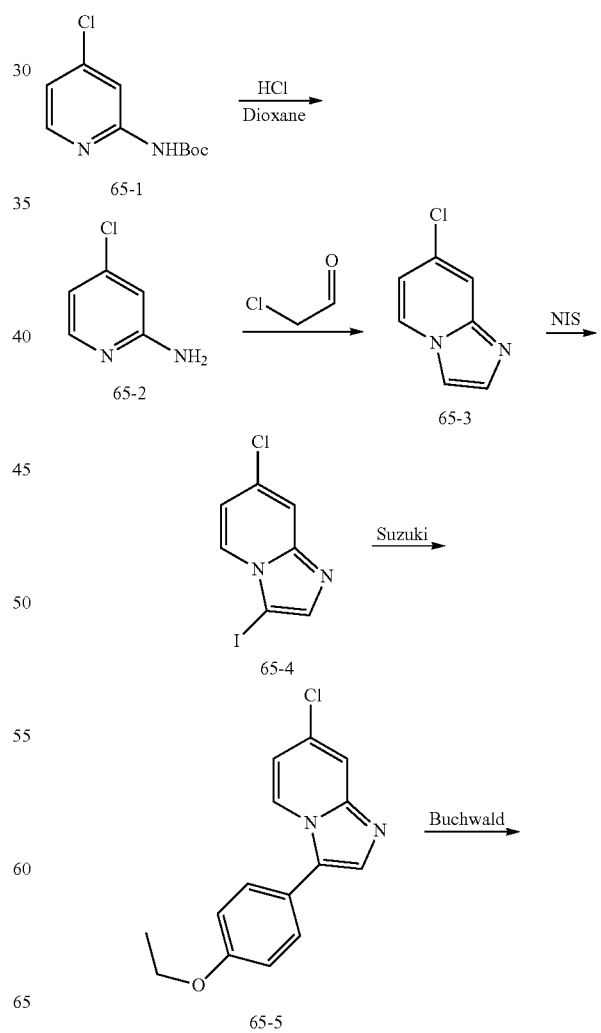

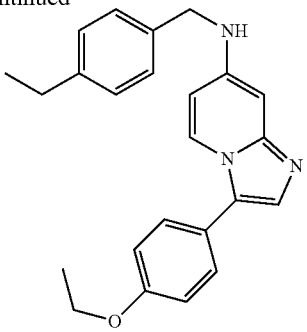

65

Synthesis of 4-Chloropyridin-2-amine (Compound 65-2)

To a stirred solution of tert-butyl 4-chloropyridin-2-ylcarbamate (2 g, 8.7 mmol, 1 equiv) was added a 4N solution of hydrogen chloride in dioxane (10 mL, 40 mmol, 4.6 equiv). The solution was allowed to stir for 18 hours at room temperature. The reaction was concentrated under reduced pressure to give compound 65-2 (HCl) as a reddish yellow solid (1.5 g, 100% yield).

Synthesis of 7-Chloroimidazo[1,2-a]pyridine (Compound 65-3)

To a suspension of compound 65-2 (HCl) in ethanol (15 mL) was added sodium bicarbonate powder (3.3 g, 38.4 mmol, 4 equiv) and a 50% solution of chloroacetaldehyde in water (2.26 g, 14.4 mmol, 1.5 equiv). The reaction was heated at reflux for 4 hours and stirred at room temperature for 16 hours. The reaction was concentrated under reduced pressure and the residue was dissolved in water (10 mL) and ethyl acetate (10 mL). The layers were separated and the aqueous phase was extracted with ethyl acetate (2×5 mL). The organic layers were combined, dried over sodium sulfate, filtered and concentrated to give compound 65-3 as a dark yellow oil (980 mg, 89% yield).

Synthesis of 7-Chloro-3-iodoimidazo[1,2-a]pyridine (Compound 65-4)

To a solution of compound 65-3 (450 mg, 2.9 mmol, 1 equiv) in dimethyl formamide (4.5 mL) was added N-iodosuccinimide (700 mg, 3.1 mmol, 1.05 equiv). The reaction was stirred at room temperature for 6 hours followed by the addition of water (20 ml) and ethyl acetate (20 ml). The layers were separated and the aqueous phase was extracted with ethyl acetate (3×5 ml). The organic layers were combined, dried over sodium sulfate, filtered and concentrated under reduced pressure to a black residue. The residue from 2 runs was chromatographed on an AnaLogix 8 g column using a gradient of 0-70% ethyl acetate in heptanes. The product containing fractions were combined and washed with saturated sodium thiosulfate solution (2×20 ml) to remove the remaining iodine color. The fractions were concentrated to give compound 65-4 as a white solid (829 mg, 50% yield).

Synthesis of 7-Chloro-3-(4-ethoxyphenyl)imidazo[1,2-a]pyridine (Compound 65-5)

A suspension of compound 65-4 (200 mg, 0.72 mmol, 1 equiv), Pd(PPh$_3$)$_4$ (41 mg, 0.036 mmol, 0.05 equiv), 4-ethoxyphenylboronic acid (121.5 mg, 0.73 mmol, 1.02 equiv), and sodium carbonate (152 mg, 1.4 mmol, 2 equiv) in 3:1 mixture of dioxane and water (20 mL) was degassed with a stream of nitrogen for 10 minutes. The reaction was heated at 90° C. for 3 h, at which time LC-MS indicated the reaction was complete. Ethyl acetate (10 mL) was added and the layers were separated. The organic layer was dried over sodium sulfate, filtered through silica gel (2 g) and the silica gel was washed with ethyl acetate (15 mL). The filtrates were evaporated under reduce pressure and the product was triturated with methyl tert-butyl ether (3 mL) to give compound 65-5 as an off white solid. (130 mg, 70% yield)

Synthesis of 3-(4-Ethoxyphenyl)-N-(4-ethylbenzyl)imidazo[1,2-a]pyridin-7-amine (Compound 65)

A suspension of compound 65-5 (162 mg, 0.59 mmol, 1 equiv), tris(dibenzylideneacetone) palladium(0) chloroform adduct (31 mg, 0.03 mmol, 0.05 equiv), racemic BINAP (37 mg, 0.059 mmol, 0.1 equiv), 4-ethyl benzylamine (130 μL, 0.89 mmol, 1.5 equiv), and sodium tert-butoxide (86 mg, 0.89 mmol, 1.5 equiv) in toluene (15 mL) was degassed with a stream of nitrogen for 5 minutes. The reaction was heated at reflux for 18 h, at which time LC-MS indicated the reaction was complete. The mixture was concentrated under reduced pressure, diluted with water (20 mL) and extracted with ethyl acetate (3×10 mL). The organic layers were combined, dried over sodium sulfate, and evaporated under reduced pressure. The product was chromatographed on an AnaLogix 8 g column using a gradient of 20-100% ethyl acetate in heptanes as the eluent to give compound 65 as a brown sticky solid (48 mg, 27% yield).

Example 33—Synthesis of 1-(4-ethoxyphenyl)-N-(4-ethylbenzyl)-1H-pyrrolo[2,3-b]pyridin-5-amine (Compound 66)

1-(4-ethoxyphenyl)-N-(4-ethylbenzyl)-1H-pyrrolo[2,3-b]pyridin-5-amine (compound 66) was synthesized according to the following scheme:

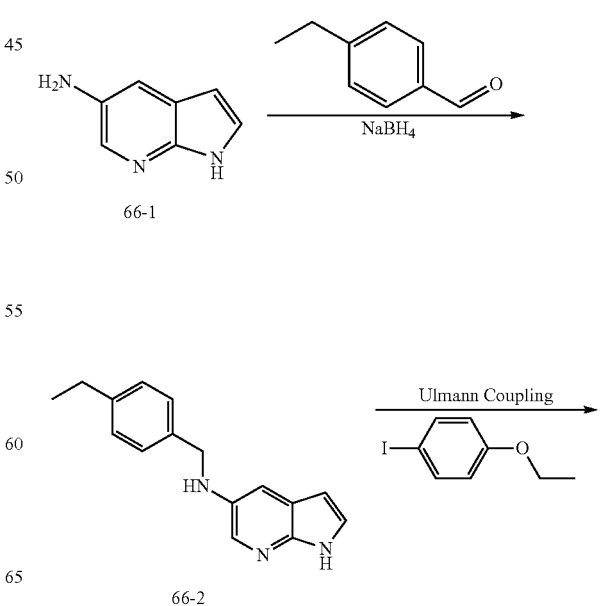

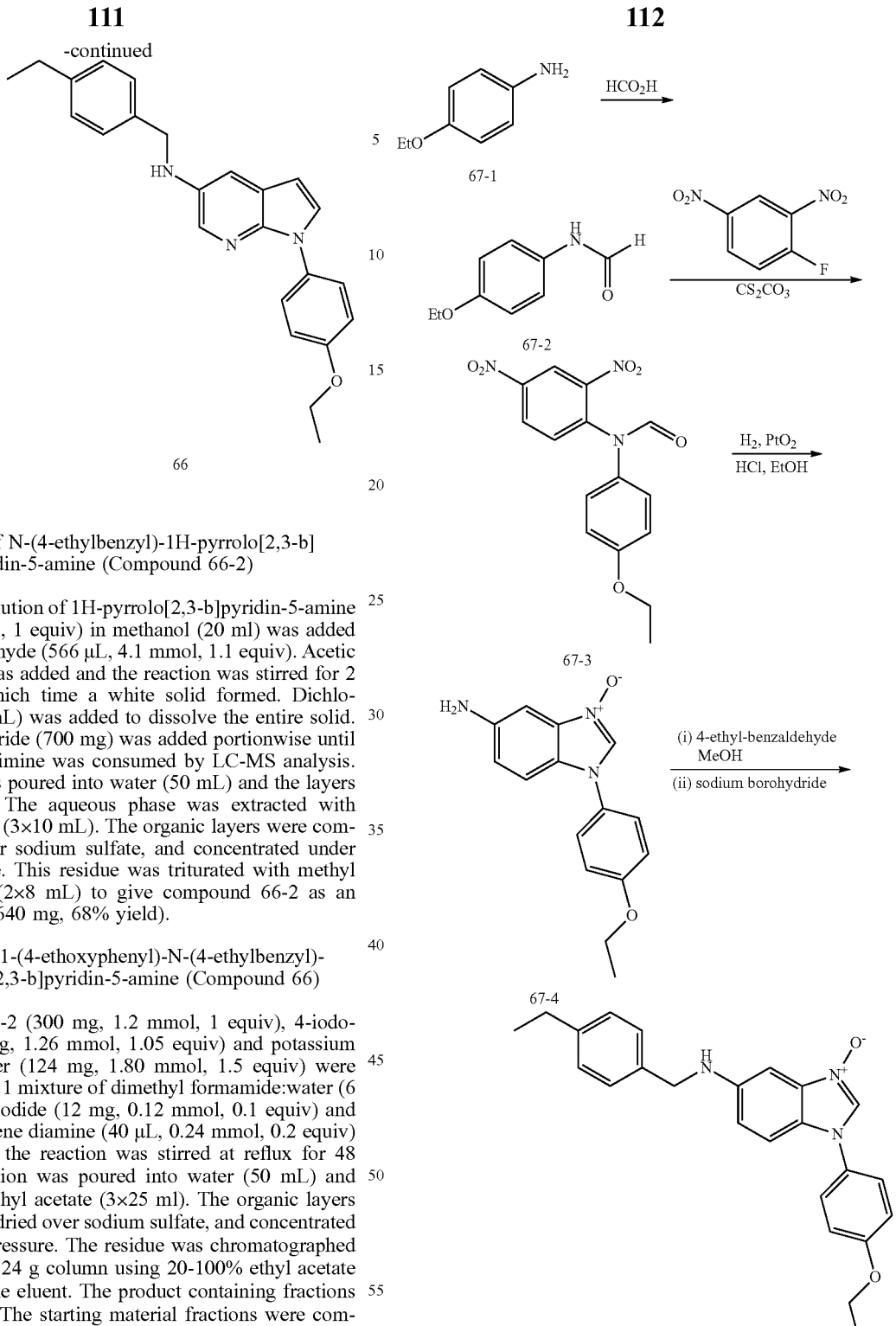

Synthesis of N-(4-ethylbenzyl)-1H-pyrrolo[2,3-b]pyridin-5-amine (Compound 66-2)

To a stirred solution of 1H-pyrrolo[2,3-b]pyridin-5-amine (0.5 g, 3.8 mmol, 1 equiv) in methanol (20 ml) was added 4-ethyl benzaldehyde (566 µL, 4.1 mmol, 1.1 equiv). Acetic acid (5 drops) was added and the reaction was stirred for 2 hours during which time a white solid formed. Dichloromethane (30 mL) was added to dissolve the entire solid. Sodium borohydride (700 mg) was added portionwise until all intermediate imine was consumed by LC-MS analysis. The reaction was poured into water (50 mL) and the layers were separated. The aqueous phase was extracted with dichloromethane (3×10 mL). The organic layers were combined, dried over sodium sulfate, and concentrated under reduced pressure. This residue was triturated with methyl tert-butyl ether (2×8 mL) to give compound 66-2 as an off-white solid (640 mg, 68% yield).

Synthesis of 1-(4-ethoxyphenyl)-N-(4-ethylbenzyl)-1H-pyrrolo[2,3-b]pyridin-5-amine (Compound 66)

Compound 66-2 (300 mg, 1.2 mmol, 1 equiv), 4-iodophenatol (310 mg, 1.26 mmol, 1.05 equiv) and potassium carbonate powder (124 mg, 1.80 mmol, 1.5 equiv) were suspended in a 5:1 mixture of dimethyl formamide:water (6 mL). Copper(I) iodide (12 mg, 0.12 mmol, 0.1 equiv) and tetramethylethylene diamine (40 µL, 0.24 mmol, 0.2 equiv) were added and the reaction was stirred at reflux for 48 hours. The reaction was poured into water (50 mL) and extracted with ethyl acetate (3×25 ml). The organic layers were combined, dried over sodium sulfate, and concentrated under reduced pressure. The residue was chromatographed on an AnaLogix 24 g column using 20-100% ethyl acetate in heptanes as the eluent. The product containing fractions were combined. The starting material fractions were combined and resubjected to the reaction to get more material. The product from 4 runs was combined to give compound 66 as an off-white solid (50 mg, 7.3% yield).

Example 34—Synthesis of 1-(4-Ethoxyphenyl)-5-(4-ethylbenzylamino)-1H-benzo[d]imidazole 3-oxide (Compound 67)

1-(4-Ethoxyphenyl)-5-(4-ethylbenzylamino)-1H-benzo[d]imidazole 3-oxide (compound 67) was synthesized according to the following scheme:

Synthesis of N-(4-Ethoxyphenyl)formamide (Compound 67-2)

p-Phenetidine (1 g, 7.29 mmol, 1.0 equiv) and formic acid (0.55 mL, 14.58 mmol, 2.0 equiv) were heated to 50° C. for 6 hours and then stirred at room temperature overnight. The reaction mixture was poured into water (100 mL), the mixture stirred vigorously for 15 min and the resulting oily suspension extracted with tert-butyl methyl ether (100 mL). The organic phase was washed with saturated aqueous sodium bicarbonate solution (100 mL), water (100 mL) and brine (100 mL), dried over sodium sulfate and concentrated under reduced pressure to give a light brown syrup (1.16 g). The crude product was purified on an AnaLogix (SF 25-80 g) column using a gradient of 0-100% ethyl acetate in heptanes to give compound 67-2 as an off-white solid (0.98 g, 81% yield).

Synthesis of N-(2,4-Dinitrophenyl)-N-(4-ethoxyphenyl)-formamide (Compound 67-3)

To a solution of 2,4-dinitrofluorobenzene (0.37 g, 2.0 mmol, 1.0 equiv) and compound 67-2 (0.33 g, 2.0 mmol, 1.0 equiv) in anhydrous dimethyl sulfoxide (12 mL) was added cesium carbonate (0.65 g, 2.0 mmol, 1.0 equiv). The reaction mixture was stirred at room temperature under nitrogen for 19 hours. The reaction mixture was poured into 1.0 M aqueous hydrochloric acid solution (100 mL) and the resulting suspension extracted with ethyl acetate (100 mL). The organic phase was washed with 1.0 M aqueous sodium hydroxide solution (2×100 mL), water (100 mL) and brine (100 mL), dried over sodium sulfate and concentrated under reduced pressure to give an orange syrup (0.33 g). The crude product was purified on an AnaLogix (SF 25-40 g) column using a gradient of 0-100% ethyl acetate in heptanes to give compound 67-3 as a yellow syrup (135 mg, 21% yield).

Synthesis of 5-Amino-1-(4-ethoxyphenyl)-1H-benzo[d]imidazole 3-oxide (Compound 67-4)

To platinum dioxide (30 mg) was added a solution of compound 67-3 (135 mg, 0.408 mmol, 1.0 equiv) in absolute ethanol (20 mL) followed by 4.0 M hydrogen chloride in dioxane (0.26 mL, 1.02 mmol, 2.5 equiv) and the mixture was hydrogenated at 15 psi for 2.5 hours. The mixture was filtered through Celite, washing through with ethyl acetate, and the filtrate concentrated under reduced pressure to give a pink solid. The crude product was dissolved in dichloromethane (30 mL), 1.0 M aqueous sodium carbonate solution (5 mL) was added and the biphasic mixture stirred vigorously for 2 hours. Following the addition of a saturated brine solution (20 mL), the organic phase was separated, washed with saturated brine (20 mL), dried over sodium sulfate and concentrated under reduced pressure to give a brown solid (100 mg). The crude product was purified on an AnaLogix (SF 15-24 g) column using a gradient of 0-10% methanol in dichloromethane followed by a gradient of 0-100% ethanol in dichloromethane to give compound 67-4 as a brown solid (28.2 mg, 26% yield).

Synthesis of 1-(4-Ethoxyphenyl)-5-(4-ethylbenzylamino)-1H-benzo[d]imidazole 3-oxide (Compound 67)

To a solution compound 67-4 (24.1 mg, 0.089 mmol, 1.0 equiv) in anhydrous methanol (1 mL) at room temperature under nitrogen was added 4-ethylbenzaldehyde (0.014 mL, 0.098 mmol, 1.1 equiv) and the reaction mixture stirred at room temperature for 6 hours. Sodium borohydride (3.4 mg, 0.089 mmol, 1.0 equiv) was added and the reaction mixture stirred at room temperature for an additional 15 minutes. The reaction was quenched by the addition of a saturated aqueous ammonium chloride solution (4 mL), the mixture stirred vigorously for 5 minutes and extracted with ethyl acetate (30 mL). The organic phase was separated, washed with brine (2×20 mL), dried over sodium sulfate and concentrated under reduced pressure to give a yellow solid. The crude product was purified on an AnaLogix (SF 15-24 g) column using a gradient of 0-10% methanol in dichloromethane to give compound 67 as a tan solid (26.2 mg, 76% yield).

Example 35—Determining Antiviral Activity of Compounds of the Invention

Work with Lassa fever virus presents significant logistical and safety issues due to the requirement for maximum laboratory containment (BSL-4). Therefore, surrogate assays for anti-Lassa fever virus activity were developed that would be suitable for evaluating large numbers of compounds under less-restrictive BSL-2 laboratory conditions. One such assay was developed to identify compounds that can block Lassa virus entry into the host cell. This assay uses only the envelope glycoprotein from Lassa fever virus, not the virus itself, and thus can safely be performed under normal BSL-2 conditions. The viral entry step is an attractive target for the development of antiviral pharmaceuticals, because it is an essential component of every viral life cycle. In addition, the antiviral targets, the interaction between the viral envelope and the host cell and subsequent structural rearrangement of the envelope, are specific to the virus. Thus, effective inhibitors are less likely to interfere with host processes.

Viral pseudotypes, which are generated by cotransfection of the Lassa envelope and a replication-defective HIV provirus with a luciferase reporter, are used to assess Lassa envelope function. The provirus is engineered so that the HIV envelope is not expressed, and thus heterologous viral envelope proteins are acquired as budding viral particles nonspecifically capture cell surface proteins. Pseudotypes prepared in this manner will infect cells via the heterologous envelope and are commonly used to assay functions of the heterologous envelope (2,9,26,31,33). Infection is measured by the luciferase signal produced from the integrated HIV reporter construct. The amount of infectious virus used to infect a cell culture line is directly proportional, over several orders of magnitude, to the luciferase-mediated luminescence produced in the infected cells.

Benzimidazole compounds were screened for antiviral activity and served as the basis for subsequent examination of the structure-activity relationship. A number of very potent antiviral compounds were identified as shown in Tables 3 and 4. For the alkene linked analogs for which both cis and trans versions were synthesized (compounds 1-25), compounds with the cis configuration had submicromolar $EC_{50}$ values, whereas only about half of the analogs with the trans configuration displayed potency in the same range. For compounds 27-33, it was apparent that the presence of a carbon, oxygen, or sulfur linker did not have a large effect on antiviral potency. The majority of the compounds included in Table 2 involved exploration of nitrogen atom positioning about the bicyclic core. We were able to mostly retain submicromolar antiviral potency throughout the study involving addition, subtraction, and repositioning of nitrogen atoms.

The compounds disclosed herein were synthesized to improve potencies, solubility and other properties. As indicated above, Compound 2 is shown to be very potent with a submicromolar $EC_{50}$ value in the assay against Lassa GP-pseudotyped-virus in 293T cells (Table 3).

TABLE 3

Anti-Viral for compounds of Formula I of the present invention.

Activity ($EC_{50}$ in μM vs. pseudotyped virus)
A: $EC_{50} < 1$ μM; B: $1 \leq EC_{50} < 10$ μM; C: $10 \leq EC_{50} < 50$ μM; D: $EC_{50} \geq 50$ μM; n.d.: not determined

| Compound | Lassa | Machupo | Guanarito | Junín | Sabiá | VSVg |
|---|---|---|---|---|---|---|
| 1 | A | A | n.d. | n.d. | n.d. | C |
| 2 | A | A | A | A | A | C |
| 3 | B | n.d. | n.d. | n.d. | n.d. | C |
| 4 | A | n.d. | n.d. | n.d. | n.d. | C |
| 5 | A | A | n.d. | A | A | C |
| 6 | A | n.d. | n.d. | n.d. | n.d. | C |
| 7 | A | A | n.d. | A | A | C |
| 8 | A | A | n.d. | A | n.d. | C |
| 9 | A | A | n.d. | A | A | C |
| 10 | A | B | n.d. | A | n.d. | D |
| 11 | A | A | n.d. | A | n.d. | C |
| 12 | C | *Note 1 | n.d. | C | n.d. | **Note 2 |
| 13 | A | A | n.d. | A | n.d. | C |
| 14 | B | n.d. | n.d. | n.d. | n.d. | C |
| 15 | A | n.d. | n.d. | n.d. | A | C |
| 16 | B | n.d. | n.d. | n.d. | n.d. | C |
| 17 | A | n.d. | n.d. | n.d. | A | C |
| 18 | A | n.d. | n.d. | B | n.d. | C |
| 19 | A | A | n.d. | A | A | C |
| 20 | A | n.d. | n.d. | n.d. | n.d. | B |
| 21 | A | A | n.d. | A | A | C |
| 22 | A | A | n.d. | A | n.d. | C |
| 23 | B | n.d. | n.d. | n.d. | n.d. | D |
| 24 | A | A | n.d. | A | A | C |
| 25 | B | n.d. | n.d. | n.d. | n.d. | D |
| 26 | B | C | n.d. | B | n.d. | C |
| 27 | A | A | A | A | A | D |
| 28 | A | A | n.d. | A | n.d. | D |
| 29 | A | A | n.d. | A | n.d. | C |
| 30 | A | A | n.d. | A | n.d. | C |
| 31 | A | A | A | A | A | C |
| 32 | A | A | n.d. | A | A | C |
| 33 | A | A | A | A | A | C |
| 34 | A | A | n.d. | A | n.d. | C |
| 35 | A | A | n.d. | n.d. | n.d. | C |
| 36 | A | A | n.d. | A | n.d. | C |
| 37 | A | A | n.d. | A | n.d. | C |
| 38 | A | A | n.d. | A | n.d. | B |
| 39 | A | A | n.d. | A | n.d. | B |
| 40 | A | A | n.d. | A | n.d. | C |
| 41 | A | A | n.d. | n.d. | n.d. | C |
| 42 | A | A | n.d. | n.d. | n.d. | B |
| 43 | A | A | n.d. | n.d. | n.d. | B |
| 44 | A | n.d. | n.d. | n.d. | n.d. | C |
| 45 | C | A | n.d. | A | B | D |
| 46 | A | A | n.d. | n.d. | n.d. | B |
| 47 | A | A | n.d. | n.d. | n.d. | B |
| 48 | A | A | n.d. | A | n.d. | C |
| 49 | A | n.d. | n.d. | n.d. | n.d. | C |
| 50 | A | A | n.d. | A | n.d. | B |
| 51 | A | A | n.d. | A | n.d. | B |
| 52 | A | A | n.d. | A | n.d. | B |
| 53 | A | A | n.d. | A | n.d. | B |
| 54 | A | A | n.d. | A | n.d. | C |
| 55 | A | n.d. | n.d. | n.d. | n.d. | D |
| 56 | A | A | n.d. | n.d. | n.d. | B |
| 57 | A | A | n.d. | n.d. | n.d. | B |
| 58 | B | A | n.d. | A | n.d. | C |
| 59 | A | A | n.d. | A | n.d. | B |
| 60 | A | A | n.d. | A | n.d. | D |
| 61 | A | A | n.d. | A | A | C |

*Note 1:
$EC_{50} = 51$ μM
**Note 2:
$EC_{50} = 196$ μM

TABLE 4

Anti-Viral for compounds of Formula II of the present invention.

Activity ($EC_{50}$ in μM vs. pseudotyped virus)
A: $EC_{50} < 1$ μM; B: $1 \leq EC_{50} < 10$ μM; C: $10 \leq EC_{50} < 50$ μM; D: $EC_{50} \geq 50$ μM; n.d.: not determined

| Compound | Lassa | Machupo | Guanarito | Junín | Sabiá | VSVg |
|---|---|---|---|---|---|---|
| 62 | B | B | n.d. | n.d. | n.d. | B |
| 63 | A | A | n.d. | n.d. | n.d. | C |
| 64 | A | A | n.d. | A | n.d. | C |
| 65 | A | A | n.d. | A | n.d. | B |
| 66 | A | B | n.d. | n.d. | n.d. | D |
| 67 | A | A | n.d. | A | n.d. | C |

REFERENCES

1. Beyer, W. R., D. Popplau, W. Garten, D. von Laer, and O. Lenz. 2003. Endoproteolytic processing of the lymphocytic choriomeningitis virus glycoprotein by the subtilase SKI-1/S1P. J Virol 77:2866-2872.
2. Beyer, W. R., M. Westphal, W. Ostertag, and D. von Laer. 2002. Oncoretrovirus and lentivirus vectors pseudotyped with lymphocytic choriomeningitis virus glycoprotein: generation, concentration, and broad host range. J Virol 76:1488-1495.
3. Borio, L., T. Inglesby, C. J. Peters, A. L. Schmaljohn, J. M. Hughes, P. B. Jahrling, T. Ksiazek, K. M. Johnson, A. Meyerhoff, T. O'Toole, M. S. Ascher, J. Bartlett, J. G. Breman, E. M. Eitzen, Jr., M. Hamburg, J. Hauer, D. A. Henderson, R. T. Johnson, G. Kwik, M. Layton, S. Lillibridge, G. J. Nabel, M. T. Osterholm, T. M. Perl, P. Russell, and K. Tonat. 2002. Hemorrhagic fever viruses as biological weapons: medical and public health management. JAMA 287:2391-2405.
4. Buchmeier, M. J., M. D. Bowen, and C. J. Peters. 2001. Arenaviridae: the viruses and their replication, p. 1635-1668. In D. M. Knipe and P. M. Howley (ed.), Fields virology, 4th ed. ed. Lippincott, Williams and Wilkins, Philadelphia Pa.
5. Burns, J. W., and M. J. Buchmeier. 1991. Protein-protein interactions in lymphocytic choriomeningitis virus. Virology 183:620-629.
6. Cao, W., M. D. Henry, P. Borrow, H. Yamada, J. H. Elder, E. V. Ravkov, S. T. Nichol, R. W. Compans, K. P. Campbell, and M. B. A. Oldstone. 1998. Identification of adystroglycan as a receptor for lymphocytic choriomeningitis virus and Lassa fever virus. Science 282:2079-2081.
7. Centers for Disease Control and Prevention. 2004. Imported Lassa fever—New Jersey, 2004. MMWR Morb Mortal Wkly Rep 53:894-897.
8. Colman, P. M., and M. C. Lawrence. 2003. The structural biology of type I viral membrane fusion. Nat Rev Mol Cell Bioi 4:309-319.
9. Connor, R. I., B. K. Chen, S. Choe, and N. R. Landau. 1995. Vpr is required for efficient replication of human immunodeficiency virus type-1 in mononuclear phagocytes. Virology 206:935-944.
10. Cummins, D., J. B. McCormick, D. Bennett, J. A. Samba, B. Farrar, S. J. Machin, and S. P. Fisher-Hoch. 1990. Acute sensorineural deafness in Lassa fever. JAMA 264:20932096.
11. Eichler, R., O. Lenz, T. Strecker, M. Eickmann, H.-D. Klenk, and W. Garten. 2003. Identification of Lassa virus glycoprotein signal peptide as a trans-acting maturation factor. EMBO Rep 4:1084-1088.
12. Eichler, R., O. Lenz, T. Strecker, M. Eickmann, H.-D. Klenk, and W. Garten. 2004. Lassa virus glycoprotein signal peptide displays a novel topology with an extended endoplasmic reticulum luminal region. J Biol Chem 279: 12293-12299.
13. Eichler, R., O. Lenz, T. Strecker, and W. Garten. 2003. Signal peptide of Lassa virus glycoprotein GP-C exhibits an unusual length. FEBS Lett 538:203-206.
14. Fisher-Hoch, S. P., O. Tomori, A. Nasidi, G. I. Perez-Oronoz, Y. Fakile, L. Hutwagner, and J. B. McCormick. 1995. Review of cases of nosocomial Lassa fever in Nigeria: the high price of poor medical practice. BMJ 311:857-859.
15. Gallaher, W. R., C. DiSimone, and M. J. Buchmeier. 2001. The viral transmembrane superfamily: possible divergence of *Arenavirus* and Filovirus glycoproteins from a common RNA virus ancestor. BMC Microbiol 1:1.
16. Geisbert, T. W., S. Jones, E. A. Fritz, A. C. Shurtleff, J. B. Geisbert, R. Liebscher, A. Grolla, U. Stroher, L. Fernando, K. M. Daddario, M. C. Guttieri, B. R. Mothe, T. Larsen, L. E. Hensley, P. B. Jahrling, and H. Feldmann. 2005. Development of a new vaccine for the prevention of Lassa fever. PLoS Med 2:e183.
17. Haas, W. H., T. Breuer, G. Pfaff, H. Schmitz, P. Kohler, M. Asper, P. Emmerich, C. Drosten, U. Golnitz, K. Fleischer, and S. Gunther. 2003. Imported Lassa fever in Germany: surveillance and management of contact persons. Clin Infect Dis 36:1254-1258.
18. Hass, M., U. Golnitz, S. MUlier, B. Becker-Ziaja, and S. Gunther. 2004. Replicon system for Lassa virus. J Virol78:13793-13803.
19. Jones, S. M., H. Feldmann, U. Stroher, J. B. Geisbert, L. Fernando, A. Grolla, H.-D. Klenk, N. J. Sullivan, V. E. Volchkov, E. A. Fritz, K. M. Daddario, L. E. Hensley, P. B. Jahrling, and T. W. Geisbert. 2005. Live attenuated recombinant vaccine protects nonhuman primates against Ebola and Marburg viruses. Nat Med 11:786-790.
20. Kunz, S., K. H. Edelmann, J. C. de la Torre, R. Gorney, and M. B. A. Oldstone. 2003. Mechanisms for lymphocytic choriomeningitis virus glycoprotein cleavage, transport, and incorporation into virions. Virology 314:168-178.
21. Lenz, O., J. ter Meulen, H.-D. Klenk, N. G. Seidah, and W. Garten. 2001. The Lassa virus glycoprotein precursor GP-C is proteolytically processed by subtilase SKI-1/S1P. Proc Natl Acad Sci USA 98:12701-12705.
22. Liao, B. S., F. M. Byl, and K. K. Adour. 1992. Audiometric comparison of Lassa fever hearing loss and idiopathic sudden hearing loss: evidence for viral cause. Otolaryngol Head Neck Surg 106:226-229.
23. McCormick, J. B., I. J. King, P. A. Webb, K. M. Johnson, R. O'Sullivan, E. S. Smith, S. Trippel, and T. C. Tong. 1987. A case-control study of the clinical diagnosis and course of Lassa fever. J Infect Dis 155:445-455.
24. McCormick, J. B., I. J. King, P. A. Webb, C. L. Scribner, R. B. Craven, K. M. Johnson, L. H. Elliott, and R. Belmont-Williams. 1986. Lassa fever. Effective therapy with ribavirin. N Engl J Med 314:20-26.
25. McCormick, J. B., P. A. Webb, J. W. Krebs, K. M. Johnson, and E. S. Smith. 1987. A prospective study of the epidemiology and ecology of Lassa fever. J Infect Dis 155:437444.
26. Naldini, L., U. Blomer, P. Gallay, D. Ory, R. Mulligan, F. H. Gage, I. M. Verma, and D. Trono. 1996. In vivo gene delivery and stable transduction of nondividing cells by a lentiviral vector. Science 272:263-267.
27. NIAID. 2002. NIAID biodefense research agenda for CDC category A agents. NIH Publication No. 03-5308.
28. O'Brien, J., I. Wilson, T. Orton, and F. Pognan. 2000. Investigation of the Alamar Blue (resazurin) fluorescent dye for the assessment of mammalian cell cytotoxicity. Eur J Biochem 267:5421-5426.
29. Perez, M., R. C. Craven, and J. C. de la Torre. 2003. The small RING finger protein Z drives *arenavirus* bUdding: implications for antiviral strategies. Proc Natl Acad Sci USA 100: 12978-12983.
30. Rotz, L. D., A. S. Khan, S. R. Lillibridge, S. M. Ostroff, and J. M. Hughes. 2002. Public health assessment of potential biological terrorism agents. Emerg Infect Dis 8:225-230.
31. Simmons, G., J. D. Reeves, A. J. Rennekamp, S. M. Amberg, A. J. Piefer, and P. Bates. 2004. Characterization of severe acute respiratory syndrome-associated coronavirus (SARS-CoV) spike glycoprotein-mediated viral entry. Proc Natl Acad Sci USA 101:4240-4245.
32. Spiropoulou, C. F., S. Kunz, P. E. Rollin, K. P. Campbell, and M. B. A. Oldstone. 2002. New World *arenavirus* Glade C, but not Glade A and B viruses, utilizes a-dystroglycan as its major receptor. J Virol 76:5140-5146.
33. Wool-Lewis, R. J., and P. Bates. 1998. Characterization of Ebola virus entry by using pseudotyped viruses: identification of receptor-deficient cell lines. J Virol72:3155-3160.
34. World Health Organization. 2000. WHO Lassa fever fact sheet No. 179.

All references cited herein are herein incorporated by reference in their entirety for all purposes.

The invention has been described in terms of preferred embodiments thereof, but is more broadly applicable as will be understood by those skilled in the art.

What is claimed is:

1. A compound selected from the group consisting of:
   1-(4-ethoxyphenyl)-N-[(4-ethylphenyl)methyl]indol-5-amine,
   3-(4-ethoxyphenyl)-N-[(4-ethylphenyl)methyl]-1H-indol-6-amine,
   1-(4-ethoxyphenyl)-N-[(4-ethylphenyl)methyl]pyrrolo[2,3-b]pyridin-5-amine,
   1-(4-ethoxyphenyl)-5-[2-(4-ethylphenyl)ethyl]benzimidazole;
   3-(4-ethoxyphenyl)-6-[2-(4-ethylphenyl)-ethyl]imidazo[4,5-b]pyridine,
   1-(4-ethoxyphenyl)-5-[(4-ethylphenyl)-methoxy]benzimidazole,
   5-[(4-isopropylphenyl)methoxy]-1-(4-methoxyphenyl)benzimidazole,
   3-(4-ethoxyphenyl)-6-[(4-ethylphenyl)methoxy]imidazo[4,5-b]pyridine,
   6-[(4-isopropylphenyl)methoxy]-3-(4-methoxyphenyl)imidazo[4,5-b]pyridine,
   1-(4-ethoxyphenyl)-5-[(4-ethylphenyl)methylsulfanyl]benzimidazole,
   5-[12-(4-tert-butylphenyl)cyclopropyl]-1-(4-isopropoxyphenyl)benzimidazole, and
   pharmaceutically acceptable salts thereof.

2. A pharmaceutical composition comprising a pharmaceutically acceptable carrier or excipient and a compound of claim 1 or a pharmaceutically acceptable salt thereof.

* * * * *

UNITED STATES PATENT AND TRADEMARK OFFICE
CERTIFICATE OF CORRECTION

Page 1 of 1

PATENT NO.        : 10,000,486 B2
APPLICATION NO.   : 15/353351
DATED             : June 19, 2018
INVENTOR(S)       : Dongcheng Dai et al.

It is certified that error appears in the above-identified patent and that said Letters Patent is hereby corrected as shown below:

In the Claims

Claim 1, Column 118, Line 59:
"5-[12-(4-tert-butylphenyl)cyclopropyl]-1-(4-isopropoxyphenyl)benzimidazole"
Should be corrected to:
--5-[2-(4-tert-butylphenyl)cyclopropyl]-1-(4-isopropoxyphenyl)benzimidazole--

Signed and Sealed this
Fifth Day of March, 2019

Andrei Iancu
*Director of the United States Patent and Trademark Office*